(12) United States Patent
Beach et al.

(10) Patent No.: US 9,066,679 B2
(45) Date of Patent: Jun. 30, 2015

(54) ULTRASONIC TECHNIQUE FOR ASSESSING WALL VIBRATIONS IN STENOSED BLOOD VESSELS

(75) Inventors: Kirk W. Beach, Seattle, WA (US); Yongmin Kim, Lake Forest Park, WA (US); Siddhartha Sikdar, Washington, DC (US)

(73) Assignee: University of Washington, Seattle, WA (US)

( * ) Notice: Subject to any disclaimer, the term of this patent is extended or adjusted under 35 U.S.C. 154(b) by 1299 days.

(21) Appl. No.: 12/815,310

(22) Filed: Jun. 14, 2010

(65) Prior Publication Data

US 2010/0286522 A1  Nov. 11, 2010

Related U.S. Application Data

(63) Continuation-in-part of application No. 11/218,292, filed on Aug. 31, 2005, now Pat. No. 7,736,314.

(60) Provisional application No. 60/606,162, filed on Aug. 31, 2004.

(51) Int. Cl.
*A61B 8/00* (2006.01)
*A61B 8/08* (2006.01)
(Continued)

(52) U.S. Cl.
CPC ............... *A61B 8/08* (2013.01); *A61B 5/02007* (2013.01); *A61B 5/7257* (2013.01); *A61B 8/06* (2013.01);
(Continued)

(58) Field of Classification Search
None
See application file for complete search history.

(56) References Cited

U.S. PATENT DOCUMENTS

| 385,256 A | 6/1888 | Eggers |
| 2,992,553 A | 7/1961 | Joy ................................. 73/644 |

(Continued)

FOREIGN PATENT DOCUMENTS

| DE | 04230415 | 3/1994 | ............... A61B 8/00 |
| EP | 0 420 758 | 4/1991 | ............... A61B 8/00 |

(Continued)

OTHER PUBLICATIONS

Lalonde et al., "Field conjugate acoustic lenses for ultrasound hyperthermia." *Ultrasonics, Ferroelectrics and Frequency Control, IEEE Transactions*, vol. 40, Issue 5: Abstract 1pg., Sep. 1993.

(Continued)

*Primary Examiner* — Unsu Jung
*Assistant Examiner* — Michael N Fisher
(74) *Attorney, Agent, or Firm* — Kilpatrick Townsend and Stockton LLP

(57) ABSTRACT

A real-time signal processing technique for ultrasonic imaging of tissue vibrations for localizing the source of a bruit in a 2D image with respect to the anatomy and/or for obtaining simultaneous information about vibrations and the underlying blood flow. The bruit can be quantitatively assessed using an ensemble of ultrasound echoes. Signal processing enables estimation of wall displacement and the display of time-resolved vibration spectrum. Vibrations are detected and color-coded according to their amplitude and frequency and overlaid on the B-mode and/or color-flow image in real time. Proposed vibration imaging algorithms use data acquired during conventional ultrasonic color-flow imaging and the clutter signal, normally suppressed in color-flow imaging, to detect and characterize tissue vibrations. Three vibration imaging algorithms based on parametric modeling of vibrations and other criteria distinguish between clutter, blood flow, and vibrations. The techniques are usable to detect, locate, image, and quantitatively grade stenoses in blood vessels.

28 Claims, 35 Drawing Sheets

(51) Int. Cl.
*A61B 5/02* (2006.01)
*G01S 7/52* (2006.01)
*G01S 15/89* (2006.01)
*A61B 5/00* (2006.01)
*A61B 8/06* (2006.01)
*A61B 8/13* (2006.01)

(52) U.S. Cl.
CPC .............. *A61B 8/13* (2013.01); *G01S 7/52026* (2013.01); *G01S 7/52034* (2013.01); *G01S 7/52036* (2013.01); *G01S 7/52071* (2013.01); *G01S 15/8981* (2013.01); *A61B 8/0816* (2013.01)

(56) References Cited

U.S. PATENT DOCUMENTS

| | | | |
|---|---|---|---|
| 4,059,098 A | 11/1977 | Murdock | 73/644 |
| 4,484,569 A | 11/1984 | Driller et al. | 128/60 |
| 4,545,386 A | 10/1985 | Hetz et al. | 600/462 |
| 4,601,296 A | 7/1986 | Yerushalmi | 607/156 |
| 4,688,578 A | 8/1987 | Takano et al. | 600/459 |
| 4,770,184 A | 9/1988 | Greene, Jr. et al. | |
| RE33,590 E | 5/1991 | Dory | 128/999.999 |
| 5,039,774 A | 8/1991 | Shikinami et al. | 528/60 |
| 5,065,742 A | 11/1991 | Belikan et al. | 128/24 |
| 5,080,101 A | 1/1992 | Dory | 128/999.999 |
| 5,080,102 A | 1/1992 | Dory | 128/999.999 |
| 5,088,498 A | 2/1992 | Beach et al. | 600/453 |
| 5,150,712 A | 9/1992 | Dory | 128/999.999 |
| 5,170,790 A | 12/1992 | Lacoste et al. | 600/437 |
| 5,178,148 A | 1/1993 | Lacoste et al. | 600/439 |
| 5,183,046 A | 2/1993 | Beach et al. | 600/453 |
| 5,194,291 A | 3/1993 | D'Aoust et al. | 148/276 |
| 5,215,680 A | 6/1993 | D'Arrigo | 516/11 |
| 5,219,401 A | 6/1993 | Cathignol et al. | 128/999.999 |
| 5,230,334 A | 7/1993 | Klopotek | 128/999.999 |
| 5,289,820 A | 3/1994 | Beach et al. | 600/443 |
| 5,311,869 A | 5/1994 | Okazaki | 128/999.999 |
| 5,391,140 A | 2/1995 | Schaetzle et al. | 601/4 |
| 5,394,877 A | 3/1995 | Orr et al. | 600/459 |
| 5,471,988 A | 12/1995 | Fujio et al. | 128/999.999 |
| 5,474,071 A | 12/1995 | Chapelon et al. | 600/439 |
| 5,492,126 A | 2/1996 | Hennige et al. | 600/439 |
| 5,507,790 A | 4/1996 | Weiss | 607/100 |
| 5,520,188 A | 5/1996 | Hennige et al. | 128/999.999 |
| 5,522,878 A | 6/1996 | Montecalvo et al. | 607/152 |
| 5,526,815 A | 6/1996 | Granz et al. | 128/999.999 |
| 5,534,232 A | 7/1996 | Denes et al. | 422/186.26 |
| 5,536,489 A | 7/1996 | Lohrmann et al. | 424/9.52 |
| 5,558,092 A | 9/1996 | Unger et al. | 128/999.999 |
| 5,573,497 A | 11/1996 | Chapelon | 601/2 |
| 5,609,485 A | 3/1997 | Bergman et al. | 434/262 |
| 5,638,823 A | 6/1997 | Akay et al. | 600/528 |
| 5,657,760 A | 8/1997 | Ying et al. | 128/999.999 |
| 5,666,954 A | 9/1997 | Chapelon et al. | 600/439 |
| 5,720,286 A | 2/1998 | Chapelon et al. | 600/439 |
| 5,720,287 A | 2/1998 | Chapelon et al. | 600/439 |
| 5,755,228 A | 5/1998 | Wilson et al. | 600/459 |
| 5,762,066 A | 6/1998 | Law et al. | 128/999.999 |
| 5,769,790 A | 6/1998 | Watkins et al. | 600/439 |
| 5,807,285 A | 9/1998 | Vaitekunas et al. | 601/2 |
| 5,810,007 A | 9/1998 | Holupka et al. | 600/439 |
| 5,817,021 A | 10/1998 | Reichenberger | 600/439 |
| 5,823,962 A | 10/1998 | Schaetzle et al. | 600/439 |
| 5,824,277 A | 10/1998 | Campos | 423/242.1 |
| 5,827,204 A | 10/1998 | Grandia et al. | 601/2 |
| 5,833,647 A | 11/1998 | Edwards | 604/22 |
| 5,840,028 A * | 11/1998 | Chubachi et al. | 600/437 |
| 5,846,517 A | 12/1998 | Unger | 424/9.52 |
| 5,853,752 A | 12/1998 | Unger et al. | 424/450 |
| 5,873,828 A | 2/1999 | Fujio et al. | 600/439 |
| 5,879,314 A | 3/1999 | Peterson et al. | 601/2 |
| 5,882,302 A | 3/1999 | Driscoll, Jr. et al. | 600/371 |
| 5,895,356 A | 4/1999 | Andrus et al. | 600/439 |
| 5,897,495 A | 4/1999 | Aida et al. | 600/411 |
| 5,906,580 A | 5/1999 | Kline-Schoder et al. | 600/459 |
| 5,919,139 A | 7/1999 | Lin | 600/443 |
| 5,922,945 A | 7/1999 | Allmaras et al. | 73/52 |
| 5,931,786 A | 8/1999 | Whitmore, III et al. | 600/459 |
| 5,935,339 A | 8/1999 | Henderson et al. | 134/1 |
| 5,951,476 A | 9/1999 | Beach | 600/437 |
| 5,976,092 A | 11/1999 | Chinn | 600/459 |
| 5,993,389 A | 11/1999 | Driscoll, Jr. et al. | 600/371 |
| 5,997,481 A | 12/1999 | Adams et al. | 600/459 |
| 6,007,499 A | 12/1999 | Martin et al. | 601/3 |
| 6,036,650 A * | 3/2000 | Wu et al. | 600/462 |
| 6,039,694 A | 3/2000 | Larson et al. | 600/459 |
| 6,050,943 A | 4/2000 | Slayton et al. | 600/439 |
| 6,067,371 A | 5/2000 | Gouge et al. | 382/128 |
| 6,071,239 A | 6/2000 | Cribbs et al. | 600/439 |
| 6,128,522 A | 10/2000 | Acker et al. | 600/411 |
| 6,179,831 B1 | 1/2001 | Bliweis | 606/21 |
| 6,200,539 B1 | 3/2001 | Sherman et al. | 422/186.04 |
| 6,221,015 B1 | 4/2001 | Yock | 600/439 |
| 6,267,734 B1 | 7/2001 | Ishibashi et al. | 601/2 |
| 6,390,979 B1 | 5/2002 | Njemanze | 600/437 |
| 6,406,759 B1 | 6/2002 | Roth | 427/562 |
| 6,409,720 B1 | 6/2002 | Hissong et al. | 606/27 |
| 6,425,867 B1 | 7/2002 | Vaezy et al. | 600/439 |
| 6,443,894 B1 | 9/2002 | Sumanaweera et al. | 600/443 |
| 6,488,639 B1 | 12/2002 | Ribault et al. | 601/2 |
| 6,491,672 B2 | 12/2002 | Slepian et al. | 604/267 |
| 6,548,047 B1 | 4/2003 | Unger | 424/9.51 |
| 6,551,576 B1 | 4/2003 | Unger et al. | 424/9.52 |
| 6,584,360 B2 | 6/2003 | Francischelli et al. | 607/98 |
| 6,595,934 B1 | 7/2003 | Hissong et al. | 601/3 |
| 6,599,256 B1 | 7/2003 | Acker et al. | 601/2 |
| 6,626,855 B1 | 9/2003 | Weng et al. | 601/3 |
| 6,633,658 B1 | 10/2003 | Dabney et al. | 382/128 |
| 6,656,136 B1 | 12/2003 | Weng et al. | 601/2 |
| 6,676,601 B1 | 1/2004 | Lacoste et al. | 600/439 |
| 6,685,639 B1 | 2/2004 | Wang et al. | 600/439 |
| 6,706,892 B1 | 3/2004 | Ezrin et al. | 548/548 |
| 6,709,407 B2 | 3/2004 | Fatemi | 600/559 |
| 6,716,184 B2 | 4/2004 | Vaezy et al. | 601/3 |
| 6,719,694 B2 | 4/2004 | Weng et al. | 600/439 |
| 6,719,699 B2 | 4/2004 | Smith | 600/459 |
| 6,726,627 B1 | 4/2004 | Lizzi et al. | 600/439 |
| 6,735,461 B2 | 5/2004 | Vitek et al. | 600/411 |
| 6,764,488 B1 | 7/2004 | Burbank et al. | 606/51 |
| 6,846,291 B2 | 1/2005 | Smith et al. | 600/459 |
| 6,875,176 B2 | 4/2005 | Mourad et al. | 600/442 |
| 6,875,420 B1 | 4/2005 | Quay | 424/9.52 |
| 6,905,498 B2 | 6/2005 | Hooven | 606/50 |
| 6,932,771 B2 | 8/2005 | Whitmore et al. | 607/105 |
| 6,955,648 B2 | 10/2005 | Mozayeni et al. | 600/454 |
| 7,022,077 B2 | 4/2006 | Mourad et al. | 600/442 |
| 7,052,463 B2 | 5/2006 | Peszynski et al. | 600/459 |
| 7,285,093 B2 | 10/2007 | Anisimov et al. | 600/437 |
| 7,445,599 B2 | 11/2008 | Kelly et al. | 600/437 |
| 7,470,241 B2 | 12/2008 | Weng et al. | 601/3 |
| 7,534,209 B2 | 5/2009 | Abend | 600/437 |
| 7,547,283 B2 | 6/2009 | Mourad et al. | 600/442 |
| 7,628,764 B2 | 12/2009 | Duarte et al. | 601/2 |
| 7,684,865 B2 | 3/2010 | Aldrich et al. | 607/40 |
| 7,697,972 B2 | 4/2010 | Verard et al. | 600/424 |
| 7,736,314 B2 | 6/2010 | Beach et al. | 600/437 |
| 2002/0099286 A1* | 7/2002 | Sandler et al. | 600/407 |
| 2002/0193831 A1 | 12/2002 | Smith, III | 607/5 |
| 2003/0018255 A1 | 1/2003 | Martin et al. | 600/3 |
| 2003/0069569 A1 | 4/2003 | Burdette et al. | 600/427 |
| 2003/0171894 A1* | 9/2003 | Mancini et al. | 702/182 |
| 2003/0195420 A1 | 10/2003 | Mendlein et al. | 600/459 |
| 2004/0002654 A1 | 1/2004 | Davidson et al. | 600/454 |
| 2004/0078034 A1 | 4/2004 | Acker et al. | 606/27 |
| 2004/0097840 A1 | 5/2004 | Holmer | 601/2 |
| 2004/0122493 A1 | 6/2004 | Ishibashi et al. | 600/437 |
| 2004/0153126 A1 | 8/2004 | Okai | 606/27 |
| 2004/0234453 A1 | 11/2004 | Smith | 424/9.5 |
| 2004/0254620 A1 | 12/2004 | Lacoste et al. | 607/96 |
| 2005/0065436 A1 | 3/2005 | Ho et al. | 600/431 |
| 2005/0124881 A1* | 6/2005 | Kanai et al. | 600/437 |
| 2005/0182319 A1 | 8/2005 | Glossop | 600/424 |

(56) References Cited

U.S. PATENT DOCUMENTS

| | | | |
|---|---|---|---|
| 2005/0240102 A1 | 10/2005 | Rachlin et al. | 600/459 |
| 2006/0184069 A1 | 8/2006 | Vaitekunas | 601/2 |
| 2008/0045864 A1 | 2/2008 | Candy et al. | 601/2 |
| 2008/0045865 A1 | 2/2008 | Kislev | 601/3 |
| 2008/0200815 A1 | 8/2008 | Van Der Steen et al. | 600/467 |
| 2008/0319375 A1 | 12/2008 | Hardy | 604/22 |

FOREIGN PATENT DOCUMENTS

| | | | |
|---|---|---|---|
| EP | 1 265 223 | 12/2002 | G10K 11/35 |
| EP | 1 421 905 A1 | 5/2004 | |
| JP | 62-164441 | 7/1987 | |
| JP | 06-237929 | 8/1994 | |
| JP | 07-265304 | 10/1995 | |
| JP | H09-103434 | 4/1997 | A61B 17/36 |
| JP | 2000-041983 | 2/2000 | |
| JP | 2000-175915 | 6/2000 | |
| JP | 2000-229078 | 8/2000 | |
| JP | 2000-333957 | 12/2000 | |
| JP | 2001-506517 | 5/2001 | |
| JP | 2001-509724 | 7/2001 | |
| JP | 2002-500939 | 1/2002 | A61B 18/00 |
| JP | 2002-524180 | 8/2002 | |
| JP | 2002-532172 | 10/2002 | |
| JP | 03/15635 | 2/2003 | |
| JP | 2003-515423 | 5/2003 | |
| JP | 2004-113789 | 4/2004 | A61B 8/00 |
| WO | WO 97/31364 | 8/1997 | G10K 11/02 |
| WO | WO 00/72919 | 12/2000 | A61N 7/02 |
| WO | WO 02/069805 | 9/2002 | A61B 8/06 |

OTHER PUBLICATIONS

Miller et al., "A Review of In Vitro Bioeffects of Inertial Ultrasonic Cavitation From a Mechanistic Perspective." *Ultrasound in Medicine & Biology*, vol. 22, No. 9: 1131-1154, 1996.

Miller et al., "Diagnostic ultrasound activation of contrast agent gas bodies induces capillary rupture in mice." *PNAS*, vol. 97, No. 18: 10179-10184, 2000.

Ng et al., "Therapeutic Ultrasound: Its Application in Drug Delivery." *Medicinal Research Reviews*, vol. 22, No. 2: 204-233, 2002.

Ostensen et al., "Characterization and Use of Ultrasound Contrast Agents." Academy of Radiology, vol. 9, Suppl. 2: S276-S278, 2002.

Owaki et al., "The Ultrasonic Coagulating and Cutting System Injuries Nerve Function." *Endoscopy*, vol. 34, No. 7: 575-579, 2002.

Poliachik et al., "Activation, Aggregation and Adhesion of Platelets Exposed to High-Intensity Focused Ultrasound." *Ultrasound in Medicine & Biology*, vol. 27, No. 11: 1567-1576, 2001.

Poliachik et al., "Effect of High-Intensity Focused Ultrasound on Whole Blood With or Without Microbubble Contrast Agent." *Ultrasound in Medicine & Biology*, vol. 25, No. 6: 991-998, 1999.

Porter et al., "Ultrasound, Microbubbles and Thrombolysis." *Progress in Cardiovascular Diseases*, vol. 44, No. 2: 101-110, Oct. 2001.

Rivens et al., "Vascular Occlusion Using Focused Ultrasound Surgery for Use in Fetal Medicine." *European Journal of Ultrasound*, vol. 9: 89-97, 1999.

Rosen et al., "Vascular Occlusive Diseases." 37pp., revised 2002.

Rosenschein et al., "Shock-Wave Thrombus Ablation, A New Method for Noninvasive Mechanical Thrombolysis." *The American Journal of Cardiology*, vol. 70, Issue 15: Abstract, Nov. 15, 1992.

Rosenschein et al., "Ultrasound Imaging-Guided Nonivasive Ultrasound Thrombolysis-Preclinical Results." *Circulation*, vol. 102: 238-245, 2000. <http://www.circulationaha.com.org>.

Schulte-Altedorneburg et al., "Accuracy of In Vivo Carotid B-Mode Ultrasound Compared with Pathological Analysis: Intima-Media Thickening, Lumen Diameter, and Cross-Sectional Area." *Stroke*, vol. 32, No. 7: 1520-1524, 2001.

Tachibana et al., "Albumin Microbubble Echo-Contrast Material as an Enhancer for Ultrasound Accelerated Thrombolysis." *Circulation*, vol. 92: 1148-1150, 1995.

Tachibana et al., "The Use of Ultrasound for Drug Delivery." *Echocardiography*, vol. 18, No. 4: 323-328, May 2001.

Tardy et al., "In Vivo Ultrasound Imaging of Thrombi Using a Target-specific Contrast Agent." Academy of Radiology, vol. 9, Suppl. 2: S294-S296, 2002.

Vaezy et al., "Acoustic surgery." *Physics World*: 35-39, Aug. 2001.

Vaezy et al., "Hemostasis and Tumor Treatment using High Intensity Focused Ultrasound: Experimental Investigations and Device Development." *First International Workshop on the Application of HIFU in Medicine*: 46-49, 2001.

Vaezy et al., "Hemostasis using high intensity focused ultrasound." *European Journal of Ultrasound*, vol. 9: 79-87, 1999.

Vaezy et al., "Intra-operative acoustic hemostasis of liver: production of a homogenate for effective treatment." *Ultrasonics*, vol. 43: 265-269, 2005.

Von Land et al., "Development of an Improved Centerline Wall Motion Model." *IEEE*: 687-690, 1991.

Watkin et al., "Multi-Modal Contrast Agents: A First Step." *Academy of Radiology*, vol. 9, Suppl. 2: S285-S287, 2002.

Wickline et al., "Blood Contrast Enhancement with a Novel, Non-Gaseous Nanoparticle Contrast Agent." *Academy of Radiology*, vol. 9, Suppl. 2: S290-S293, 2002.

Williamson et al., "Color Doppler Ultrasound Imaging of the Eye and Orbit." *Survey of Ophthamology*, vol. 40, No. 4: 255-267, 1996.

Yu et al., "A microbubble agent improves the therapeutic efficiency of high intensity focused ultrasound: a rabbit kidney study." *Urological Research*, PubMed: Abstract, 2004.

n.a., "Cavitation." Ultrasound TIP—U.S. Database: Dec. 12, 2007.

n.a., "Mechanical Bioeffects in the Presence of Gas-Carrier Ultrasound Contrast Agents." *Journal of Ultrasound & Medicine*, vol. 19: 120-142, 2000.

n.a., "Breast Cancer—Insightec: focused ultrasound for non invasive treatment." FAQ, 2000. <http://www.exablate2000.com/physicians_faq.html>.

Aaslid et al., "Noninvasive transcranial Doppler ultrasound recording of flow velocity in basal cerebral arteries." *Journal of Neurosurgery*, vol. 57: 769-774, 1982.

Bots et al., "Intima Media Thickness as a Surrogate Marker for Generalised Atherosclerosis." *Cardiovascular Drugs and Therapy*, ProQuest Medical Library; vol. 16, No. 4: 341-351, Jul. 2002.

Buller et al., "Accurate Three-dimensional Wall Thickness Measurement From Multi-Slice Short-Axis MR Imaging." *Computers in Cardiology*, 245-248, 1995.

Campbell et al. "Pulsatile Echo-encephalography." *Acta Neurologica Scandinavica Supplementum 45*, vol. 46: 1-57, 1970.

Dahl et al., "Simultaneous Assessment of Vasoreactivity Using Transcranial Doppler Ultrasound and Cerebral Blood Flow in Healthy Subjects." *Journal of Cerebral Blood Flow and Metabolism*, vol. 14, No. 6: 974-981, 1994.

Dempsey et al., "Thickness of Carotid Artery Atherosclerotic Plaque and Ischemic Risk." *Neurosurgery*, vol. 27, No. 3: 343-348, 1990.

Gao et al., "Imaging of the Elastic Properties of Tissue—A Review." *Ultrasound in Medicine & Biology*, vol. 22, No. 8: 959-977, 1996.

Hubka et al., "Three-dimensional echocardiographic measurement of left ventricular wall thickness: In vitro and in vivo validation." *Journal of the American Society of Echocardiography*, vol. 15, No. 2: 129-135, 2002.

Iannuzzi et al., "Ultrasonographic Correlates of Carotid Atherosclerosis in Transient Ischemic Attack and Stroke." *Stroke*, ProQuest Medical Library, vol. 26, No. 4: 614-619, 1995.

Kang et al., "Analysis of the Measurement Precision of Arterial Lumen and Wall Areas Using High-Resolution MRI." *Magnetic Resonance in Medicine*, vol. 44: 968-972, 2000.

Klingelhöfer et al., "Chapter 4: Functional Ultrasonographic Imaging" In Babikian VL, Wechsler LR, eds. *Transcranial Doppler Ultrasonography*. Woburn, MA: Butterworth-Heinemann, 49-66, 1999.

Markwalder et al., "Dependency of Blood Flow Velocity in the Middle Cerebral Artery on End-Tidal Carbon Dioxide Partial Pressure—A Transcranial Ultrasound Doppler Study." *Journal of Cerebral Blood Flow and Metabolism*, vol. 4, No. 3: 368-372, 1984.

O'Leary et al., "Carotid-artery Intima and Media Thickness as a Risk Factor for Myocardial Infarction and Stroke in Older Adults." Car-

(56) References Cited

OTHER PUBLICATIONS diovascular Health Study Collaborative Research Group. *New England Journal of Medicine*, vol. 340, No. 1: 14-22, Jan. 7, 1999.
Pignoli et al., "Intimal plus medial thickness of the arterial wall: a direct measurement with ultrasound imaging." *Circulation*, vol. 74, No. 6:1399-1406, Dec. 1986.
Accord et al., "The Issue of Transmurality in Surgical Ablation for Atrial Fibrillation." *Cardiothoracic Surgery Network*: 3pp, Aug. 8, 2005.
American Red Cross., "Blood 101." 4pp., Dec. 11, 2007.
Anand et al., "Monitoring formation of high intensity focused ultrasound (HIFU) induced lesions using backscattered ultrasound." *Acoustical Society of America*; Mar. 10, 2004.
Anand et al., "Using the ATL 1000 to Collect Domodulated RF Data for Monitoring HIFU Lesion Formation." Presented at SPIE Medical Imaging 2003. 11pp, 2003.
Bachmann et al., "Targeting Mucosal Addressin Cellular Adhesion Molecule (MAdCAM)-1 to Noninvasively Image Experimental Crohn's Disease." *Gastroenterology*; vol. 130: 8-16, 2006.
Bauer et al., "Ultrasound Imaging with SonoVue: Low Mechanical Index Real-Time Imaging." Acad. Radiol.; vol. 9, Suppl. 2: S282-S284, 2002.
Beard et al., "An Annular Focus Ultrasonic Lens for Local Hyperthermia et al., Treatment of Small Tumors." *Ultrasound in Medicine & Biology*; vol. 8, No. 2: 177-184, 1982.
Bokarewa et al., "Tissue factor as a proinflammatory agent." *Arthritis Research*, vol. 4: 190-195, Jan. 10, 2002.
Brayman et al., "Erosion of Artificial Endothelia In Vitro by Pulsed Ultrasound: Acoustic Pressure, Frequency, Membrane Orientation and Microbubble Contrast Agent Dependence." *Ultrasound in Medicine & Biology*; vol. 25, No. 8: 1305-1320, 1999.
Chao et al., "Aspheric lens design." *Ultrasonics Symposium, 2000 IEEE*, vol. 2: Abstract Only, Oct. 2000.
Chen et al., "A comparison of the fragmentation thresholds and inertial cavitation doses of different ultrasound contrast agents." *Journal of the Acoustical Society of America*, vol. 113, No. 1: 643-665, Jan. 2003.
Chen et al., "Inertial Cavitation Dose and Hemolysis Produced In Vitro With or Without Optison." *Ultrasound in Medicine & Biology*, vol. 29, No. 5: 725-737, 2003.
Chong et al., "Tissue Factor and Thrombin Mediate Myocardial Ischemia-Reperfusion Injury." *The Society of Thoracic Surgeons*, vol. 75: S649-655, 2003.
Dayton et al., "The magnitude of radiation force on ultrasound contrast agents." *Journal of the Acoustical Society of America*, vol. 112, No. 5, Part 1: 2183-2192, Nov. 2002.
Ebbini et al., "Image-guided noninvasive surgery with ultrasound phased arrays." *SPIE*, vol. 3249: 230-239, Apr. 2, 1998.
Everbach et al., "Cavitational Mechanisms in Ultrasound-Accelerated Thrombolysis at 1 MHz." *Ultrasound in Medicine & Biology*, vol. 26, No. 7: 1153-1160, 2000.
Ewert et al., "Anti-myeloperoxidase antibodies stimulate neutrophils to damage human endothelial cells." *Kidney International*, vol. 41: 375-383, 1992.
Ganapathy et al., "A New General Triangulation Method for Planar Contours." *Computer Graphics* vol. 16, No. 3:69-75, 1982.
Guzman et al., "Ultrasound—Mediated Disruption of Cell Membranes. I. Quantification of Molecular uptake and Cell Viability. / II. Heterogeneous effects on cells." *Journal of the Acoustical Society of America*, vol. 110, No. 1: 588-606, Jul. 2001.
Hadimioglu et al., "High-Efficiency Fresnel Acoustic Lenses." *Ultrasonics Symposium 1993 IEEE*: 579-582, 1993.
Hatangadi, Ram. "A Novel Dual Axis Multiplanar Transesophageal Ultrasound Probe for Three-Dimensional Echocardiograph." *University of Washington, Department of Sciences and Engineering*, vol. 55-11B: Abstract 1pg, 1994.
Holt et al., "Bubbles and Hifu: the Good, the Bad and the Ugly." *Boston University, Department of Aerospace and Mechanical Engineering*: 120-131, 2002.
Hwang et al., "Vascular Effects Induced by Combined 1-MHz Ultrasound and Microbubble Contrast Agent Treatments In Vivo." *Ultrasound in Medicine & Biology*, vol. 31, No. 4: 553-564, 2005.
Hynynen et al., "Potential Adverse Effects of High-Intensity Focused Ultrasound Exposure on Blood Vessels In Vivo." *Ultrasound in Medicine & Biology*, vol. 22, No. 2: 193-201, 1996.
Idell et al., "Fibrin Turnover in Lung Inflammation and Neoplasia." *American Journal of Respiratory and Critical Care Medicine*, vol. 163: 578-584, 2001.
Indman, Paul. "Alternatives in Gynecology." *Hysteroscopy*, OBGYN.net, 2000. http://www.gynalternatives.com/hsc.html.
Kaczkowski et al., "Development of a High Intensity Focused Ultrasound System for Image-Guided Ultrasonic Surgery." *Ultrasound for Surgery*, 2001. <http://cimu.apl.washington.edu/hifusurgerysystem.html>.
Klibanov et al., "Detection of Individual Microbubbles of an Ultrasound contrast Agent: Fundamental and Pulse Inversion Imaging." *Academy of Radiology*, vol. 9, Suppl. 2: S279-S281, 2002.
Kudo et al., "Study on Mechanism of Cell Damage Caused by Microbubbles Exposed to Ultrasound." *Ultrasound in Medicine & Biology*, vol. 29, Supplement: 4pp, 2003.
Plett, "Ultrasonic Arterial Vibrometry With Wavelet-Based Detection And Estimation", Jan. 1, 2000, retrieved from the Internet: http://myhome.spu.edu/mplett/thesisMelaniPlett.pdf, 260 pages.
Plett et al., "Automated Ultrasonic Arterial Vibrometry: Detection And Measurement", Proceedings Of SPIE, vol. 3982, Apr. 12, 2000, 9 pages.
Plett et al., "In Vivo Ultrasonic Measurement Of Tissue Vibration At A Stenosis: A Case Study", Ultrasound In Medicine And Biology, New York, US, vol. 27, No. 8, Aug. 1, 2001, pp. 1049-1058.
Extended European Search Report for corresponding European Patent Application No. 05858095.2 dated Oct. 20, 2014, 10 pages.

\* cited by examiner

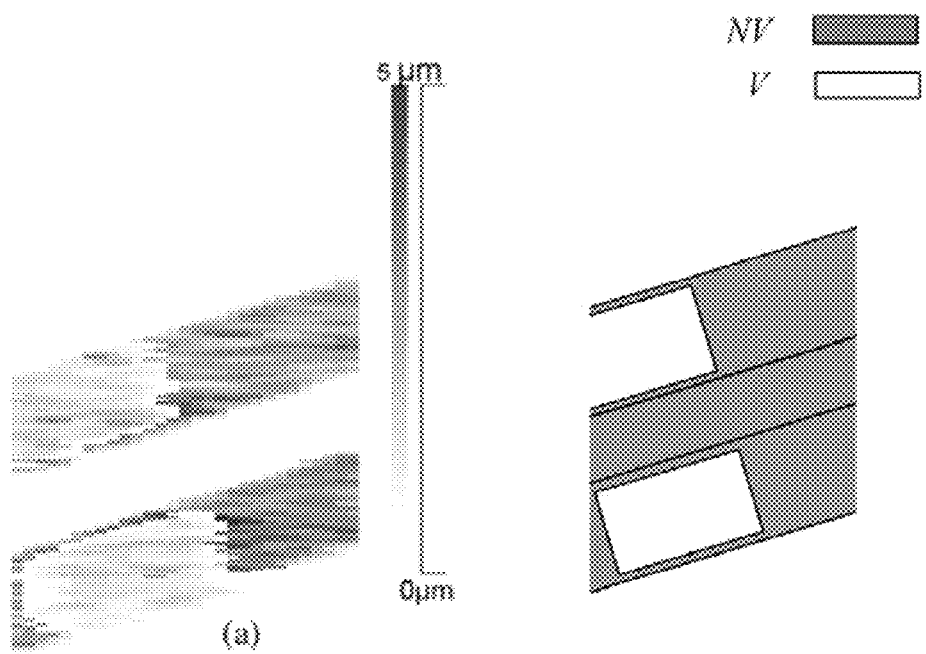
FIG. 12A  FIG. 12B
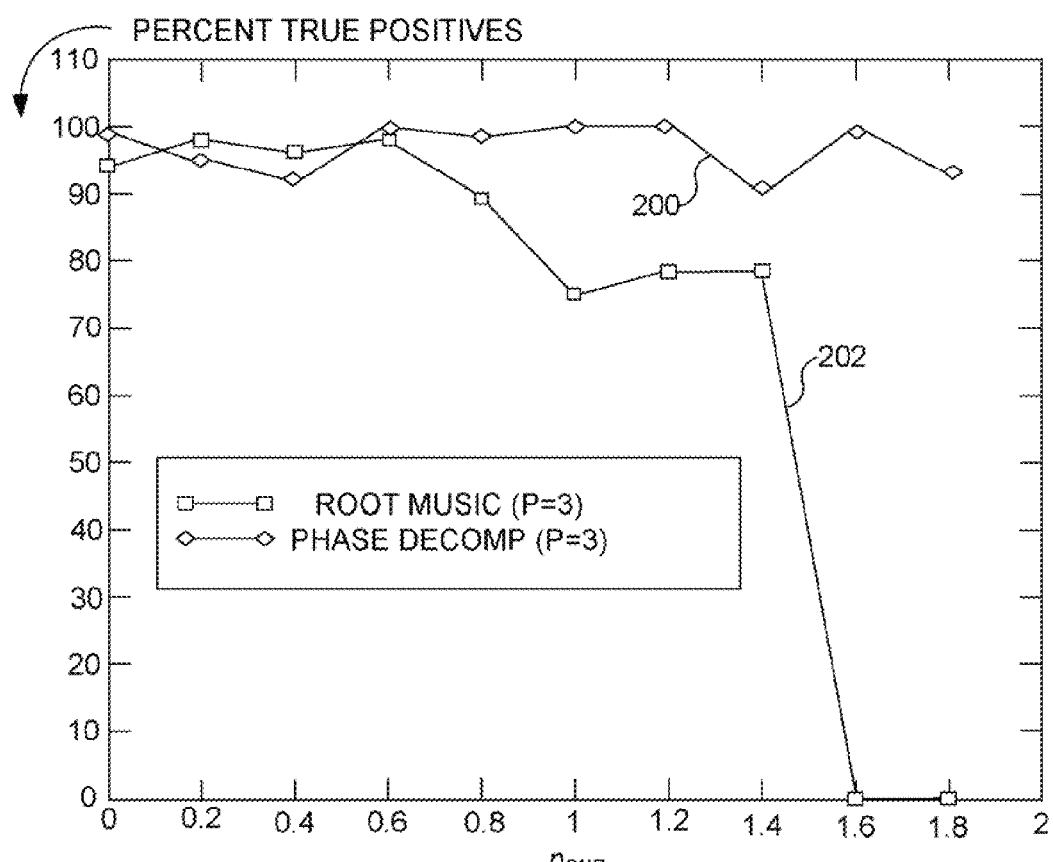
FIG. 14

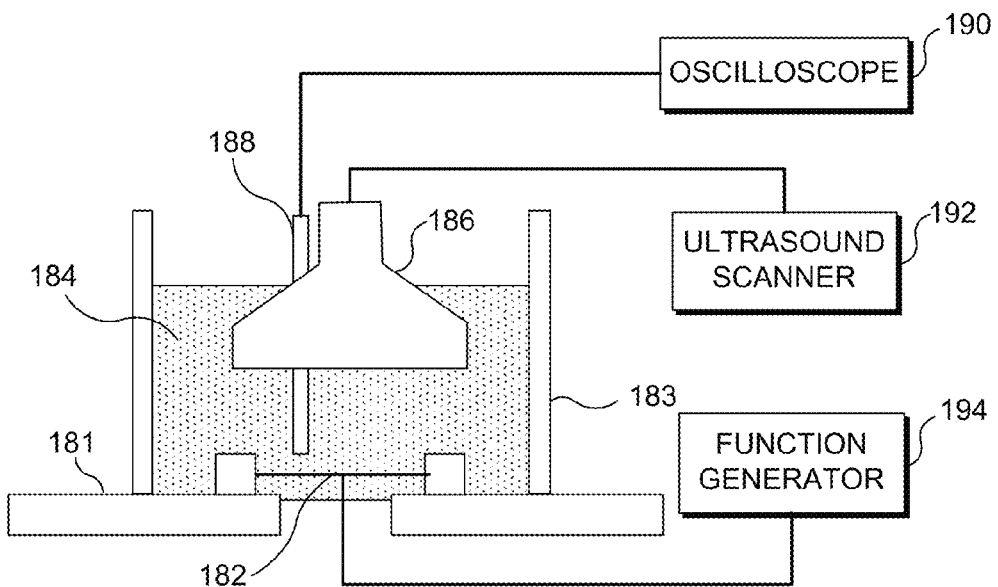
FIG. 15
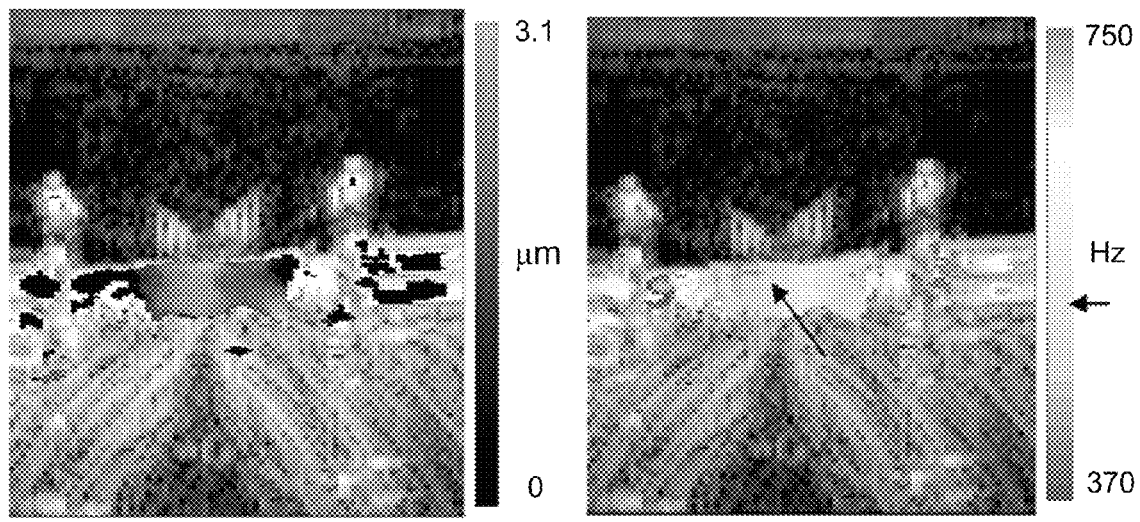
FIG. 16A  FIG. 16B

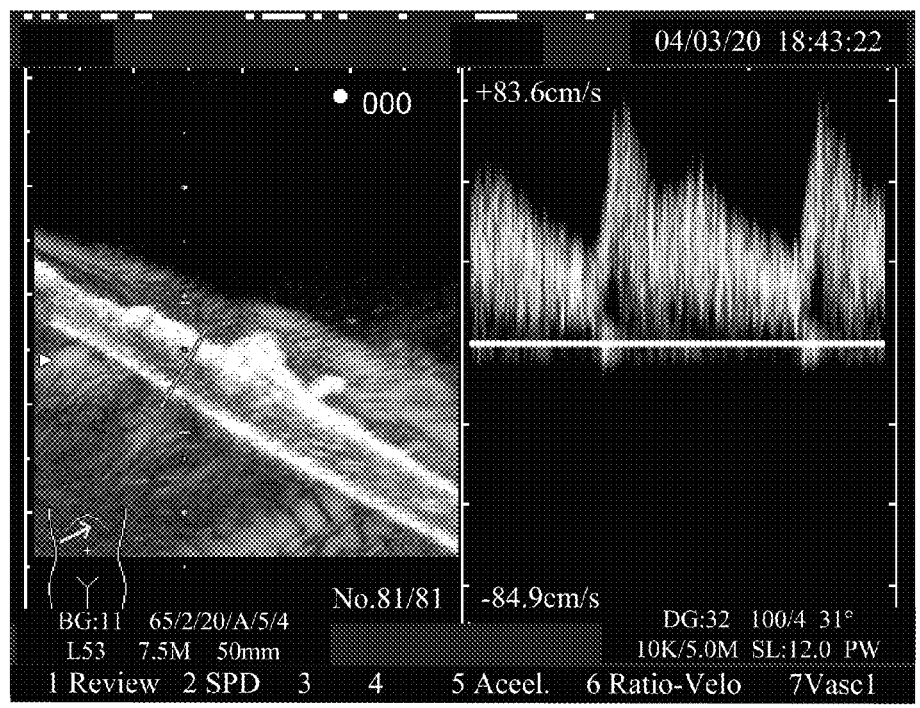
*FIG. 19*
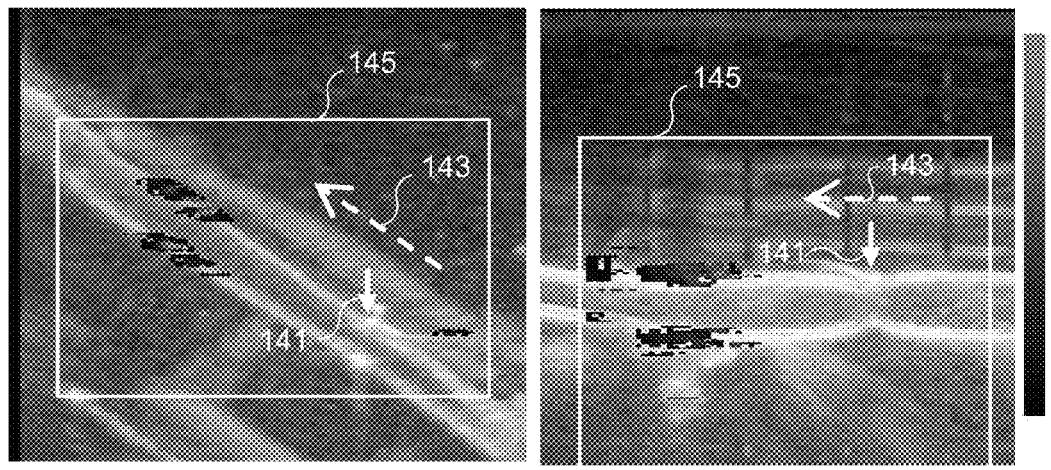
*FIG. 20A*    *FIG. 20B*

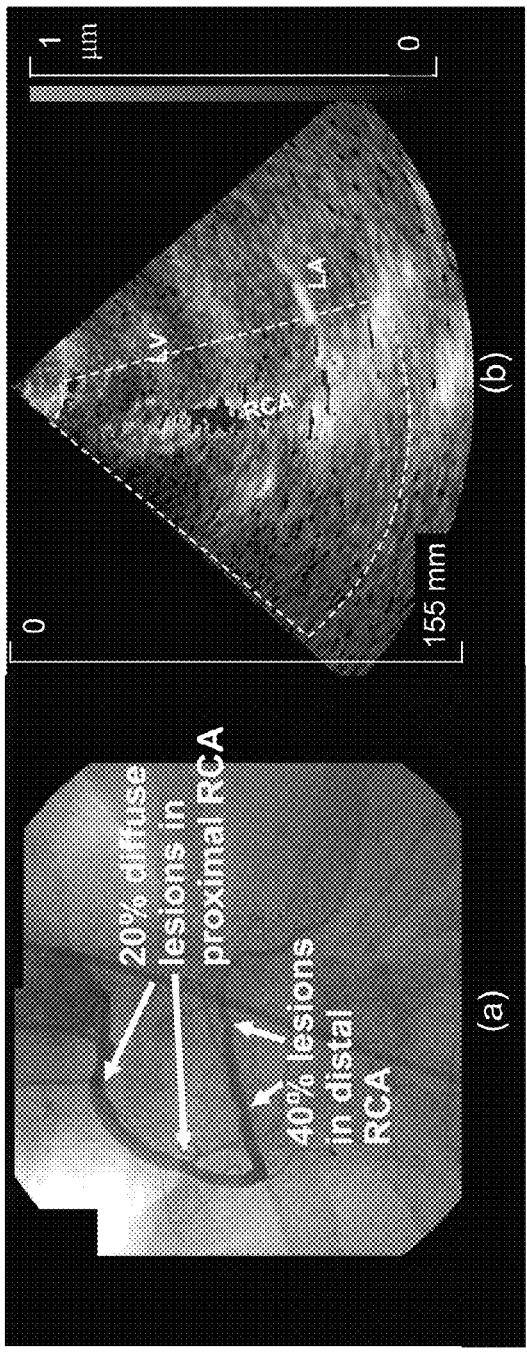
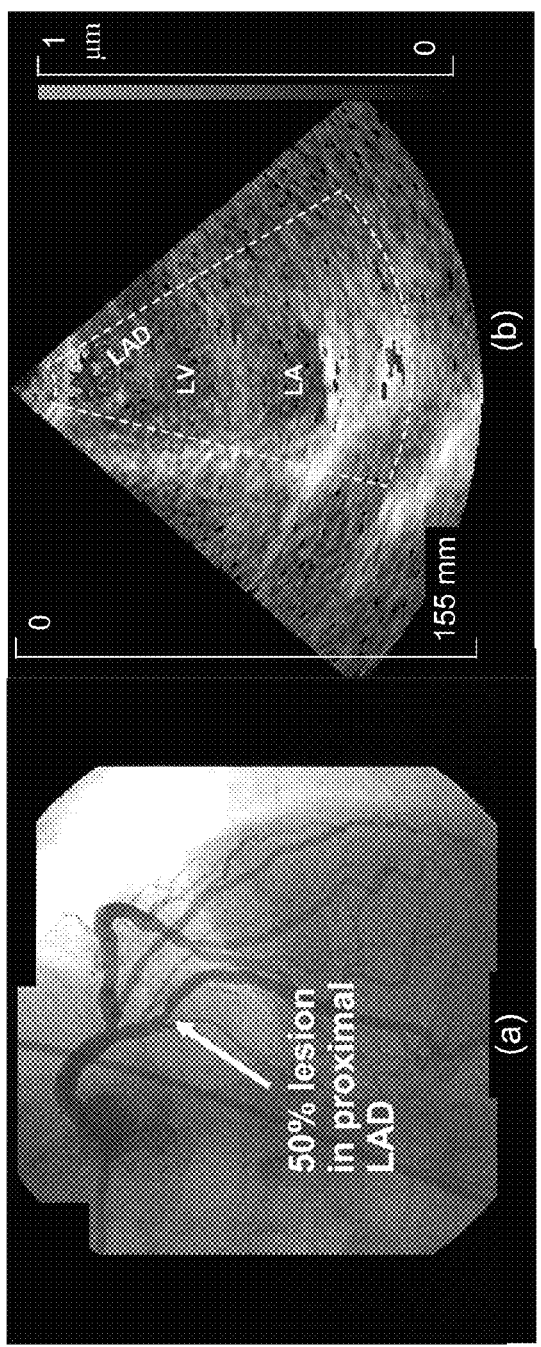
FIGS. 28A-28B
FIGS. 29A-29B

ULTRASONIC TECHNIQUE FOR ASSESSING WALL VIBRATIONS IN STENOSED BLOOD VESSELS

RELATED APPLICATIONS

This application is a continuation-in-part of a copending patent application Ser. No. 11/218,292, filed on Aug. 31, 2005, which itself based on a prior provisional application Ser. No. 60/606,162, filed on Aug. 31, 2004, and a prior copending international application, Serial No. PCT/US2004/032427, filed on Oct. 1, 2004 (designating the United States), the benefits of the filing dates of which are hereby claimed under 35 U.S.C. §119(e) and 35 U.S.C. §120, and under 35 U.S.C. §371.

GOVERNMENT RIGHTS

This invention was made with U.S. government support under Grant No. N00014-01-G-0460 awarded by the U.S. Office of Naval Research (ONR). The U.S. government has certain rights in the invention.

BACKGROUND

For more than two centuries, arterial stenoses have been associated with sounds known as bruits that are audible using a stethoscope. Auscultation (passive listening using a stethoscope) is routinely used to qualitatively assess the loudness and pitch of bruits and murmurs in many vascular diseases, such as renovascular hypertension, coronary artery disease, peripheral artery disease and internal bleeding.

It has now been established that vascular sounds associated with stenoses, aneurysms, arteriovenous fistulae and pseudoaneurysms are produced by the forces exerted on vessel walls by eddies produced when blood flows from a high-pressure region to a low-pressure region through a narrow orifice. The luminal area is reduced by a stenosis; therefore the flow velocity in the throat of the stenosis is increased. This local increase in the flow velocity creates a post-stenotic jet, if the post-stenotic expanse region is not sufficiently streamlined to prevent flow separation (i.e., the stenosis is not a "venturi tube"). Regions of high fluid shear are produced due to the difference in velocity across the boundary of the jet. These shear forces produce eddies in the flow. The presence of eddies cause fluctuations in the flow velocity and pressure in the post-stenotic region, which cause a corresponding motion in the vessel walls. The energy produced by the pressure drop across the stenosis is therefore dissipated through these mechanical vibrations of the vessel wall as well as minor viscous heating of the blood due to turbulent shear fluctuations. The local vibrations in the vessel wall and surrounding tissue manifest either as audible "bruits" and "murmurs" (20 Hz to 1000 Hz) or palpable "thrills" (5 Hz to 20 Hz) when they reach the skin surface. For less severe stenoses, the pressure drop across the stenosis is significant only during the high velocity phase, thus the bruit lasts only during the high velocity phase. For more severe stenoses, the high velocities can be present throughout the cardiac cycle.

The power spectrum of the vibration exhibits a frequency peak called the "break frequency" that is inversely related to the diameter of the orifice and directly related to the local flow velocity through the Strouhal number. Phonoangiography and phonocardiography were developed to quantify the amplitude and duration of bruits and murmurs recorded with a sensitive microphone, and quantitative carotid phonoangiography has been successfully used to measure the spectral content of the bruit signal and estimate the degree of carotid artery stenosis in multiple clinical trials. However, auscultation and phonoangiography lack sensitivity and specificity because they are limited to diagnosing high-intensity vibrations that reach the skin surface, and the origin of the vibrations cannot be clearly resolved. Currently, there is no diagnostic tool to quantitatively image the vibrations associated with bruits at their origin. Therefore, although tissue vibrations have been shown to be important in diagnosis, their clinical use is currently limited. It would be desirable to provide non-invasive techniques for analyzing bruits and wall vibrations associated with stenosed blood vessels that are not limited to analyzing vibrations that reach the skin surface.

Advances in duplex and color-flow ultrasound in the last two decades have had a significant clinical impact on vascular diagnosis, with the simultaneous availability of anatomy and flow images in real time. Ultrasonic tissue Doppler imaging (TDI) has been used for assessment of abnormal wall motion in the cardiac wall as well as in arteries. In conventional color-flow ultrasound images, tissue vibrations from abnormal blood flow produce characteristic artifacts in the surrounding tissue. These artifacts indicate tissue vibrations and are useful for recognizing stenoses. However, they are difficult to interpret, are not quantitative and are rejected by wall filters.

With the introduction of duplex ultrasound, criteria for non-invasive assessment of stenosis severity were developed based upon flow velocity. Although these criteria have been quite useful, such techniques do not analyze the turbulence information present in the wall vibration spectra. It would be desirable to provide non-invasive ultrasound based techniques for evaluating stenosis severity that factor in wall vibrations, as well as flow velocity, to achieve enhanced diagnostic tools.

Accordingly, it would be desirable to develop new tissue vibration detection and imaging modes for ultrasound instruments in which vibrations produced by stenosed blood vessels can be detected and color-coded according to their amplitude and/or frequency. These signals could be displayed separately or overlaid on a B-mode and/or a color-flow image in real time. The tissue vibration-imaging mode might then be used for locating the origin of the vibration more precisely, relative to the patient's anatomy and/or for obtaining simultaneous information about vibrations and the underlying stenosis.

SUMMARY

This application specifically incorporates by reference the disclosures and drawings of each patent application and issued patent identified above as a related application.

Conventional ultrasound imaging (B-mode and Doppler mode imagining) uses sound energy to produce echograms, black and white images based on reflections of sound waves at various tissue interfaces. Stenoses in blood vessels in tissue generate vibrations, which can be difficult to detect from outside the body. The vibrometry techniques disclosed herein direct ultrasound energy at tissue including an artery that may or may not be stenosed. A plurality of samples of reflected ultrasound energy are collected from the tissue. If the tissue is static, there would be no change in those plurality of samples. If the tissue is not static, and all sources of motion other than the stenosis are accounted for, then any changes in the plurality of samples are a function of the stenosis. Thus, analyzing the plurality of samples provides information about the stenosis (i.e., whether the stenosis exists or not, and a relative degree by which the stenosis occludes the arteries, larger vibrations being indicative of larger stenoses). This is somewhat analogous to directing laser energy at a window of a room in which people are speaking, and analyzing changes in the reflection of the laser light (due to the vibration of the window from the voices) to determine what words are being spoken.

The concepts disclosed herein were developed to detect, localize and quantify arterial stenoses by imaging tissue vibrations associated with such stenoses. These vibrations (bruits and murmurs) are sometimes audible using a stethoscope as sounds, or palpable at the skin surface as "thrills," and are indicative of various physiological conditions, including internal bleeding and arterial stenoses. The techniques disclosed herein employ algorithms that process an ensemble of received ultrasound echoes for detecting tissue vibrations, imaging tissue vibrations in a relatively large region of interest, and quantifying the hemodynamic properties of the stenosis based on the measured properties of the tissue vibrations. The algorithms disclosed herein have been implemented in a programmable ultrasound system to study the usefulness of tissue vibrations in real-time localization of stenoses in peripheral arteries and coronary arteries in humans.

In general, the vibration imaging algorithms described herein use an ensemble of ultrasound data acquired during conventional ultrasonic imaging and the clutter signal (which is normally suppressed in conventional color-flow imaging) associated with such data, to detect and characterize tissue vibrations. The term ensemble refers to a series of pulse-echo cycles gathered from the same anatomic region, which, if no motion is present, would be identical, except for noise. It does not refer to data gathered from other locations in 2- or 3-dimensional space or from tissue at a particular spatial location that has moved more than a small fraction of the sample volume during the duration of ensemble acquisition. Various signal processing algorithms have been developed that are suitable for this purpose, including three primary algorithms, based on parametric modeling of vibrations and the criteria to distinguish between clutter, blood flow, and vibrations. A first primary algorithm is based on phase decomposition, a second primary algorithm is based on using an estimation of complex exponentials in noise, and a third primary algorithm is based on autoregressive modeling.

Another set of algorithms utilize a larger ensemble of received ultrasound echoes (typically 64-512) from a small region of interest (e.g., a Doppler range gate) near the site of the stenosis to confirm the presence of tissue vibrations, and to measure the properties of the tissue vibrations with improved accuracy. Various signal processing algorithms have been developed that are suitable for this purpose, including a two-dimensional (2D) Fourier transform utilizing both the slow time variations in the received ultrasound echoes as a result of motion, as well as variation in the motion of tissue at neighboring locations along the direction of the ultrasound beam. A first algorithm for identifying vibrations is based on the 2D Fourier transform of the quadrature-demodulated received echo and utilizes the Radon transform to identify spectral peaks corresponding to vibrations. A second algorithm for identifying vibrations utilizes a multi-frequency average to identify spectral peaks corresponding to vibrations, and to suppress other sources of noise. A method for localizing and grading arterial stenoses using such algorithms is further disclosed herein.

Also disclosed herein is a new tissue vibration imaging mode for ultrasound instruments in which soft-tissue vibrations produced due to the impact of blood flow eddies are detected and color-coded according to their amplitude and frequency, and overlaid on the B-mode and/or color-flow image in real time. The tissue vibration imaging mode can be used for locating the origin of vibration more precisely relative to the anatomy, and/or for obtaining simultaneous information about vibrations and the underlying blood flow.

Real-time tissue vibration imaging has been implemented at an exemplary (but not limiting) frame rate of 10 frames/second, on an ultrasound system with a software-programmable signal and image processing back-end. The preliminary results confirm that vibrations produced as a result of arterial stenoses can be detected and imaged using such techniques. The vibration amplitude is expected to be the largest near a site downstream of the stenosis, and this fact can be used to localize a stenosis quickly and non-invasively. The strong backscattered ultrasonic echoes from tissue vibrations can improve detection of stenoses that are otherwise hard to detect using Doppler blood velocity-based methods due to weak scattering from blood, or because the vessel lumen cannot be resolved by the ultrasound system. This latter point is very significant, as the vibrometry technique disclosed herein can detect stenoses in arteries that cannot be visualized using B-mode or Doppler mode ultrasound imaging.

Potentially, this new tissue vibration imaging technology could be useful in a variety of devices and clinical settings. For example, a low-cost portable screening device with tissue vibration detection functionality could be beneficially employed by general practitioners for diagnosing and/or screening patients with coronary and peripheral artery disease, or by paramedics and trauma centers to evaluate patients with chest pain. In addition, a tissue vibration imaging mode on high-end ultrasound systems can augment duplex ultrasound for enhanced diagnostic capability, which could be beneficially employed by imaging centers, cardiology clinics, and hospitals for diagnosing stenoses in patients. The detected tissue vibrations indicative of a stenosis could be presented as an audible signal in a manner recognizable to a person trained to listen to bruits using a stethoscope or as a palpable signal recognizable to a person trained to detect palpable thrills. Either of these signals could be presented to a local expert in real time, or recorded and presented at a later time, or transmitted to a remote expert for "telediagnosis."

One aspect of the concepts disclosed herein is directed to a method for detecting and localizing arterial stenoses using an ensemble of ultrasound data by detecting and characterizing tissue vibrations caused by blood flow eddies downstream of a stenosis. The method includes the step of processing an ensemble of ultrasound data to produce a tissue motion spectrum signal of a site being imaged. The tissue motion spectrum signal is then processed to produce a tissue vibration signal, from which any contribution to the tissue motion from a source other than vibrations at the stenosis has been substantially minimized. A vibration image is displayed using the tissue vibration signal and indicates a location of the stenosis at the site.

One approach for processing the ensemble of ultrasound data comprises the steps of estimating a correlation matrix from the ultrasound data, and carrying out an eigen decomposition of the correlation matrix to identify a signal subspace and a noise subspace. A frequency of the dominant vibration components in the signal subspace and the noise subspace is then estimated, and based upon that estimate, a vibration amplitude estimate and a vibration frequency estimate are determined. At least one of the vibration amplitude estimate and the vibration frequency estimate comprises the tissue vibration signal.

A second approach for processing the ensemble of ultrasound data for imaging vibrations associated with stenoses includes the step of computing the coefficients of an autoregressive model of an ensemble of received ultrasound echoes. Linear prediction filter coefficients are computed from the coefficients. A power spectrum is estimated, and the peaks in the power spectrum are detected. Based upon the estimate of the power spectrum and the peaks, a vibration amplitude estimate and a vibration frequency estimate are determined. At least one of the vibration amplitude estimate and the vibration frequency estimate again comprises the tissue vibration signal.

In yet another approach for processing the ensemble of ultrasound data, a mean clutter velocity is estimated from the ultrasound data using autocorrelation. The ensemble of ultrasound data is down-mixed with the mean clutter velocity, producing a down-mixed signal. A phase of the down-mixed signal and a mean phase of the down-mixed signal are determined, and the mean phase is subtracted from the phase of the down-mixed signal, producing a residual phase. The residual phase is then decomposed into its dominant components. By applying energy and frequency thresholds, any contribution to the tissue vibration due to noise and blood flow are substantially suppressed, yielding an estimate of vibration amplitude and vibration frequency of tissue at a site.

The step of decomposing the residual phase preferably comprises the steps of estimating a correlation matrix from the residual phase, and performing an eigen decomposition of the correlation matrix to determine the dominant components.

The step of filtering preferably comprises the step of filtering out frequencies equal to the cardiac frequency and several harmonics of the heart rate, and also preferably includes the step of filtering out noise at frequencies that are substantially higher than an expected frequency range of tissue vibrations corresponding to the stenosis at the site. This step also encompasses differentiating between blood flow and tissue vibrations, by utilizing the statistical properties of the signals, the greatest being that the amplitude of the blood signal is about 60 dB lower than the amplitude of the vibration signal, and that the velocity integral of the blood signal over the cardiac cycle does not equal zero while the velocity integral of the tissue signal over the cardiac cycle does equal zero.

The step of displaying the vibration image may comprise the step of displaying at least one of a vibration amplitude image and a vibration frequency image of the site. The method can include the step of displaying the vibration image in connection with an underlying anatomy of the site (i.e., the B-mode grayscale image), substantially in real time.

Another aspect of the present invention is directed to apparatus for detecting and localizing arterial stenoses using an ensemble of ultrasound data. The apparatus includes an ultrasound transducer for transmitting ultrasound pulses toward the internal site and receiving ultrasound data from scatterers at the internal site, including tissue that is vibrating due to a stenosis. In one embodiment, a front-end system controls the ultrasound pulses produced by the ultrasound transducer and demodulates the echoes received by the ultrasound transducer, producing a signal having both in-phase and quadrature components. The apparatus also includes a back-end system to receive the signal from the front-end system and a tissue vibration processor. The front and back-end systems can optionally be combined into a single unit, or one or more parts of these systems can be operating remotely from other parts of the systems. The tissue vibration processor processes the ultrasound signal to estimate tissue vibrations caused by a stenosis, producing a tissue vibration signal. In one embodiment, the tissue vibration signal is converted to an image signal by the back-end system. A display is coupled to the back-end system to receive the image signal, to display a tissue vibration image in which a stenosis at the internal site is indicated. Optionally, the display could be remote from the tissue vibration detection and identification apparatus. For example, the display can be physically located in a hospital, while the tissue vibration detection and identification apparatus is physically located at another location, such as in an ambulance carrying a patient on which the apparatus is being used. Also, instead of a visible display, the result of tissue vibration detection and identification can be presented as an audible or a palpable output indicating tissue vibrations. The tissue vibration signal can also be interpreted by an automated algorithm to indicate a stenosis, and the result of the automated interpretation can be presented as an electronic readout. Generally, the functions performed by the apparatus are consistent with the steps of the method described above.

Significantly, the concepts disclosed herein can be used to generate a vibrometry image of blood vessels that are too small to be imaged using B-mode ultrasound or Doppler mode ultrasound. Thus, one aspect of the concepts disclosed herein is to detect stenoses in arteries that cannot be visualized using B-mode ultrasound or Doppler mode ultrasound. The vibrometry processing is implemented generally as discussed above.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figures 5A, 5B:
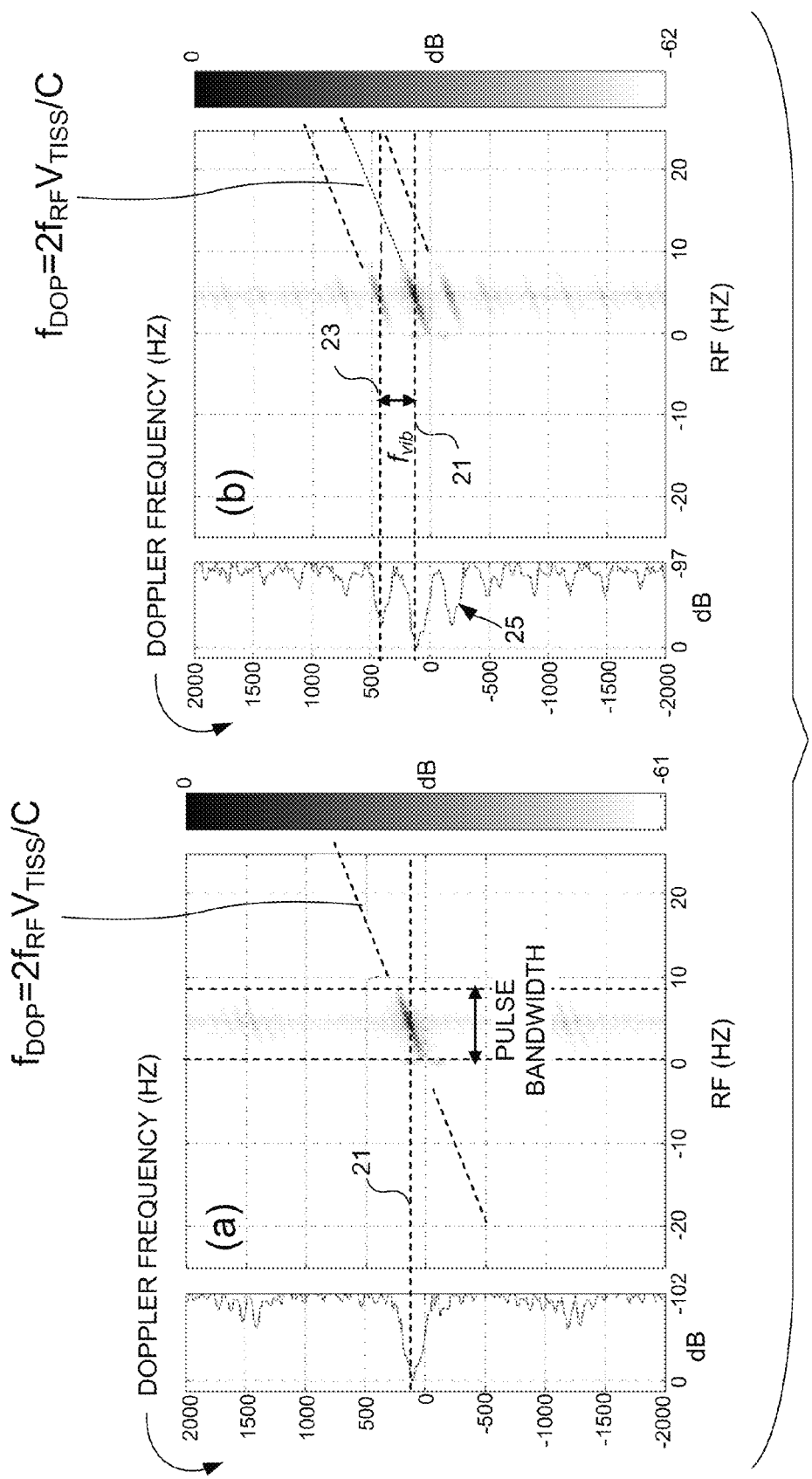
Figures 6A, 6B:
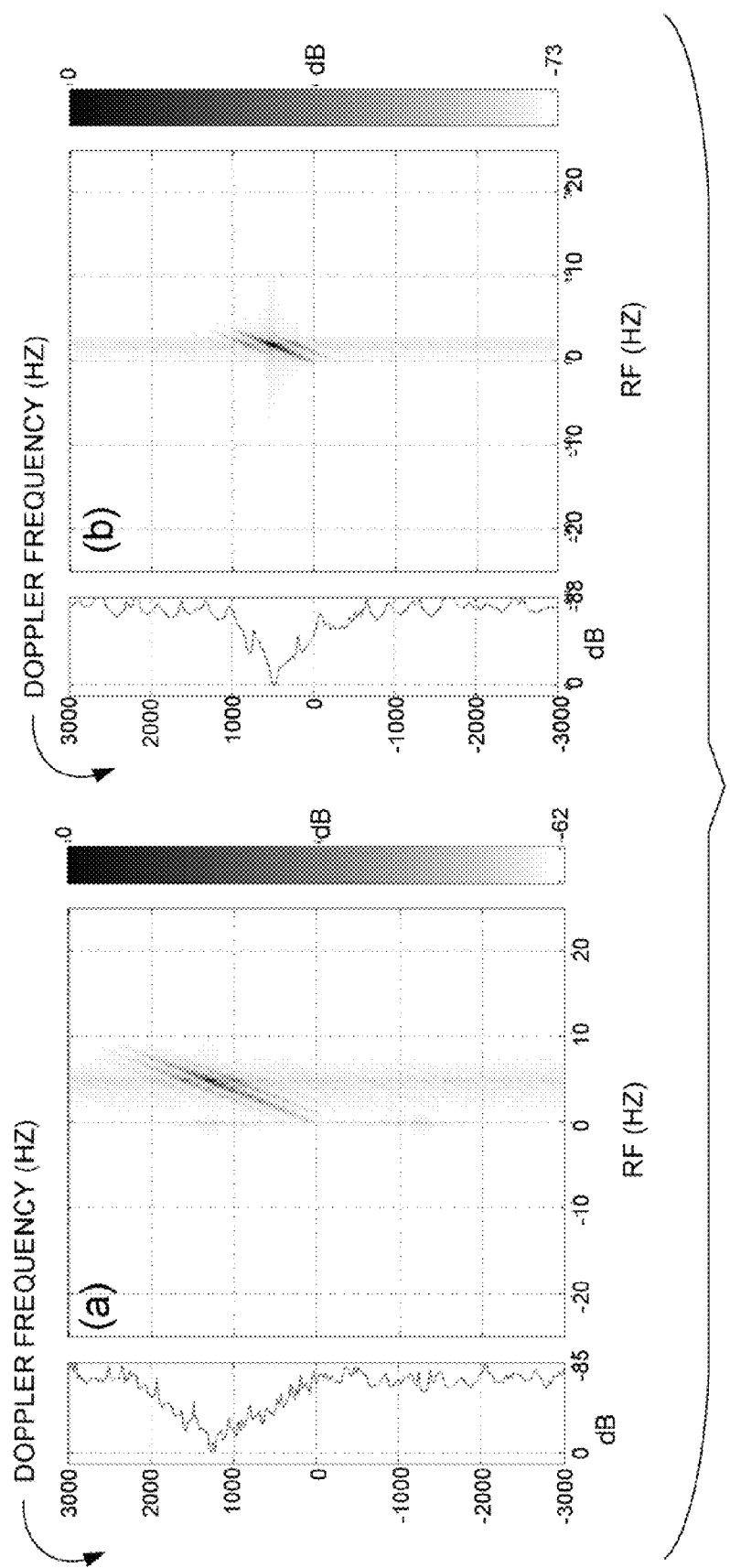
Figures 7A, 7B:
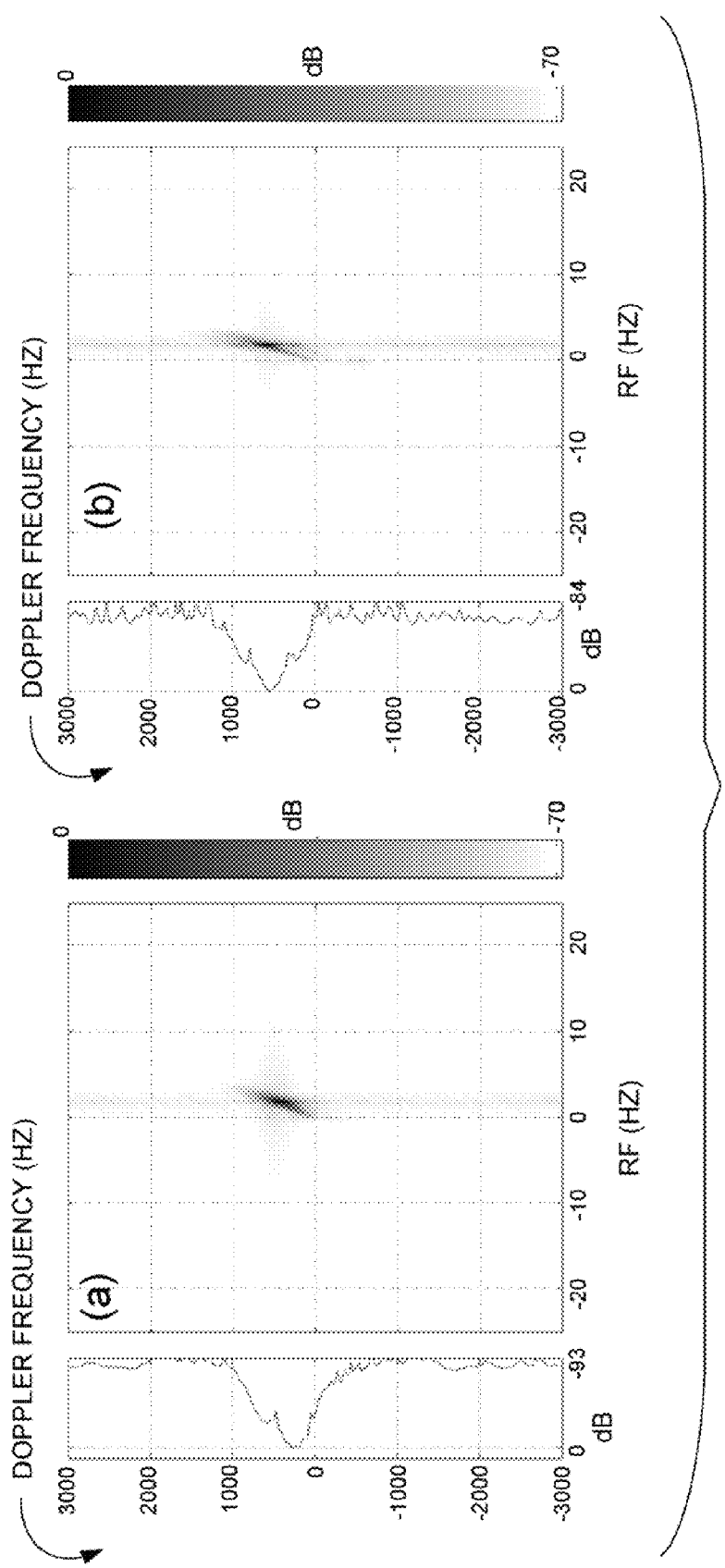
Figures 8A, 8B:
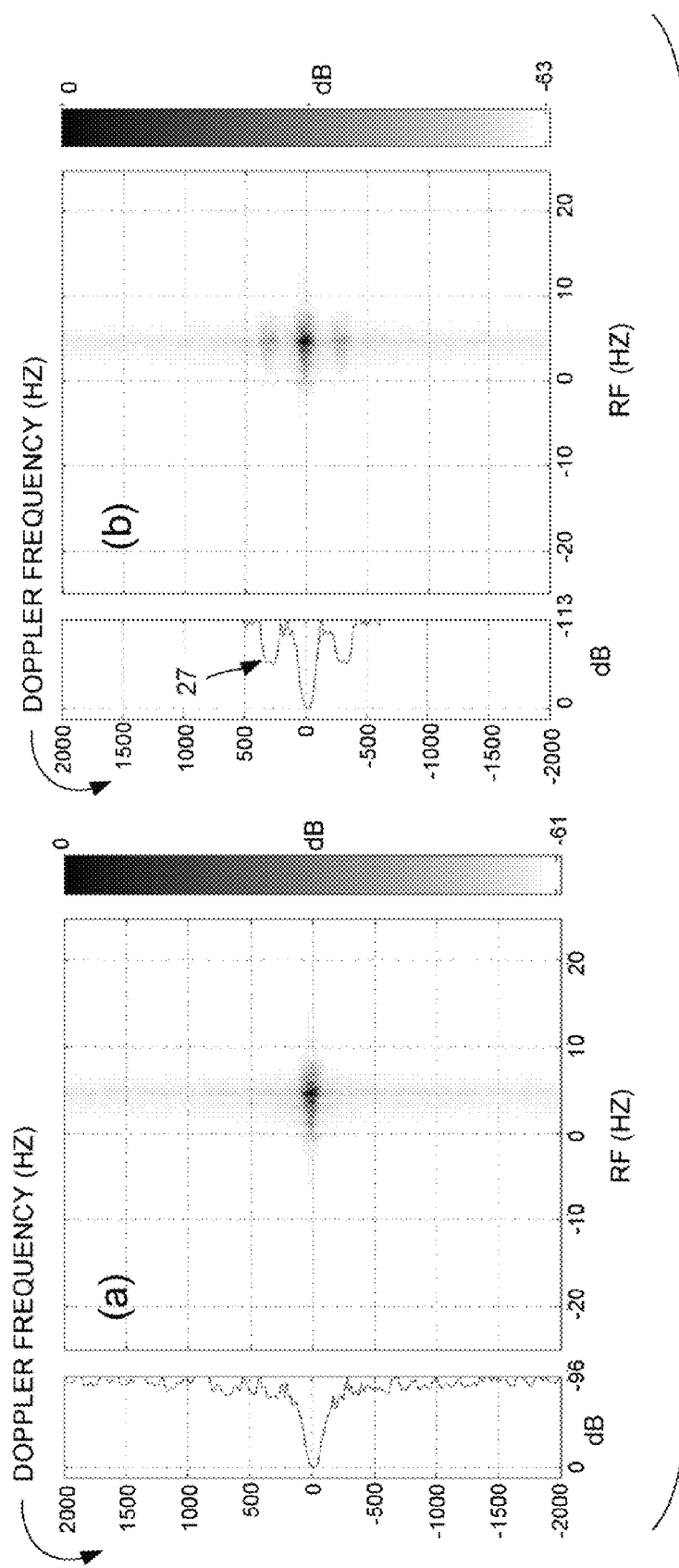
Figure 9A:
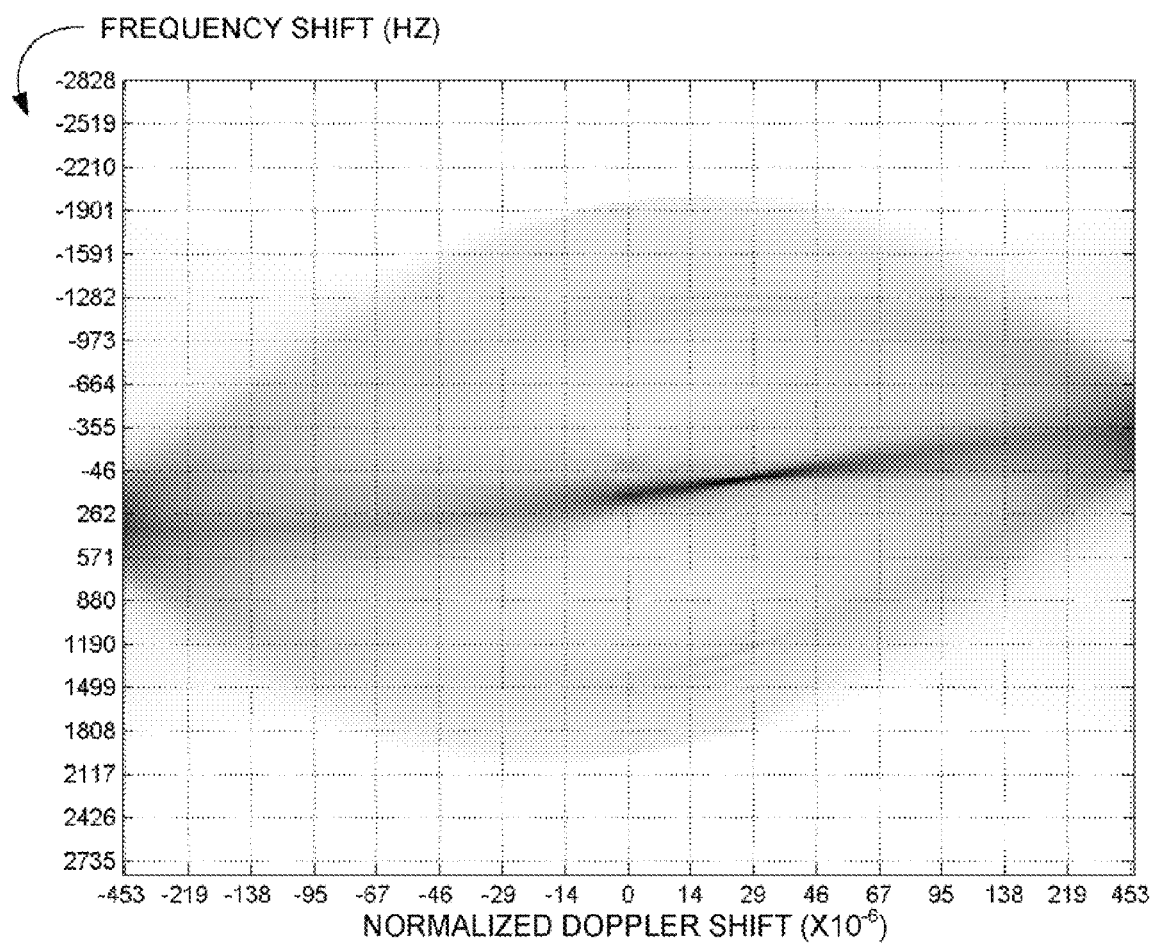
Figure 9B:
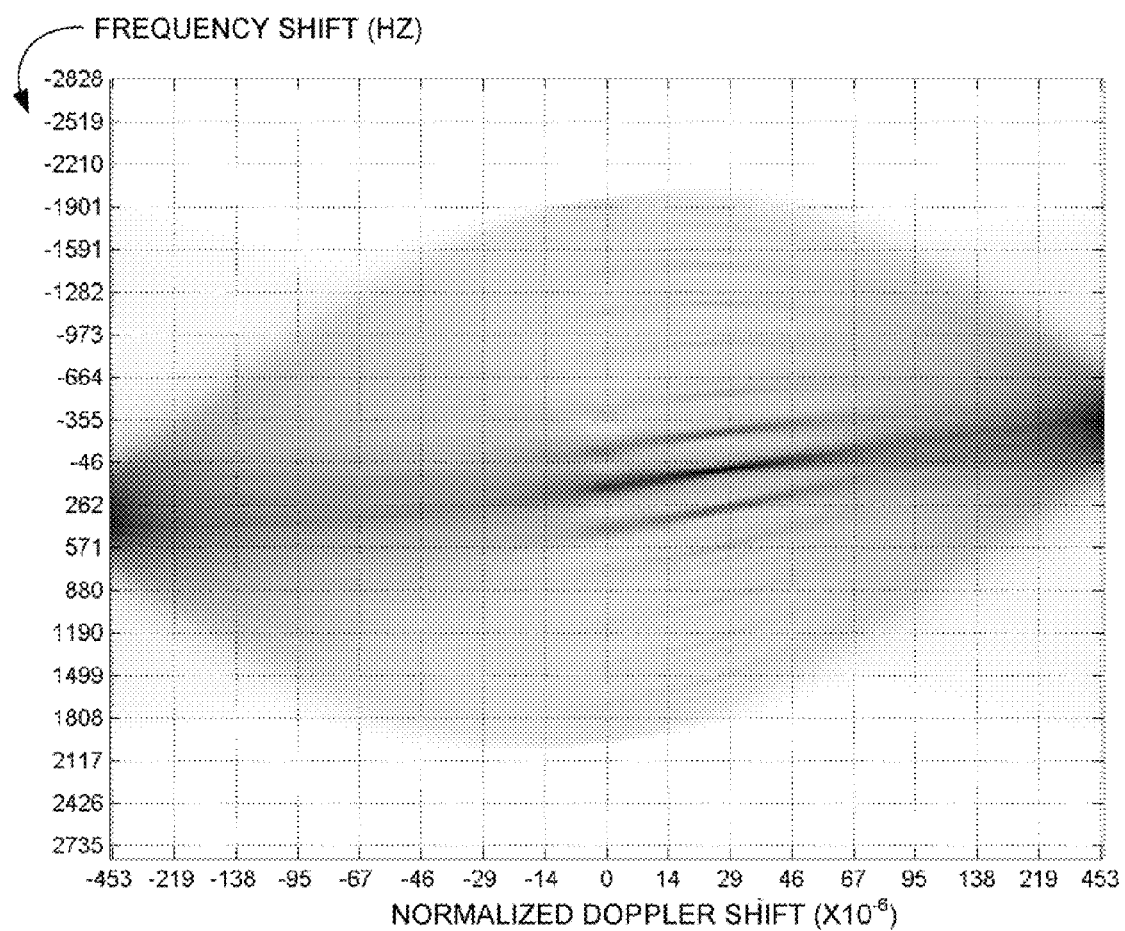
Figure 9C:
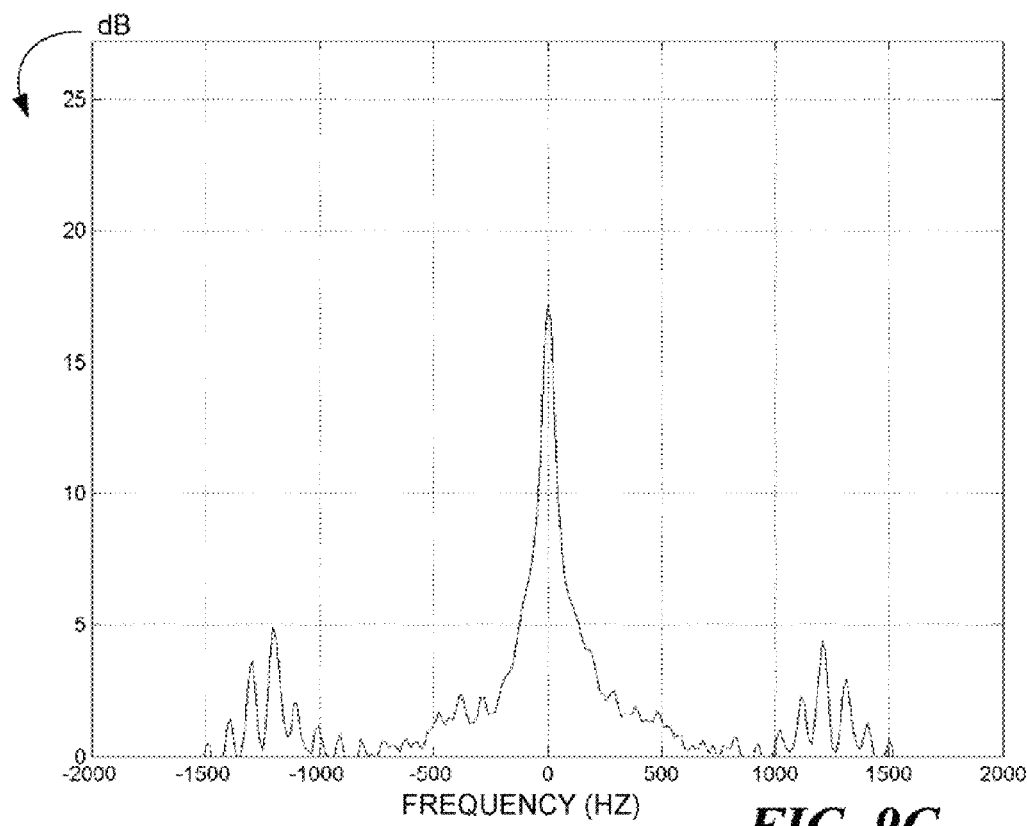
Figure 9D:
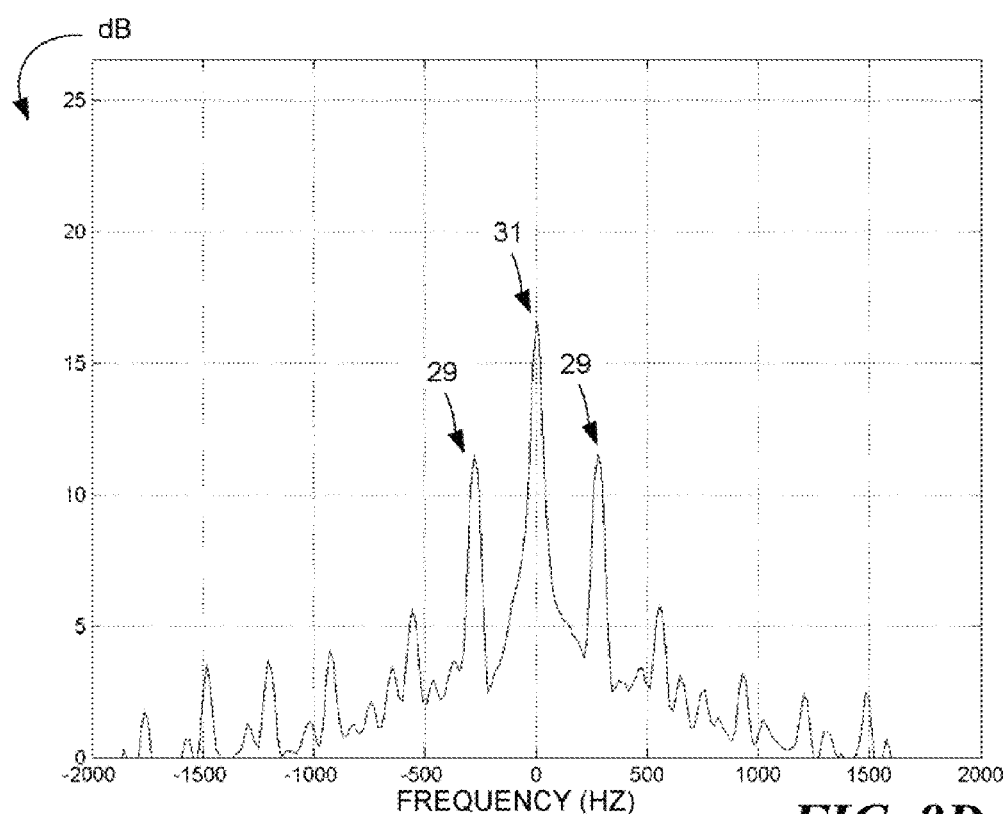
Figure 10A:
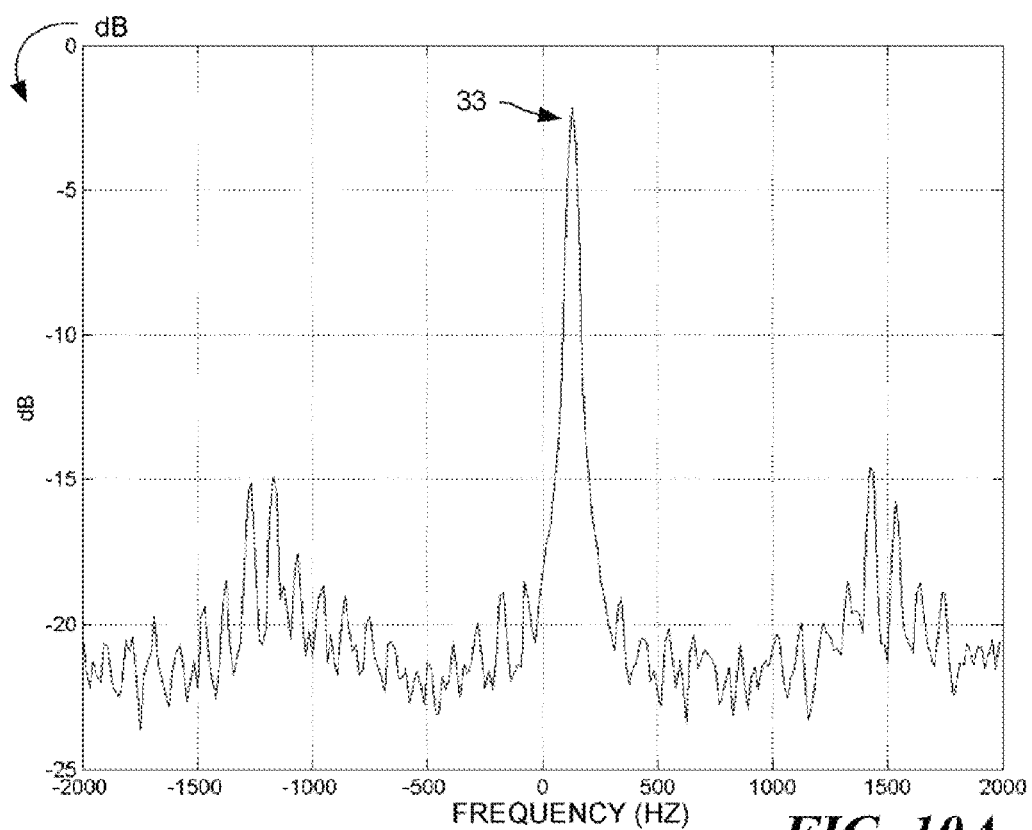
Figure 10B:
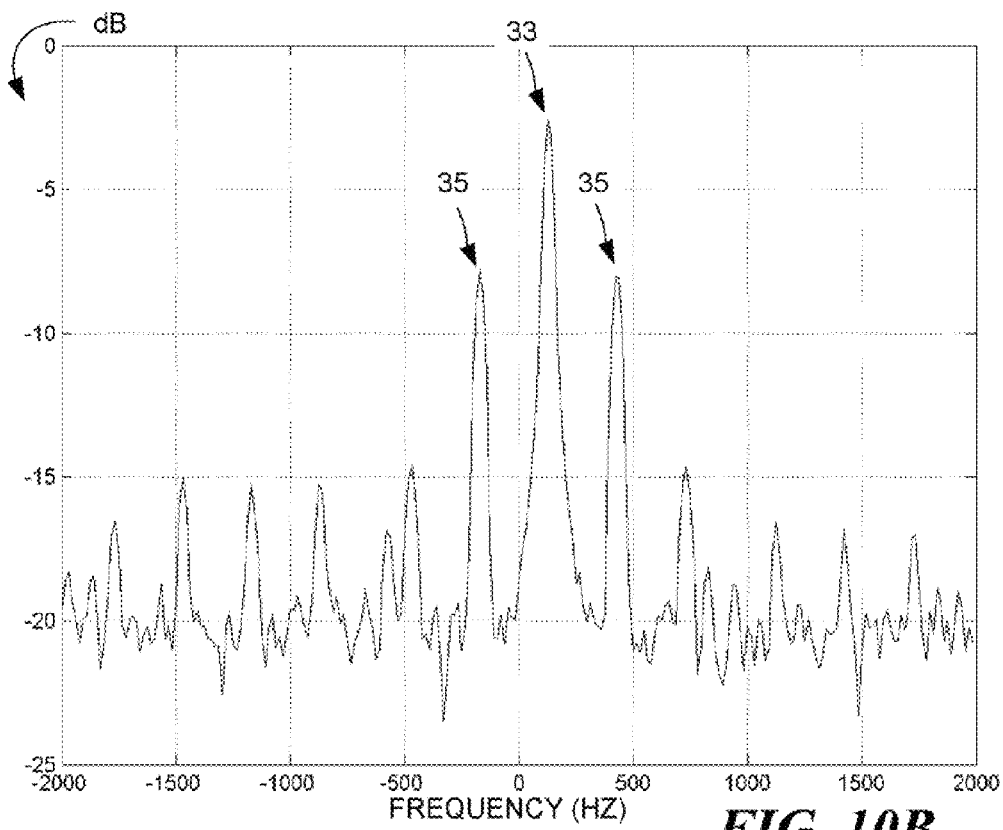
Figure 11A:
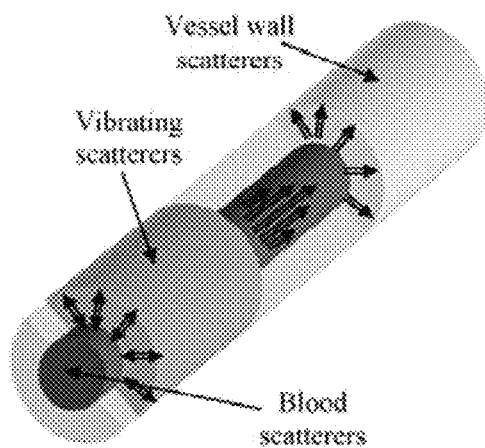
Figure 11B:
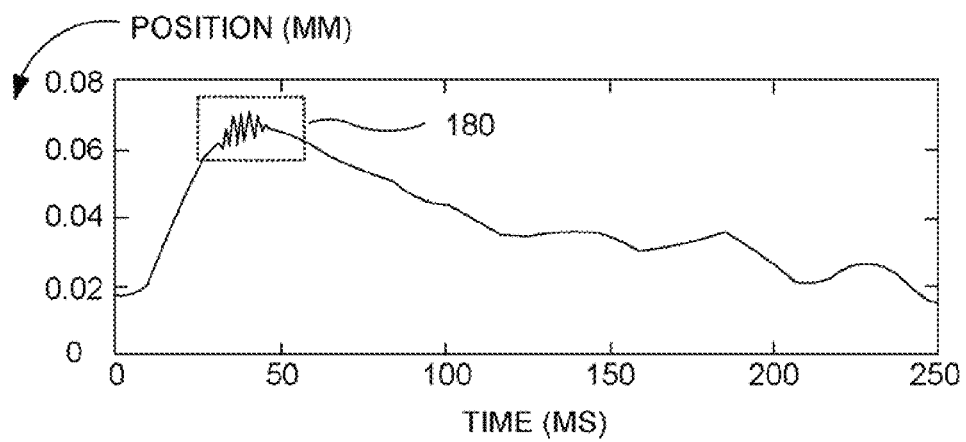
Figure 11C:
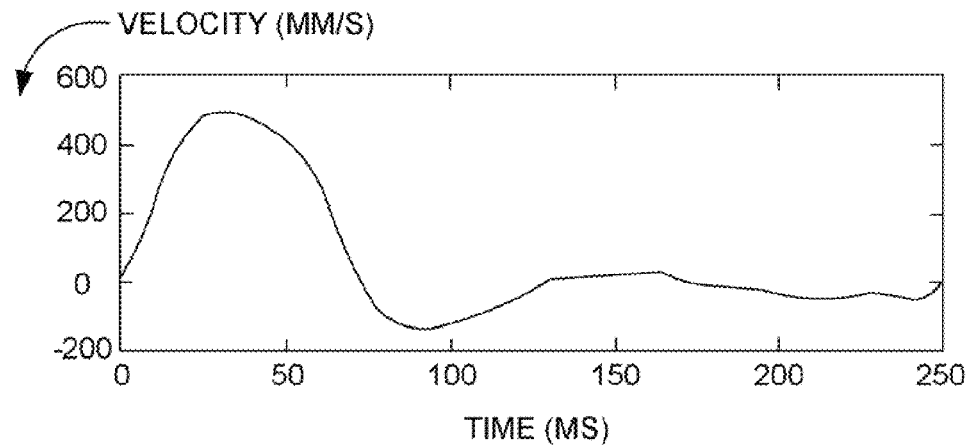
Figure 13A:
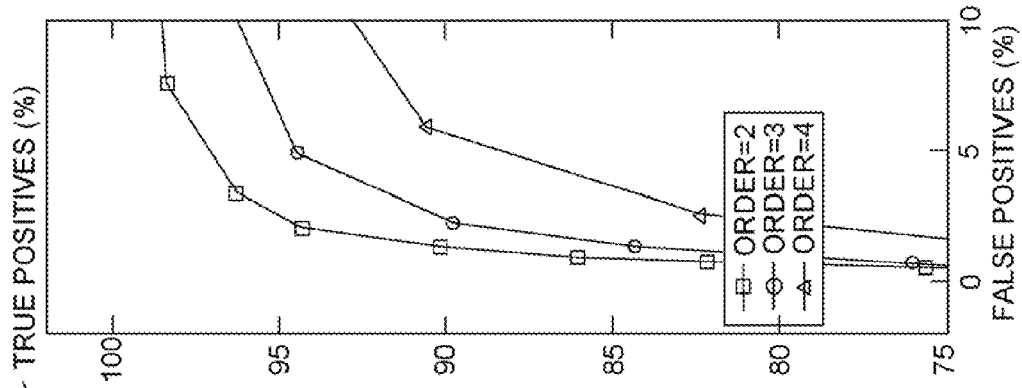
Figure 13B:
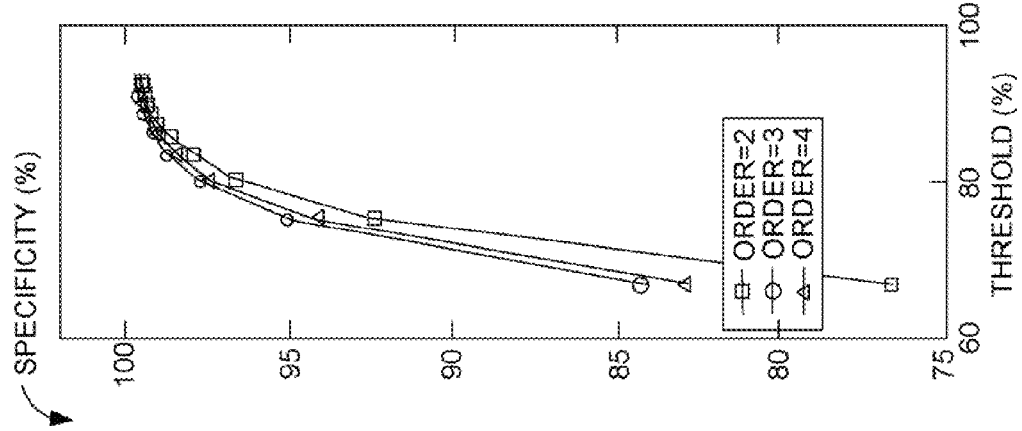
Figure 13C:
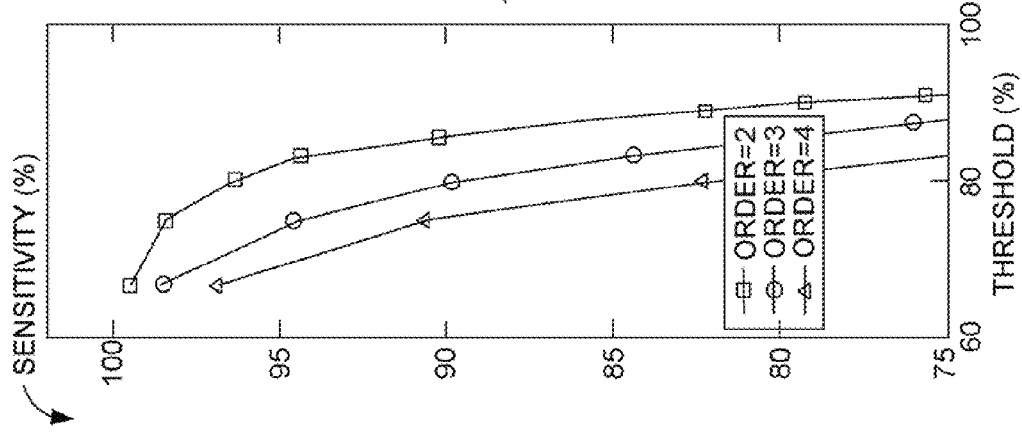
Figure 13F:
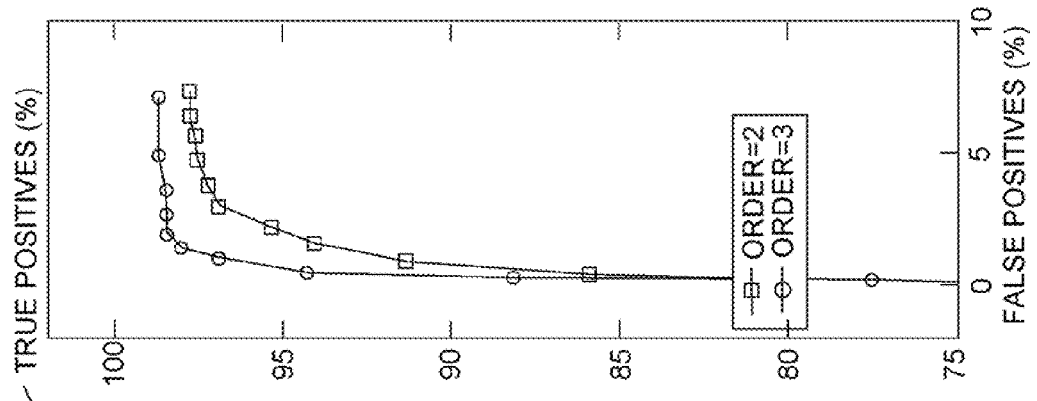
Figure 13E:
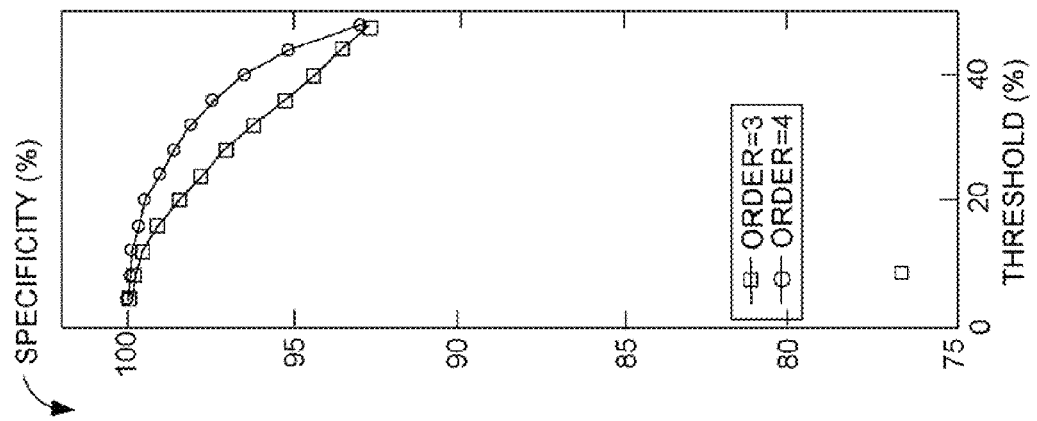
Figure 13D:
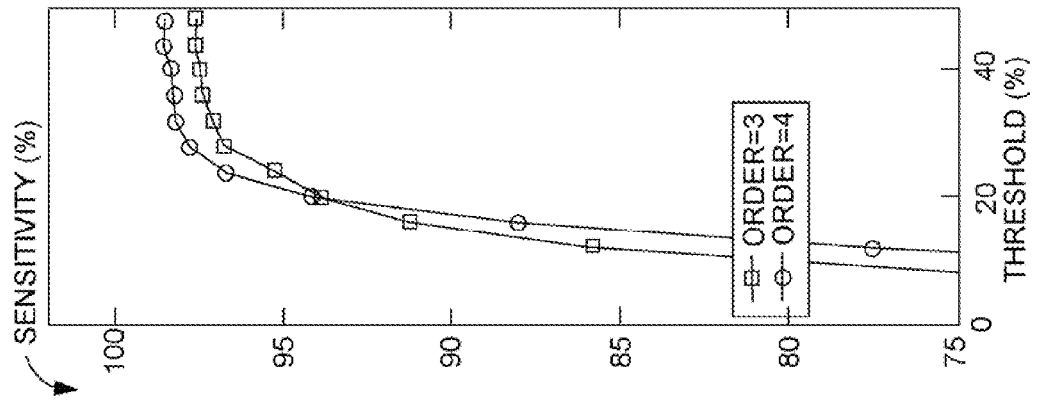
Figure 16C:
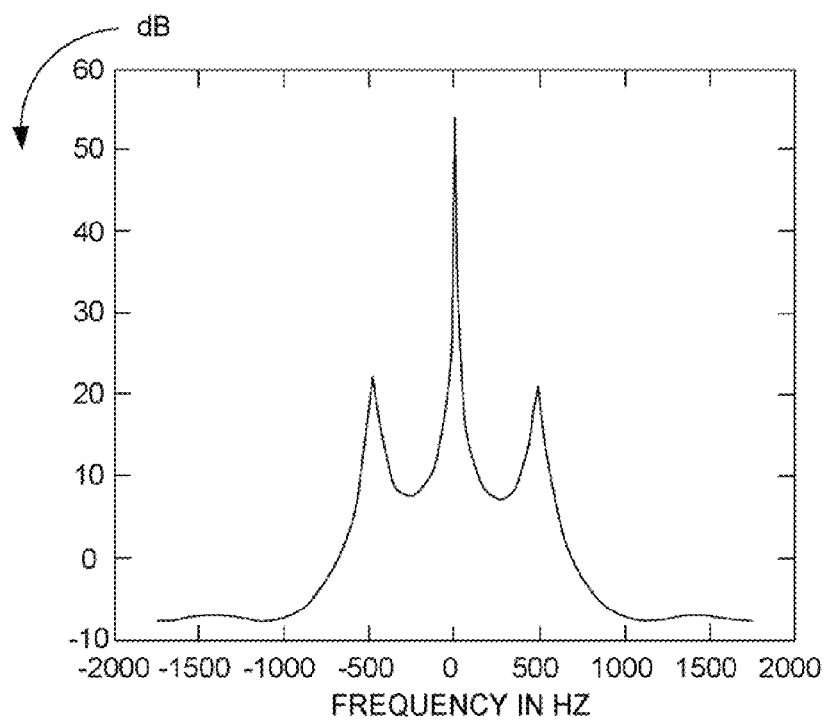
Figure 17A:
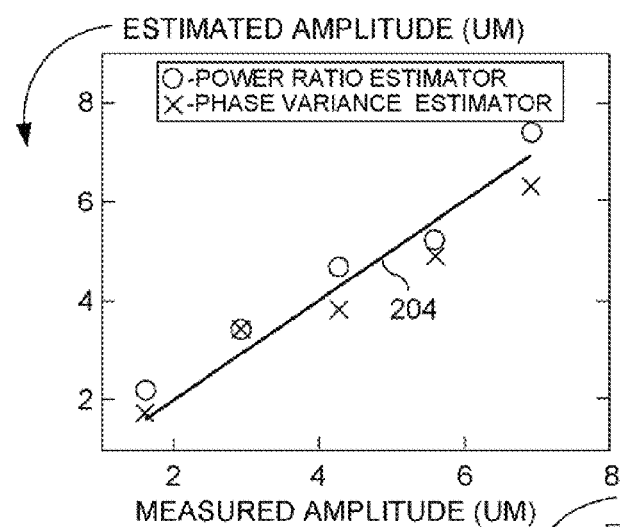
Figure 17B:
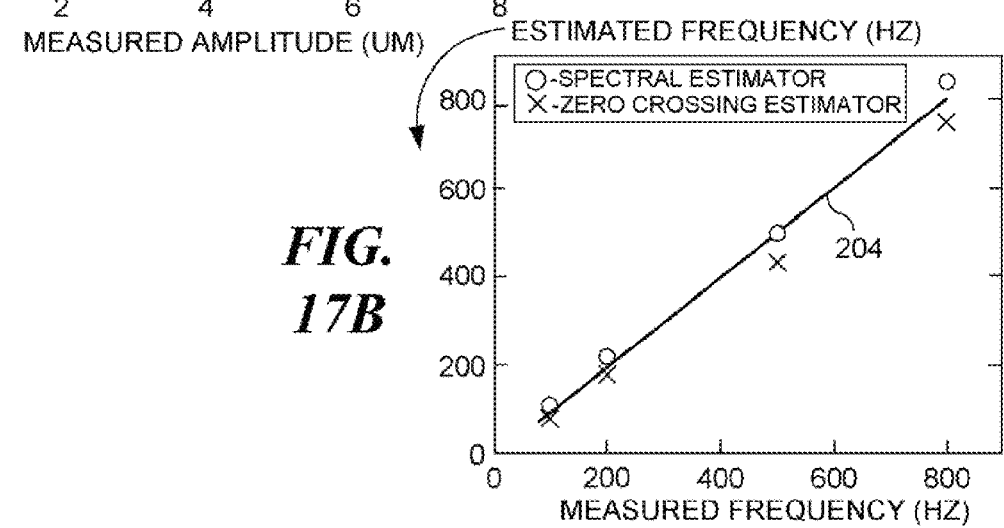
Figure 17C:
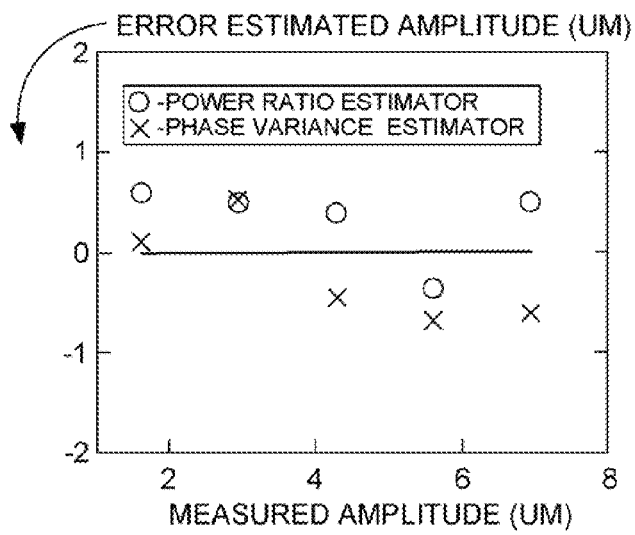
Figure 17D:
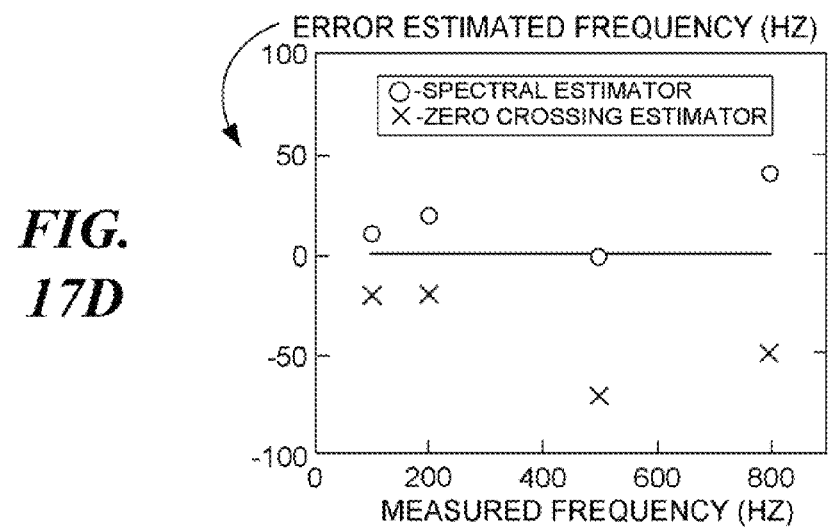
Figure 18:
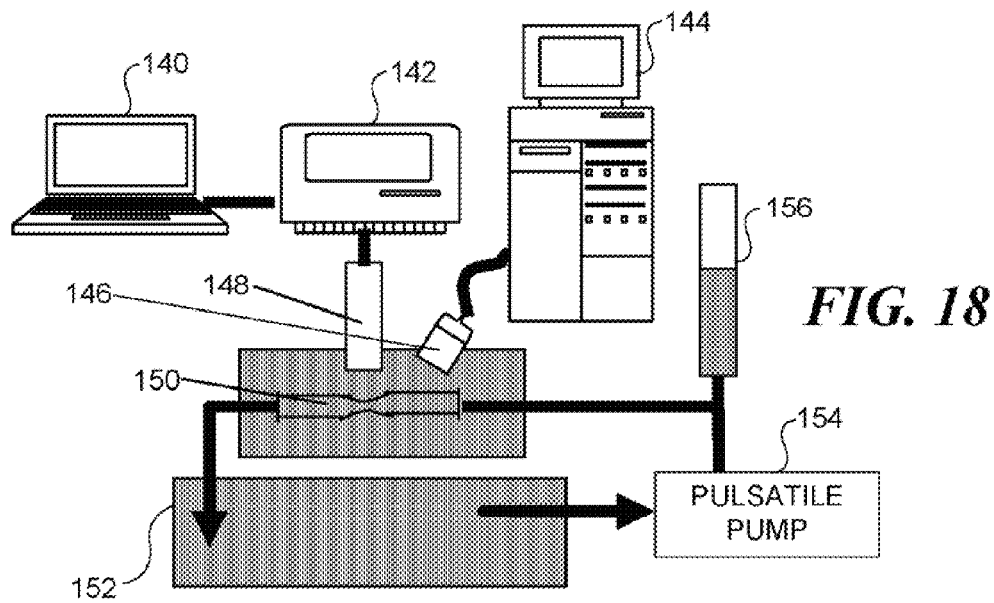
Figure 21:
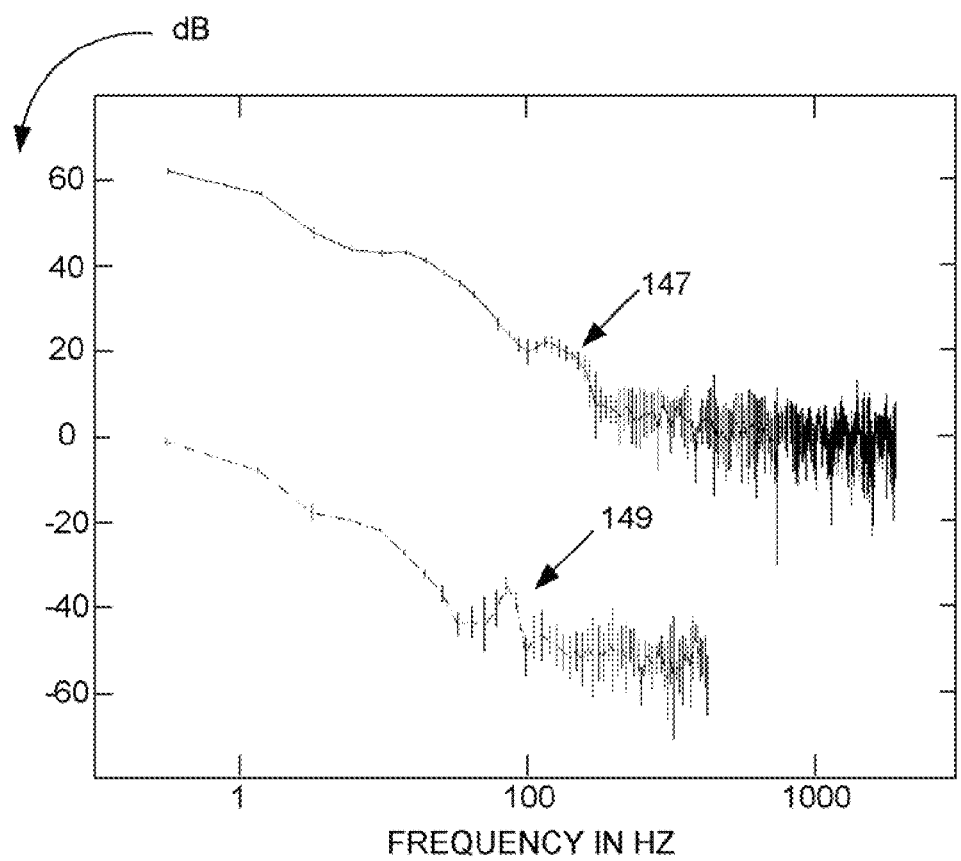
Figures 22A, 22B:
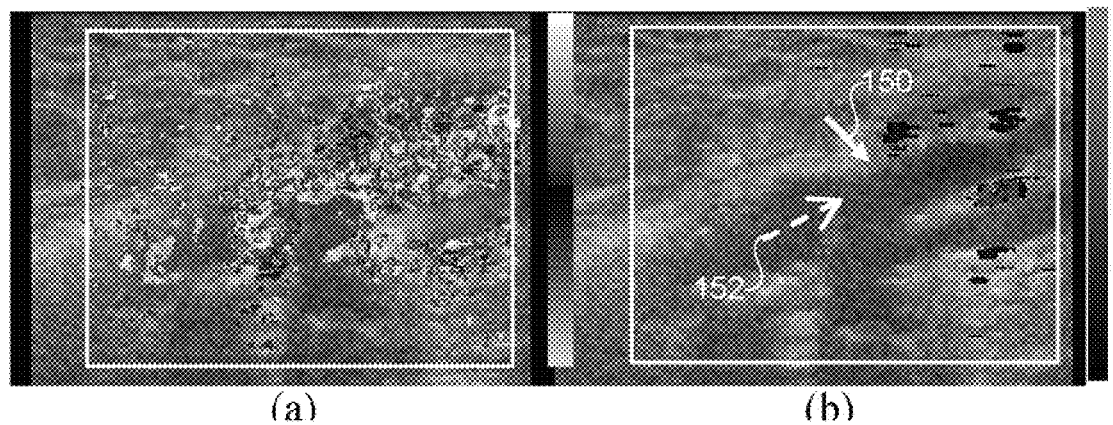
Figures 23A, 23B, 23C:
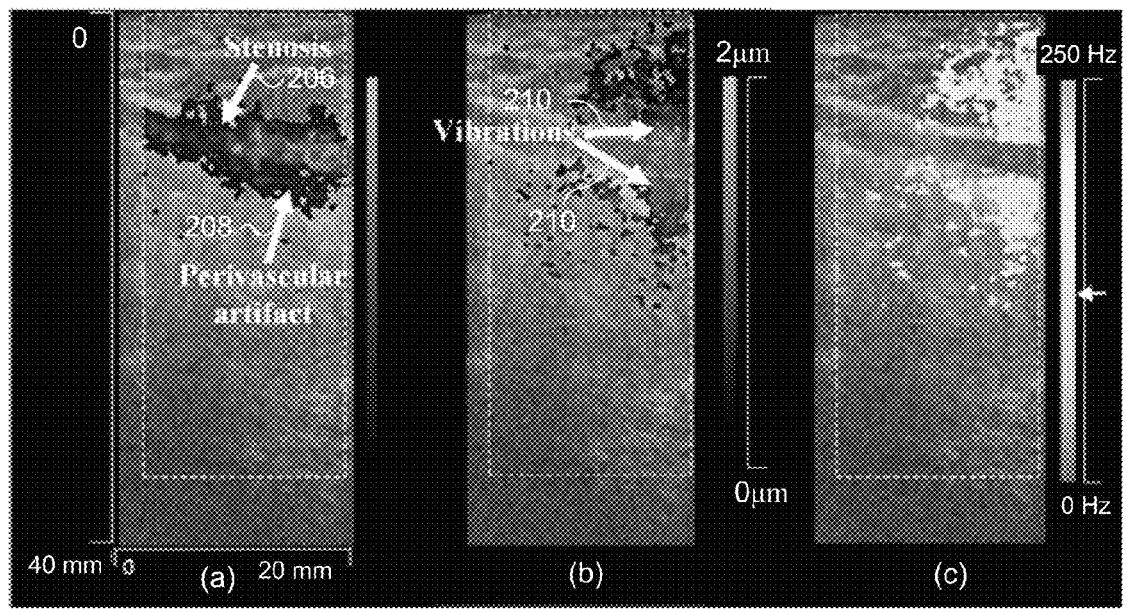
Figure 24A:
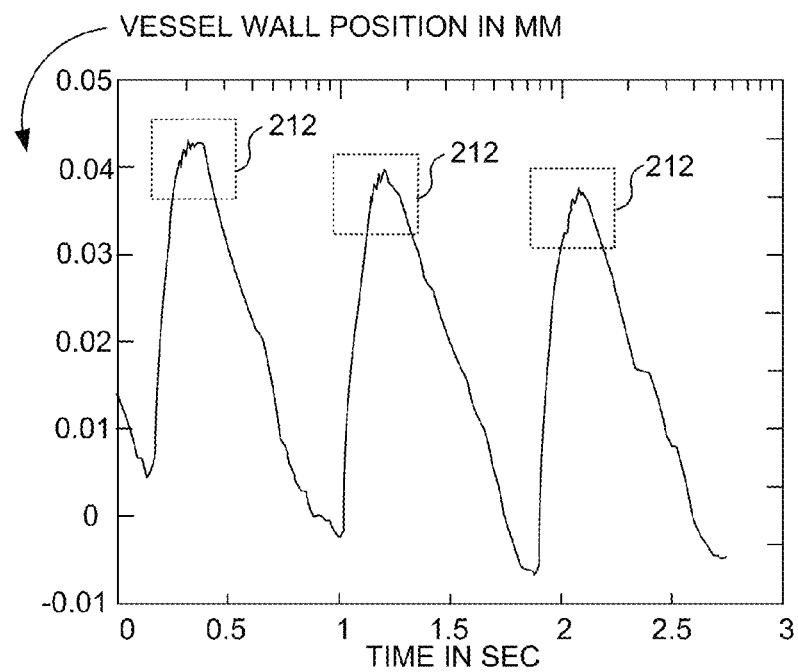
Figure 24B:
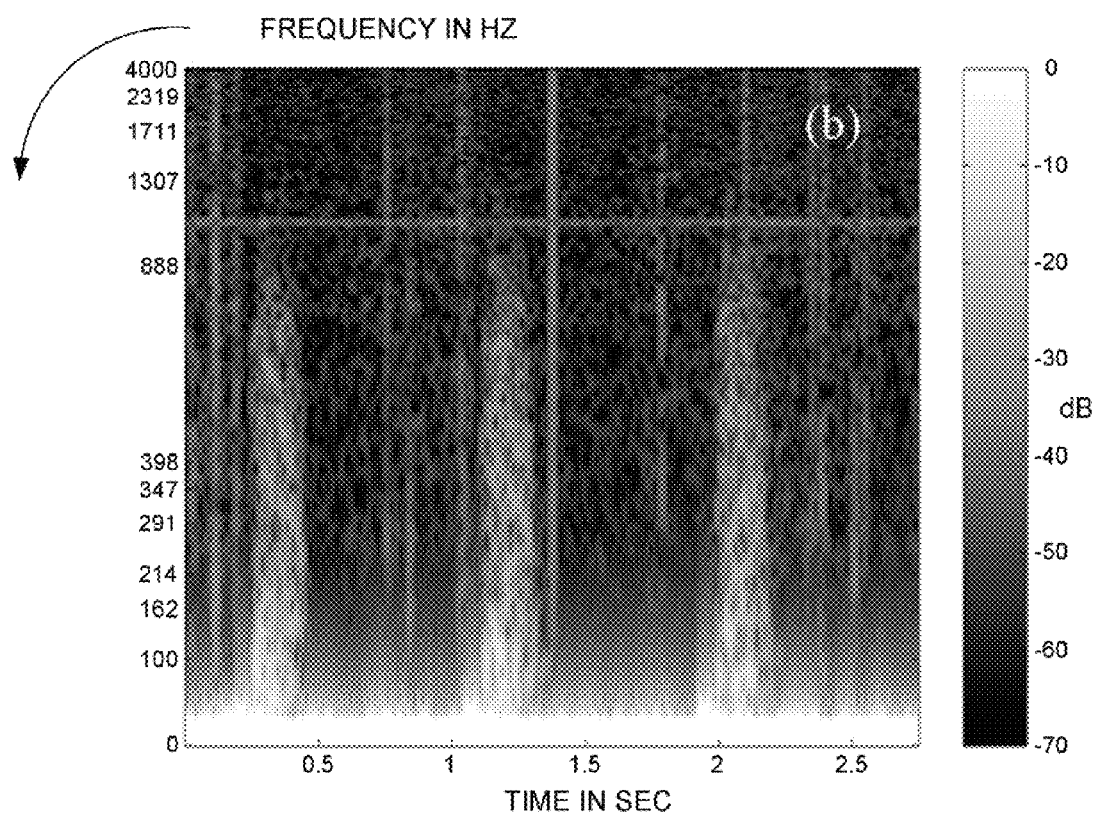
Figure 24C:
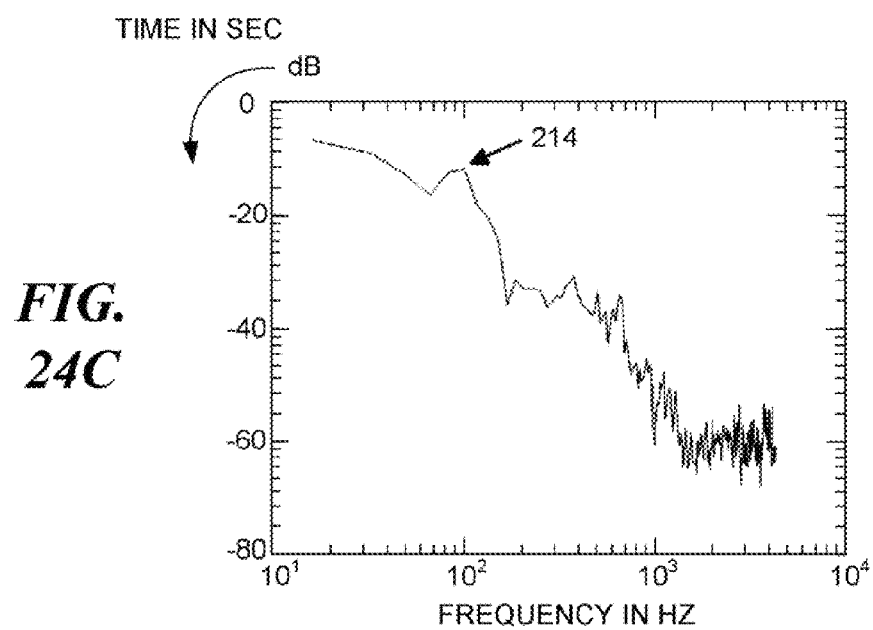
Figure 24D:
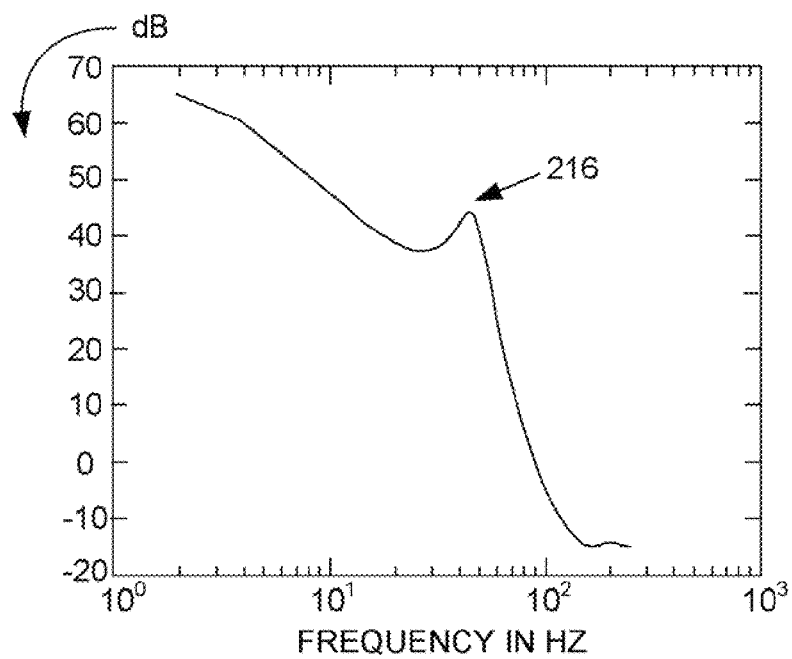
Figure 25A:
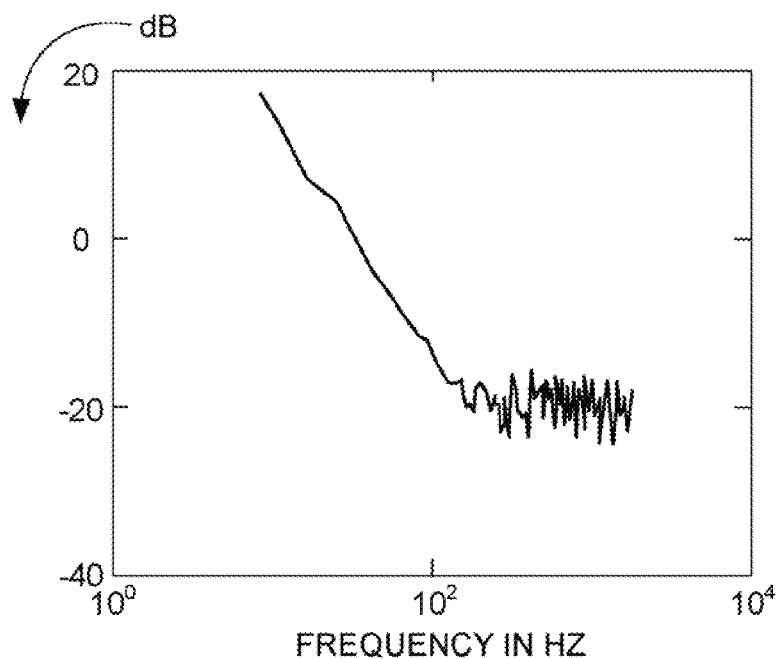
Figure 25B:
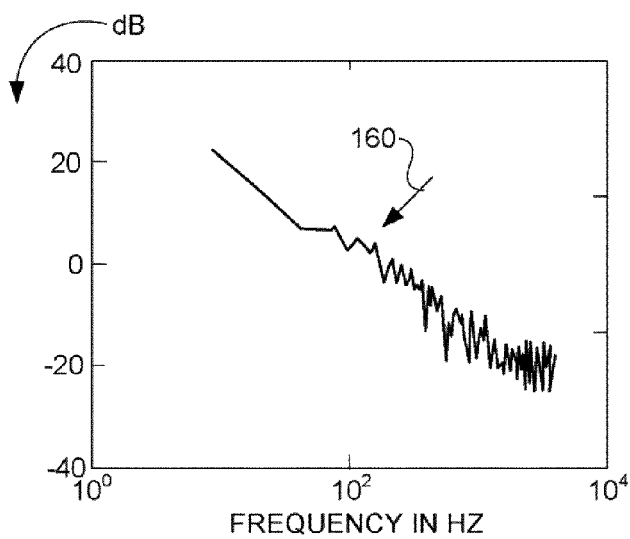
Figure 25C:
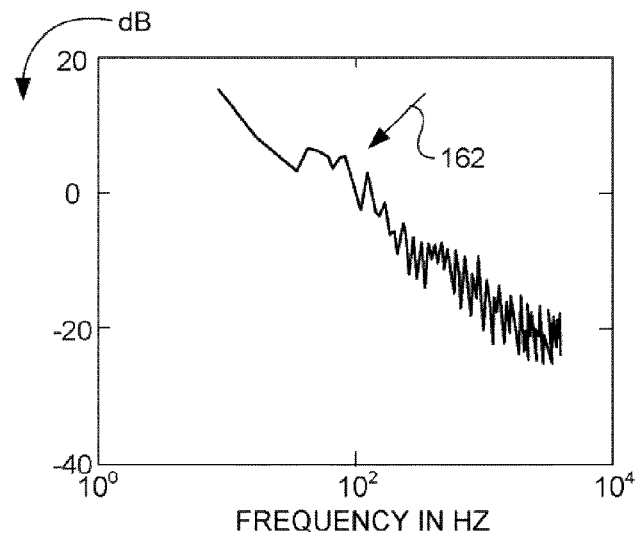
Figure 25D:
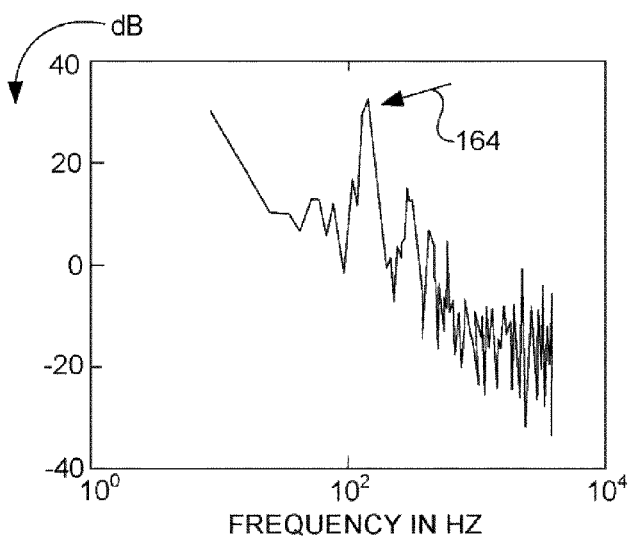
Figures 26A, 26B:
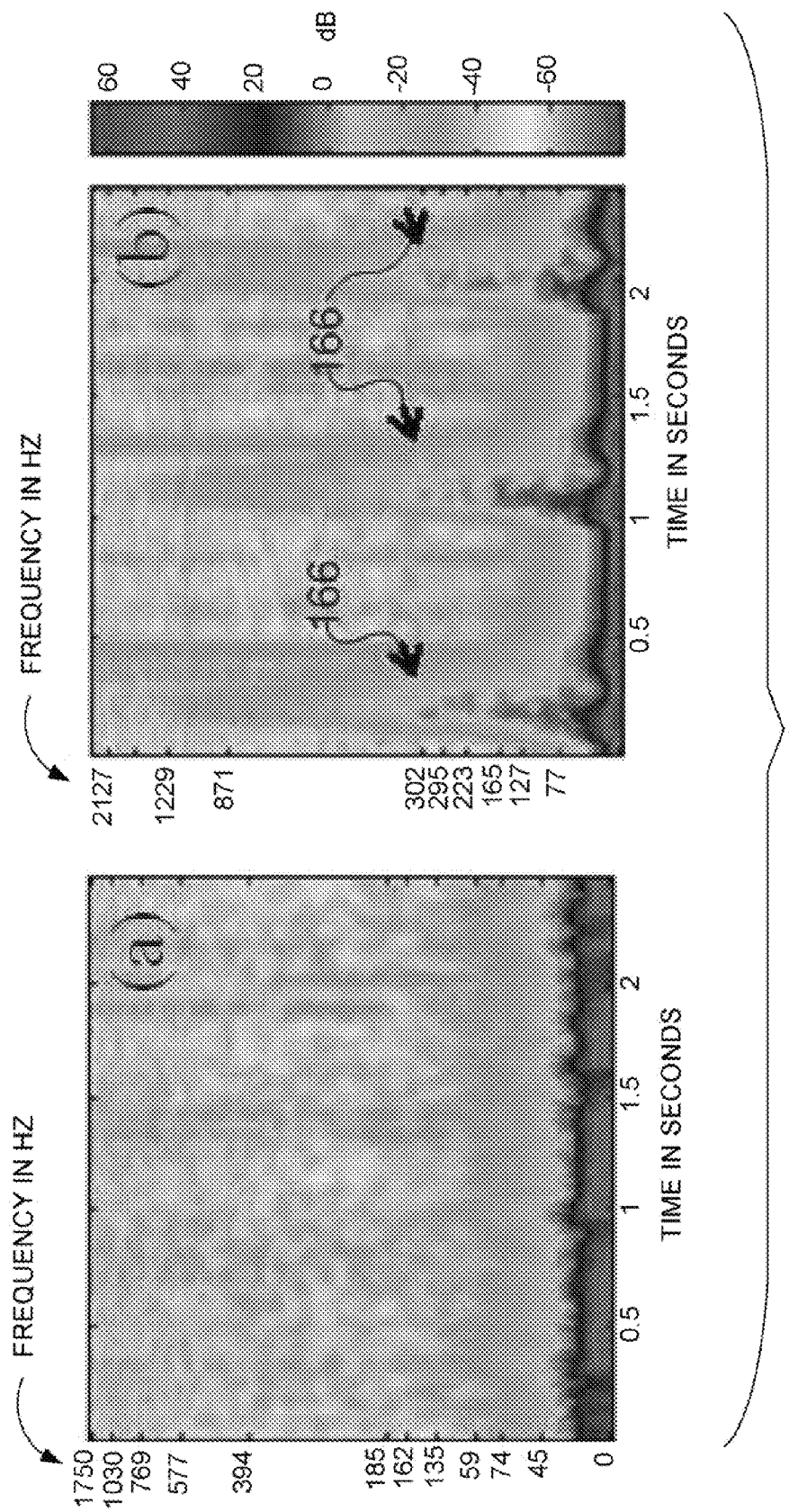
Figures 26C, 26D:
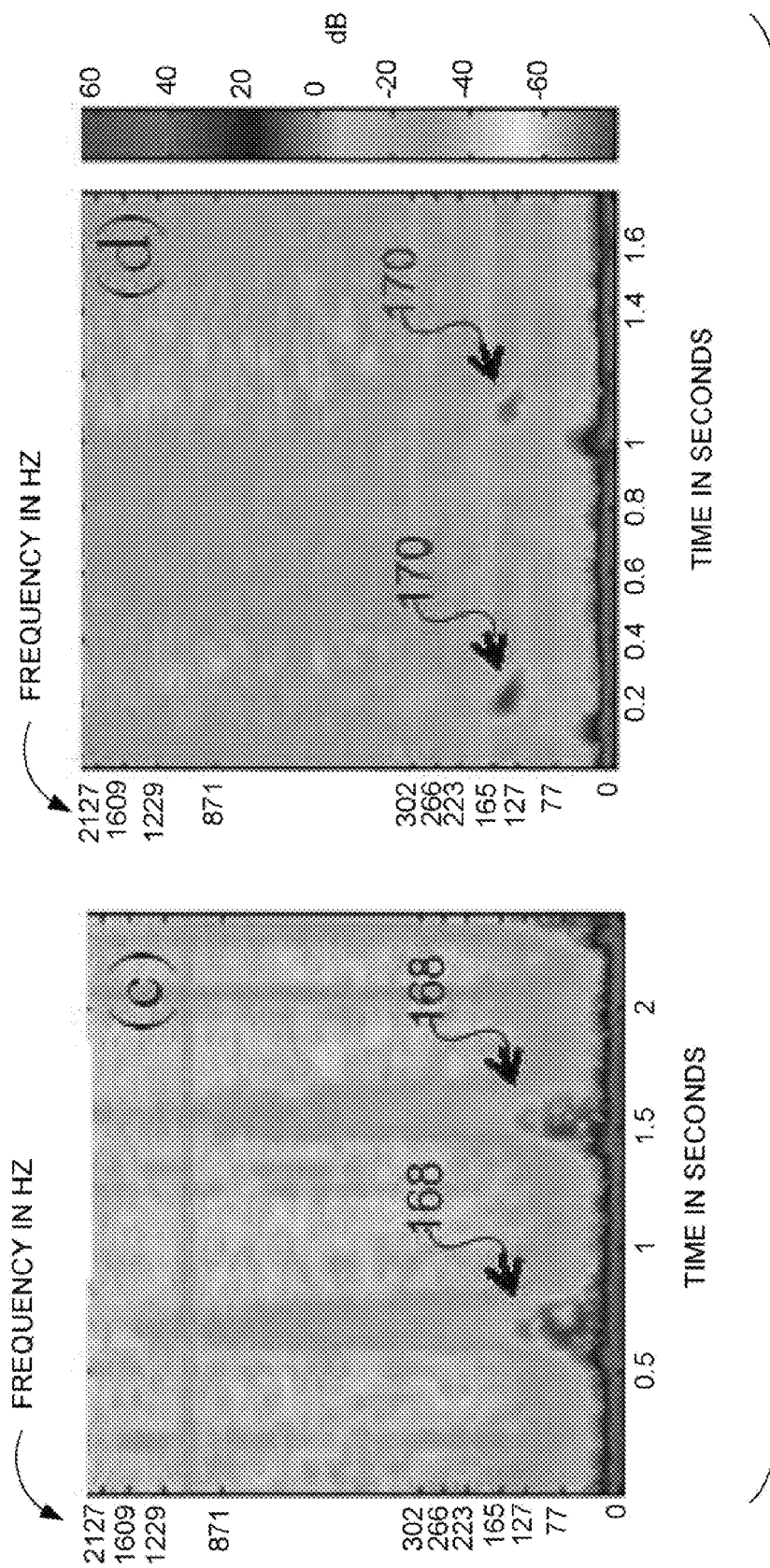
Figures 27A, 27B:
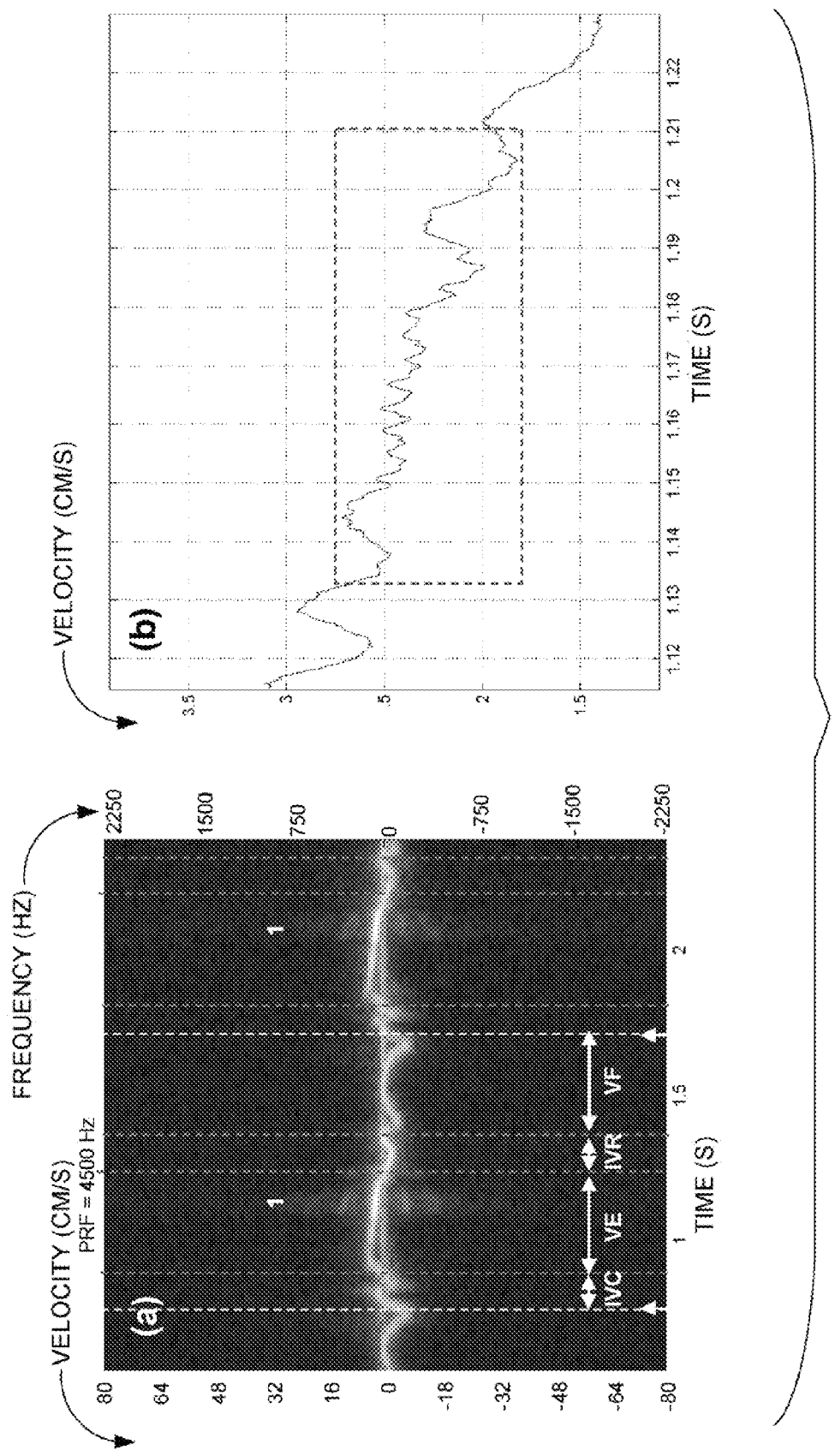
Figure 30:
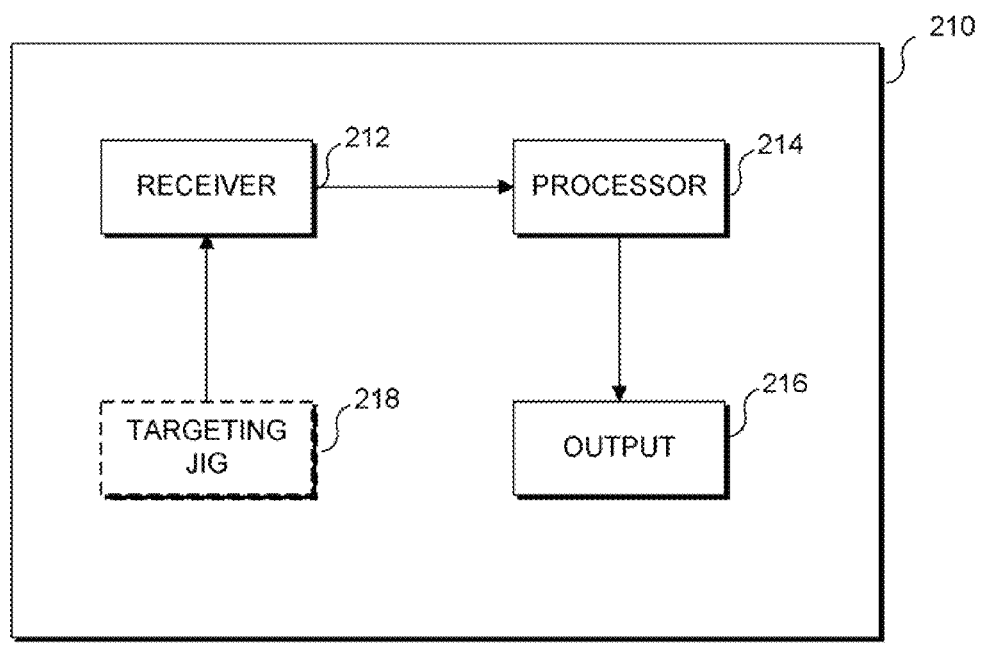
Figure 31:
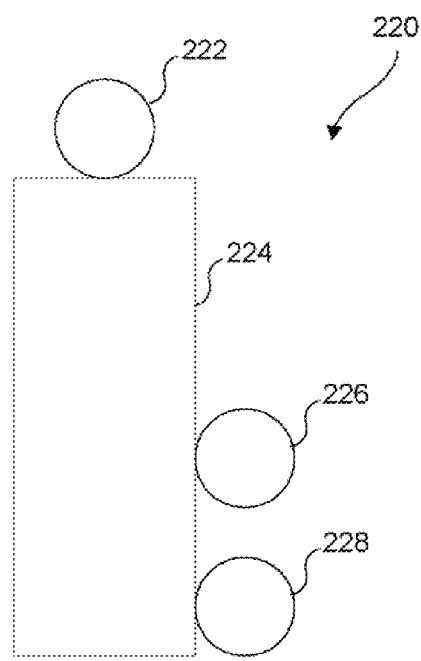
Figure 32:
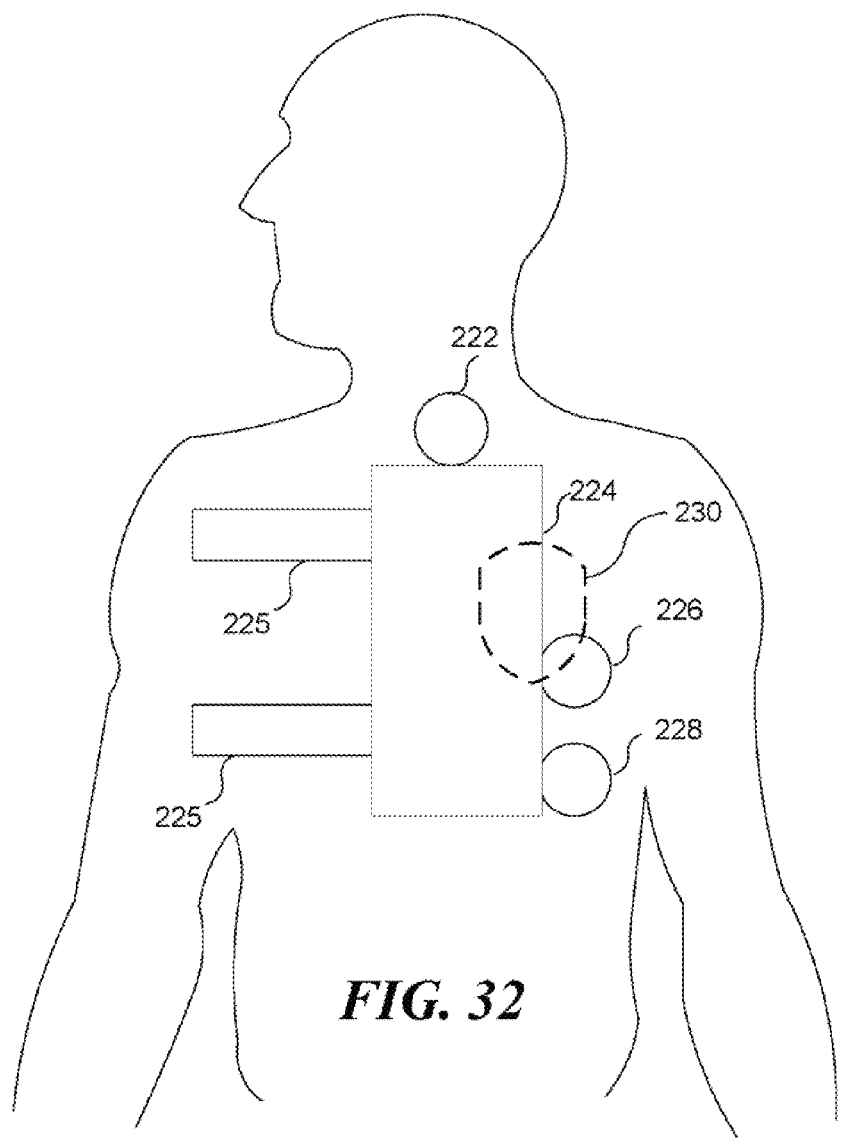
Figure 33:
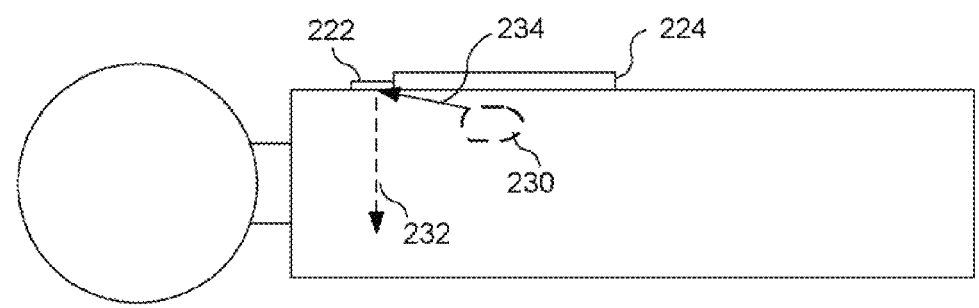
Figure 34:
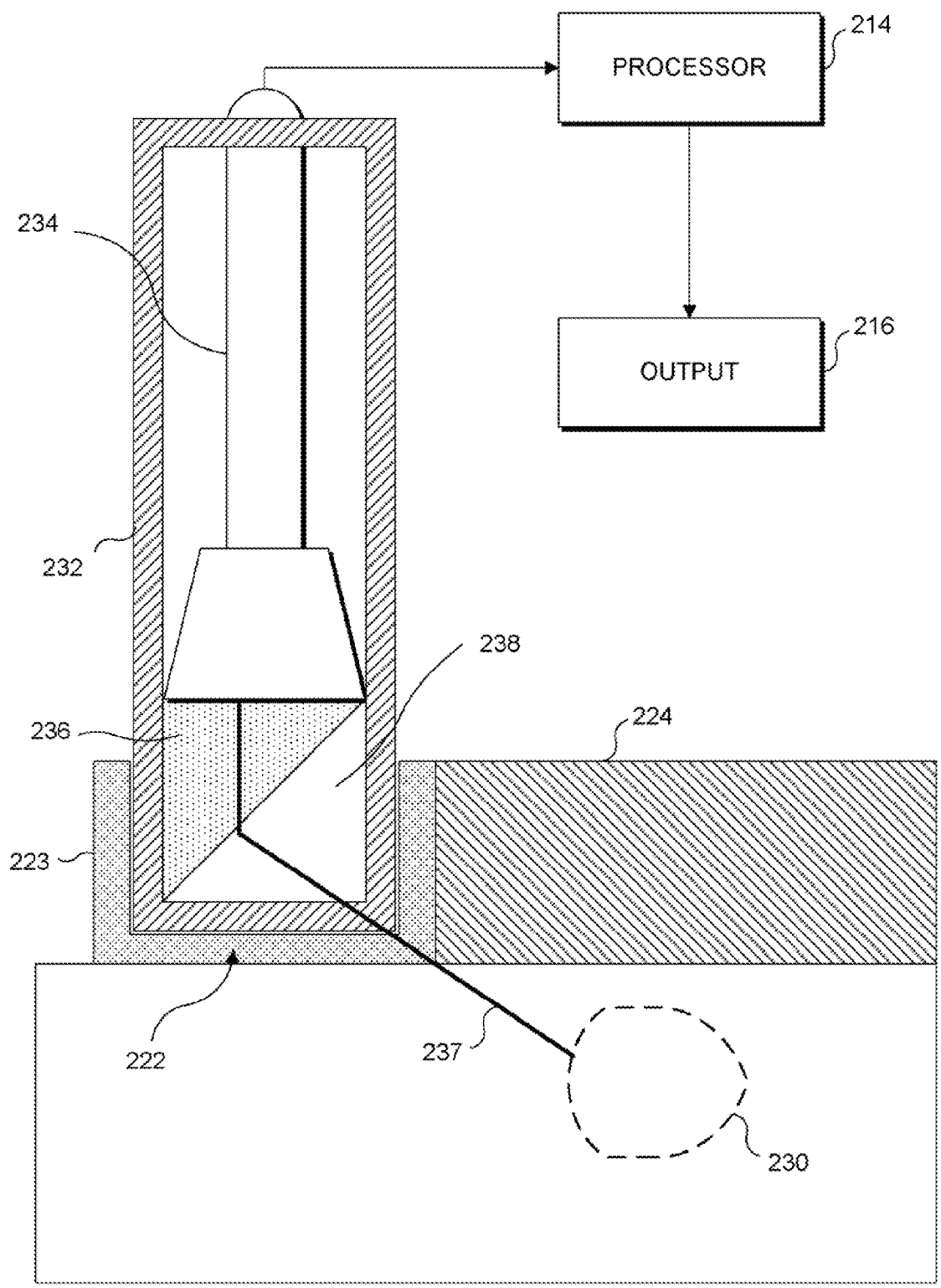
Figure 35:
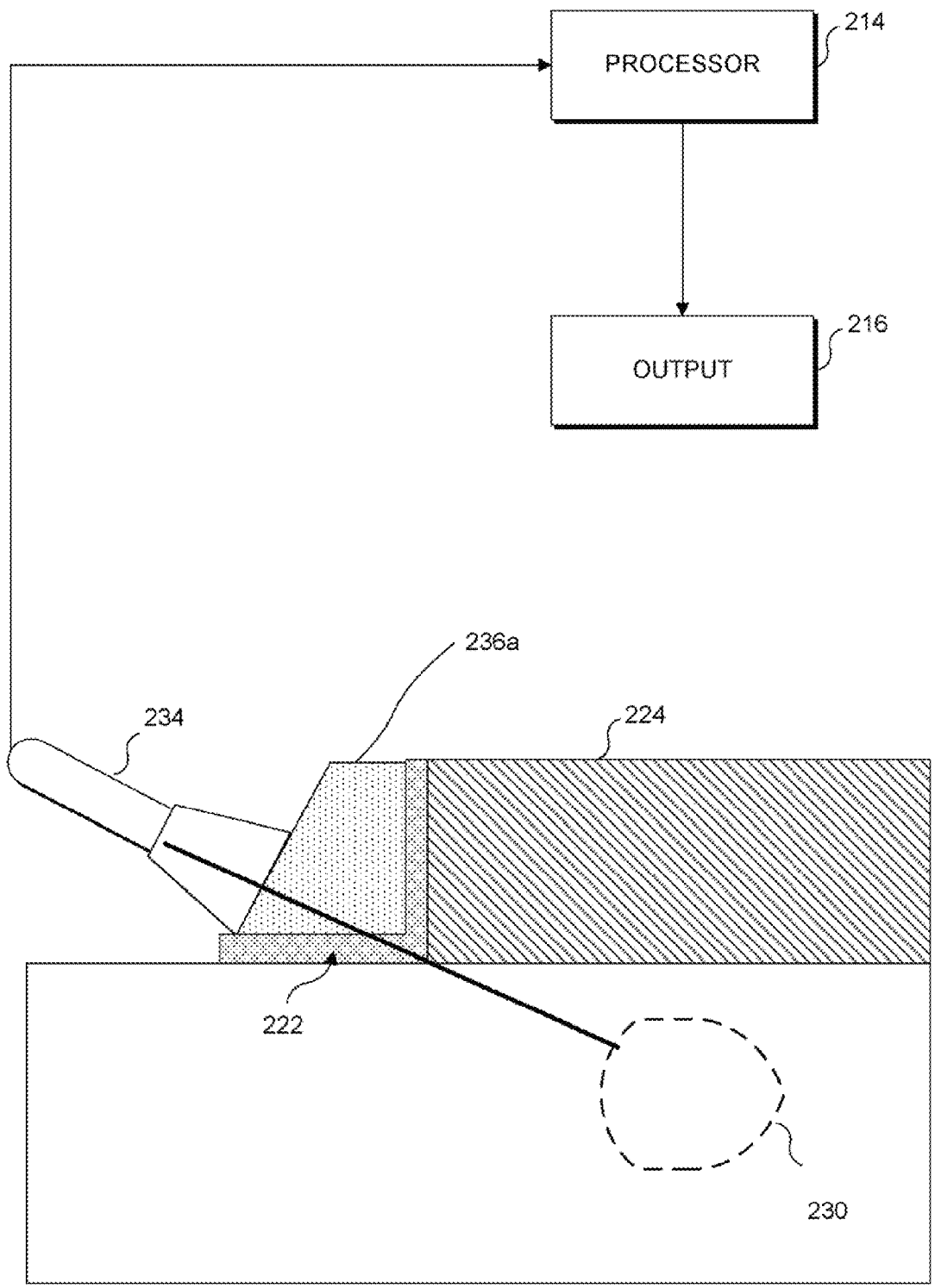
Figure 36:
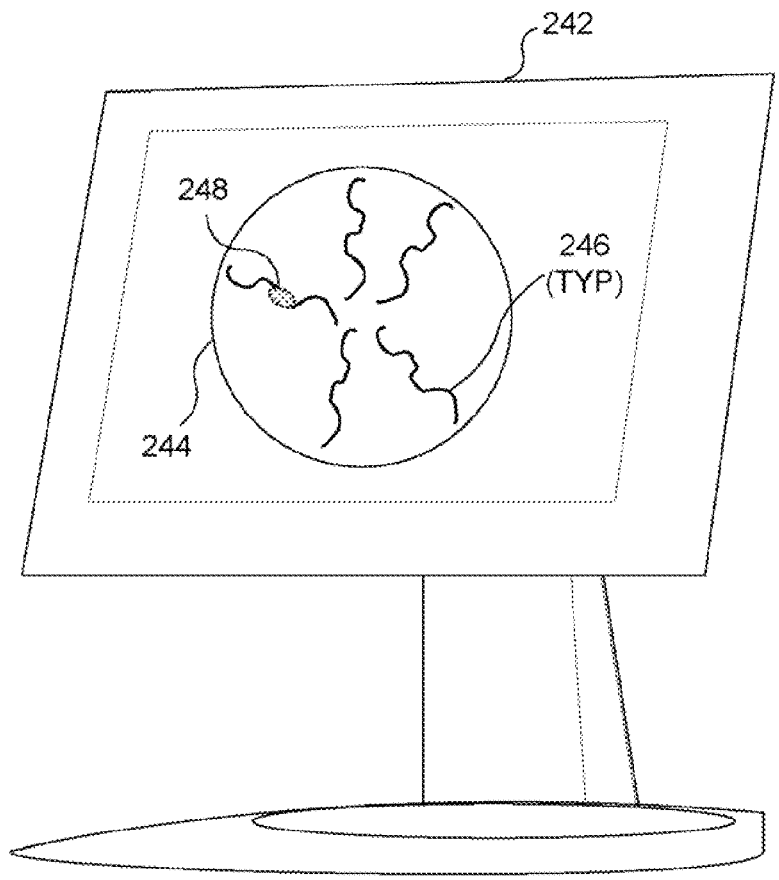
Figure 37:
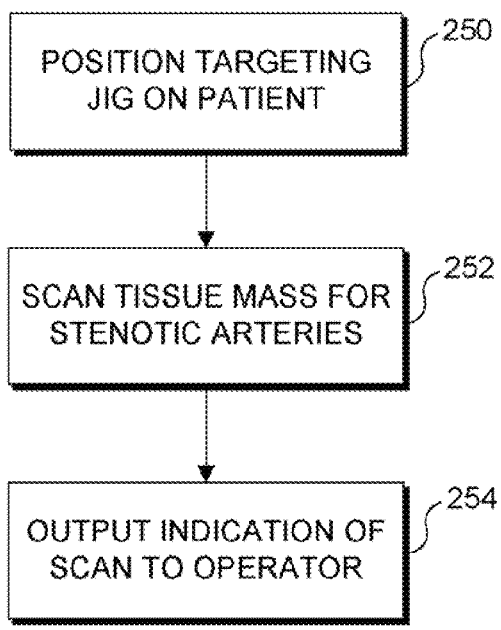

FIG. 5A graphically illustrates both a 2D Fast Fourier Transform (FFT) spectrum and a conventional Doppler spectrum of simulated received ultrasound echoes when scatterers responsible for the echoes are moving with constant velocity of 20 mm/s, the scatterer motion being along the axis of the ultrasound beam, with the Doppler spectrum being disposed to the left of the vertical axis, and the 2D FFT spectrum being disposed on the right of the vertical axis;

FIG. 5B graphically illustrates both a 2D FFT spectrum and a conventional Doppler spectrum of simulated received ultrasound echoes when scatterers responsible for the echoes are moving with a constant velocity of 20 mm/s along the axis of the ultrasound beam, and are also vibrating with a frequency of 300 Hz and an amplitude of 5 µm, with the Doppler spectrum being disposed to the left of the vertical axis, and the 2D FFT spectrum being disposed on the right of the vertical axis;

FIG. 6A graphically illustrates both a 2D FFT spectrum and a conventional Doppler spectrum of received ultrasound echoes (where the center frequency of the transmitted ultrasound signal is 5 MHz) when scatterers responsible for the echoes are moving with a constant velocity of 20 mm/s along the axis of the ultrasound beam, and also vibrating with a frequency of 300 Hz and an amplitude of 5 µm, with the Doppler spectrum being disposed to the left of the vertical axis, and the 2D FFT spectrum being disposed on the right of the vertical axis;

FIG. 6B graphically illustrates both a 2D FFT spectrum and a conventional Doppler spectrum of received ultrasound echoes (where the center frequency of the transmitted ultrasound signal is 2 MHz) when scatterers responsible for the echoes are moving with a constant velocity of 200 mm/s, and also vibrating with a frequency of 300 Hz and an amplitude of 5 µm, with the Doppler spectrum being disposed to the left of the vertical axis, and the 2D FFT spectrum being disposed on the right of the vertical axis;

FIG. 7A graphically illustrates both a 2D FFT spectrum and a conventional Doppler spectrum of simulated received ultrasound echoes from a group of scatterers accelerating from 10 mm/s to 30 mm/s, with an acceleration of 5 m/s$^2$, with the Doppler spectrum being disposed to the left of the vertical axis, and the 2D FFT spectrum being disposed on the right of the vertical axis;

FIG. 7B graphically illustrates both a 2D FFT spectrum and a conventional Doppler spectrum of simulated received ultrasound echoes from a group of scatterers accelerating from 10 mm/s to 30 mm/s, with an acceleration of 5 m/s$^2$, when the scatterers are also vibrating with a frequency of 300 Hz and an amplitude of 5 µm, with the Doppler spectrum being disposed to the left of the vertical axis, and the 2D FFT spectrum being disposed on the right of the vertical axis;

FIG. 8A graphically illustrates both a 2D FFT spectrum and a conventional Doppler spectrum of simulated received ultrasound echoes when scatterers responsible for the echoes are moving with a constant velocity of 20 mm/s, the scatterer motion being perpendicular to the axis of the ultrasound beam, with the Doppler spectrum being disposed to the left of the vertical axis, and the 2D FFT spectrum being disposed on the right of the vertical axis;

FIG. 8B graphically illustrates both a 2D FFT spectrum and a conventional Doppler spectrum of simulated received ultrasound echoes when scatterers responsible for the echoes are moving with a constant velocity of 20 mm/s, the scatterer motion being perpendicular to the axis of the ultrasound beam, where the scatterers are also vibrating with a frequency of 300 Hz and an amplitude of 5 µm with the Doppler spectrum being disposed to the left of the vertical axis, and the 2D FFT spectrum being disposed on the right of the vertical axis;

FIG. 9A graphically illustrates a Radon transform of the 2D FFT spectrum of FIG. 5A;

FIG. 9B graphically illustrates a Radon transform of the 2D FFT spectrum of FIG. 5B;

FIG. 9C graphically illustrates a spectral estimate computed from the Radon transform of FIG. 9A;

FIG. 9D graphically illustrates a Doppler spectral estimate computed from the Radon transform of FIG. 9B;

FIG. 10A graphically illustrates a multifrequency spectral estimate computed from the 2D FFT spectrum of FIG. 5A;

FIG. 10B graphically illustrates a multifrequency spectral estimate computed from the 2D FFT spectrum of FIG. 5B;

FIG. 11A schematically illustrates a 3D simulation model of scatterer distributions used to validate the use of ultrasound to image vibrations associated with a stenosis, as described herein;

FIG. 11B graphically illustrates modeled clutter motion with vibrations indicated by a boxed-in region;

FIG. 11C graphically illustrates a modeled blood flow profile;

FIG. 12A is a vibration amplitude image of a simulation model used to validate the vibration imaging techniques disclosed herein;

FIG. 12B schematically illustrates masks used for computing the sensitivity and specificity of vibration detection;

FIG. 13A graphically illustrates sensitivity versus threshold curves for phase-decomposition-based vibration detection;

FIG. 13B graphically illustrates specificity versus threshold curves for phase-decomposition-based vibration detection;

FIG. 13C graphically illustrates receiver-operating characteristic curves for phase-decomposition-based vibration detection;

FIG. 13D graphically illustrates sensitivity versus threshold curves for root-MUSIC-based vibration detection;

FIG. 13E graphically illustrates specificity versus threshold curves for root-MUSIC-based vibration detection;

FIG. 13F graphically illustrates exemplary receiver-operating characteristic curves for root-MUSIC-based vibration detection;

FIG. 14 graphically illustrates the robustness of sensitivity to increasing vibration bandwidth for the phase-decomposition and root-MUSIC algorithms disclosed herein;

FIG. 15 schematically illustrates an experimental setup in which an ultrasound probe is used to image the vibration of a plate, such a setup having been used to generate empirical evidence in support of using ultrasound to image tissue vibrations, as disclosed herein;

FIG. 16A is a B-mode ultrasound image of the vibration phantom of FIG. 15, overlaid with vibration amplitude;

FIG. 16B is a B-mode ultrasound image of the vibration phantom of FIG. 15, overlaid with vibration frequency;

FIG. 16C graphically illustrates a MUSIC pseudo-spectrum of I-Q ensemble data extracted from a portion of the ultrasound image of FIG. 16B;

FIG. 17A graphically illustrates a vibration amplitude of the plate from the experimental setup of FIG. 15 obtained using both ultrasound and an optical fiber micrometer;

FIG. 17B graphically illustrates a vibration frequency of the plate from the experimental setup of FIG. 15 obtained using both ultrasound and an optical fiber micrometer;

FIG. 17C graphically illustrates the differences between the vibration amplitude of the plate from the experimental setup of FIG. 15 obtained using both ultrasound and an optical fiber micrometer;

FIG. 17D graphically illustrates the differences between the vibration frequency of the plate from the experimental setup of FIG. 15 obtained using both ultrasound and an optical fiber micrometer;

FIG. 18 schematically illustrates an experimental setup in which an ultrasound probe is used to image a stenosis in an ex vivo artery, such a setup having been used to generate empirical evidence in support of using ultrasound to image tissue vibrations associated with a stenosis, as disclosed herein;

FIG. 19 is an image of the flow in the ex vivo artery of FIG. 18;

FIGS. 20A and 20B are respectively vibration amplitude images of an ex vivo artery obtained using the experimental setup of FIG. 18, with FIG. 20A representing a simulated stenosis of 30%, and FIG. 20B representing a simulated stenosis of 42%;

FIG. 21 graphically depicts vibration spectra from a stenosis simulated using the experimental setup of FIG. 18, the vibration spectra being generated using both pulsed-wave Doppler ultrasound and a fiber optic micrometer;

FIG. 22A is a Color-Doppler image from a stenosed vein graft in a human subject;

FIG. 22B is a vibration amplitude image of the stenosed vein graft of FIG. 9A;

FIG. 23A is a color power ultrasound image of a stenosed femoral vein graft including perivascular artifacts;

FIG. 23B is a vibration amplitude image of the stenosed femoral vein graft of FIG. 23A;

FIG. 23C is a vibration frequency image of the stenosed femoral vein graft of FIG. 23A;

FIG. 24A graphically illustrates instantaneous vessel wall position estimated using phase decomposition of pulsed wave Doppler data from a stenosed femoral vein graft;

FIG. 24B is a motion periodogram of the signal used to generate FIG. 24A;

FIG. 24C graphically illustrates a cross-sectional profile of the spectrum of FIG. 24B at a particular point in time;

FIG. 24D graphically illustrates a motion pseudo-spectrum computed using the MUSIC algorithm for 10 ensembles of color-flow ultrasound data at the same location;

FIG. 25A graphically illustrates an arterial wall displacement spectra of a normal femoral artery obtained in vivo using the techniques disclosed herein;

FIG. 25B graphically illustrates an arterial wall displacement spectra of a stenosed femoral bypass vein graft obtained in vivo using the techniques disclosed herein;

FIG. 25C graphically illustrates an arterial wall displacement spectra of a different stenosis present in the same patient as the stenosis represented in FIG. 25B;

FIG. 25D graphically illustrates an arterial wall displacement spectra of a stenosis present in another patient;

FIG. 26A graphically illustrates a time-varying wall vibration spectra of a normal artery obtained using the techniques disclosed herein;

FIGS. 26B-D graphically illustrate time-varying wall vibration spectra of stenosed blood vessels obtained using the techniques disclosed herein;

FIG. 27A is a Doppler spectrum computed using a 2D FFT method from an ultrasound image of the myocardium of a patient who has coronary artery disease, symmetric double-sided peaks being indicative of vibrations observed in the late ventricular ejection phase;

FIG. 27B graphically illustrates a time course of a wall velocity during ventricular ejection, a boxed-in region indicating high-frequency vibrations that appear to include harmonic components;

FIG. 28A is an angiographic image of a patient who has coronary artery disease, acquired in the left anterior oblique projection with caudal angulation;

FIG. 28B is a vibration amplitude image overlaid on an apical two-chamber view of the patient of FIG. 28A;

FIG. 29A is an angiographic image of a patient who has coronary artery disease, acquired in right anterior oblique projection with cranial angulation;

FIG. 29B is a vibration amplitude image overlaid on the apical two-chamber view of the patient of FIG. 29A; and FIG. 30 schematically illustrates a vibrometry screening system including an ultrasound transducer, a processor, an output, and an optional targeting jig;

FIG. 31 schematically illustrates an exemplary targeting jig;

FIG. 32 is a schematic plan view of the exemplary targeting jig of FIG. 31 in use;

FIG. 33 is a schematic side elevation view of the exemplary targeting jig of FIG. 31 in use;

FIG. 34 is an enlarged side elevation view of the exemplary targeting jig of FIG. 31 in use;

FIG. 35 is an enlarged side elevation view of another exemplary targeting jig;

FIG. 36 graphically illustrates an exemplary output for use in a scanning system for coronary stenoses; and FIG. 37 graphically illustrates an exemplary method for using a stenotic artery scanning system.

DESCRIPTION

Figures and Disclosed Embodiments are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein. Further, it should be understood that any feature of one embodiment disclosed herein can be combined with one or more features of any other embodiment that is disclosed, unless otherwise indicated.

Comparison and Contrast of Vibrometry as Disclosed Herein with Imaging Ultrasound The concepts disclosed herein are generally referred to as vibrometry. While related to imaging ultrasound, it must be noted that the vibrometry techniques disclosed herein are not the same as imaging ultrasound. The key difference between vibrometry and imaging ultrasound is the manner in which an ultrasound signal received by an ultrasound transducer is processed. In imaging ultrasound (i.e., B-mode ultrasound), the B-mode image is formed using reflections generated as the ultrasound encounters interfaces between different types of tissue (or bone). The image being generated, often referred to as an echogram, is a visual record of the different interface layers encountered by ultrasound passing through a region of tissue. In contrast, the vibrometry techniques disclosed herein are not concerned with such interface layers, rather the vibrometry techniques process the collected ultrasound signal to identify vibrations present in the tissue (note such vibrations are not reflections of ultrasound energy introduced into the mass of tissue, and reflected off of various interface layers). Known vibration sources are eliminated from the collected ultrasound signal, such that remaining vibration components of the signal are attributed to a stenosis. Knowledge of the tissue region from which the ultrasound signal is collected is used to determine in which artery (or vessel) the stenosis is present.

Significantly, the vibrometry techniques disclosed can detect a stenosis in an artery that cannot be visualized using B-mode (or Doppler mode) ultrasound. The resolution of imaging ultrasound is a function of frequency and depth. For example, superficial structures such as muscles, tendons, testes, and breasts are imaged at relatively higher frequencies, ranging from about 7 to about 18 MHz, which provides relatively good axial and lateral resolution. Deeper structures, such as the liver, heart and kidney are imaged at relatively lower frequencies, ranging from about 1 to about 6 MHz, with relatively lower axial and lateral resolution, but greater penetration. The deeper and smaller an artery, the less likely non-invasive imaging ultrasound can be used to successfully image such structures (noting that if an invasive procedure were performed to locate the transducer closer to the structure, such imaging could be achieved; however that would negate one of ultrasound's primary benefits, that of its non-invasiveness). Cardiac arteries in particular are small enough, and deep enough, that the resolutions of B-mode and Doppler mode ultrasound are insufficient to enable such structures to be routinely successfully imaged.

It should be understood that the term vibration image, as used herein and the claims that follow, is not equivalent to a B-mode or Doppler mode ultrasound image. Generally as discussed above, B-mode and Doppler mode ultrasound images are based on ultrasound reflections at different interfaces in a mass of tissue. As used herein, a vibration image is generated by processing an ultrasound signal received from a mass of tissue to identify vibration sources within that mass of tissue, and then visually displaying either the relative location of the vibration source in the mass of tissue or a representation of characteristics of the vibration.

Significantly, the concepts disclosed herein can be used to generate a vibrometry image of blood vessels (including cardiac arteries) that are too small to be imaged using B-mode ultrasound or Doppler mode ultrasound. Thus, one aspect of the concepts disclosed herein is to detect stenoses in arteries that cannot be visualized using B-mode ultrasound or Doppler mode ultrasound.

It should also be noted that B-mode ultrasound is best at visualizing blood vessels when the ultrasound beams forming the two-dimensional image are perpendicular to the walls (and axis) of the artery, so that the specular echoes from the walls are large, and the image plane is aligned with the artery (so that the echoes form a visible line). Doppler ultrasound (including color Doppler and color power angiography) is best at visualizing blood vessels when the ultrasound beam is aligned (parallel) to the artery axis.

In contrast, the vibrometry techniques disclosed herein are designed to detect a stenosis from any angle, by gathering data from a tissue region near a post-stenotic turbulence or eddy. So, while the vibrometry techniques disclosed herein cannot be used to visualize arteries in the same manner as B-mode and Doppler ultrasound, the vibrometry techniques disclosed herein can be used to detect stenotic and bleeding arteries that cannot be seen by B-mode and Doppler ultrasound.

In deep tissue, conventional imaging ultrasound (i.e., B-mode and Doppler ultrasound) generally have a lateral resolution of about 1 cm. Relatively small arteries (such as cardiac arteries) have diameters of 1 mm. Limiting factors for B-mode ultrasound imaging and Doppler ultrasound imaging are resolution and penetration. Resolution allows one to distinguish between two or more objects that are close together, whereas penetration allows one to see the objects. High frequency (short wavelength) ultrasound attenuates rapidly in tissue, penetrating only to shallow depths. In general, B-mode imaging is useful to a depth of about 200 wavelengths of ultrasound, with a normal attenuation of about 1 db/cm/MHz). 5 MHz ultrasound has a wavelength of about 0.3 mm, so using such ultrasound enables imaging of tissue to a depth of about 60 mm. 3 MHz ultrasound has a wavelength of about 0.5 mm, so using such ultrasound enables imaging of tissue to a depth of about 100 mm.

The depth resolution of B-mode ultrasound imaging and Doppler ultrasound imaging is about equal to the wavelength (3 MHz, 0.5 mm). The lateral resolution of B-mode ultrasound imaging and Doppler ultrasound imaging is about equal to the wavelength (depth/aperture). So, with a 20 mm wide aperture (often used as a cardiac ultrasound imaging transducer) at a depth of about 100 mm, the lateral resolution (for 3 MHz ultrasound) is about 5 mm. In practice, lateral resolution is actually much poorer than that, due to refractive distortion of the ultrasound beam.

Another problem with generating B-mode or Doppler mode ultrasound images from coronary arteries is that ultrasound scattering from red blood cells is much greater at higher frequencies. For example, scattering increases by the $4^{th}$ power of the frequency, so at relatively low frequencies, like the 3 MHz ultrasound normally employed for cardiac ultrasound imaging, the "Doppler power" of the ultrasound is reduced by $\frac{1}{8}$ compared to 5 MHz ultrasound. Thus, the likelihood of being able to use ultrasound imaging to see blood velocity in coronary arteries (which range from about 1 mm in diameter to about 2.5 mm in diameter) is very poor.

The vibrometry techniques disclosed herein avoid that problem by detecting the signal from the vibration around the post-stenotic turbulent zone.

Exemplary Tissue Vibration Imaging System

In discussing an empirical system used to develop the concepts disclosed herein, it will be appreciated that a system capable of generating B-mode ultrasound images was employed. It is important to understand the concepts disclosed herein do not require the generation of B-mode ultrasound images. The same type of ultrasound transducer that can generate and collect ultrasound waves used to produce B-mode ultrasound images can also be beneficially employed to direct ultrasound energy into the tissue being scanned for a stenosis, and receive vibration signals (i.e., the reflected ultrasound energy, modified by some degree due to the stenotic vibrations, if present) from a mass of tissue.

Another difference between the vibrometry concepts disclosed herein and B-mode ultrasound imaging is how the collected ultrasound signal is processed. A conventional B-mode or Doppler mode ultrasound imaging system (i.e., the transducer and processor combination) would be capable of collecting vibration data from a mass of tissue, but would not be capable of the processing of that data to generate a vibration image. To enable B-mode or Doppler mode ultrasound imaging systems to be capable of generating a vibration image, such systems would need to be reprogrammed to process the signal collected from the mass of tissue in different fashion than is required to produce the echograms of B-mode and Doppler mode imaging. The empirical system employed for development purposes was modified to process the received signal to generate the vibration image, as opposed to an echogram.

Figure 1:
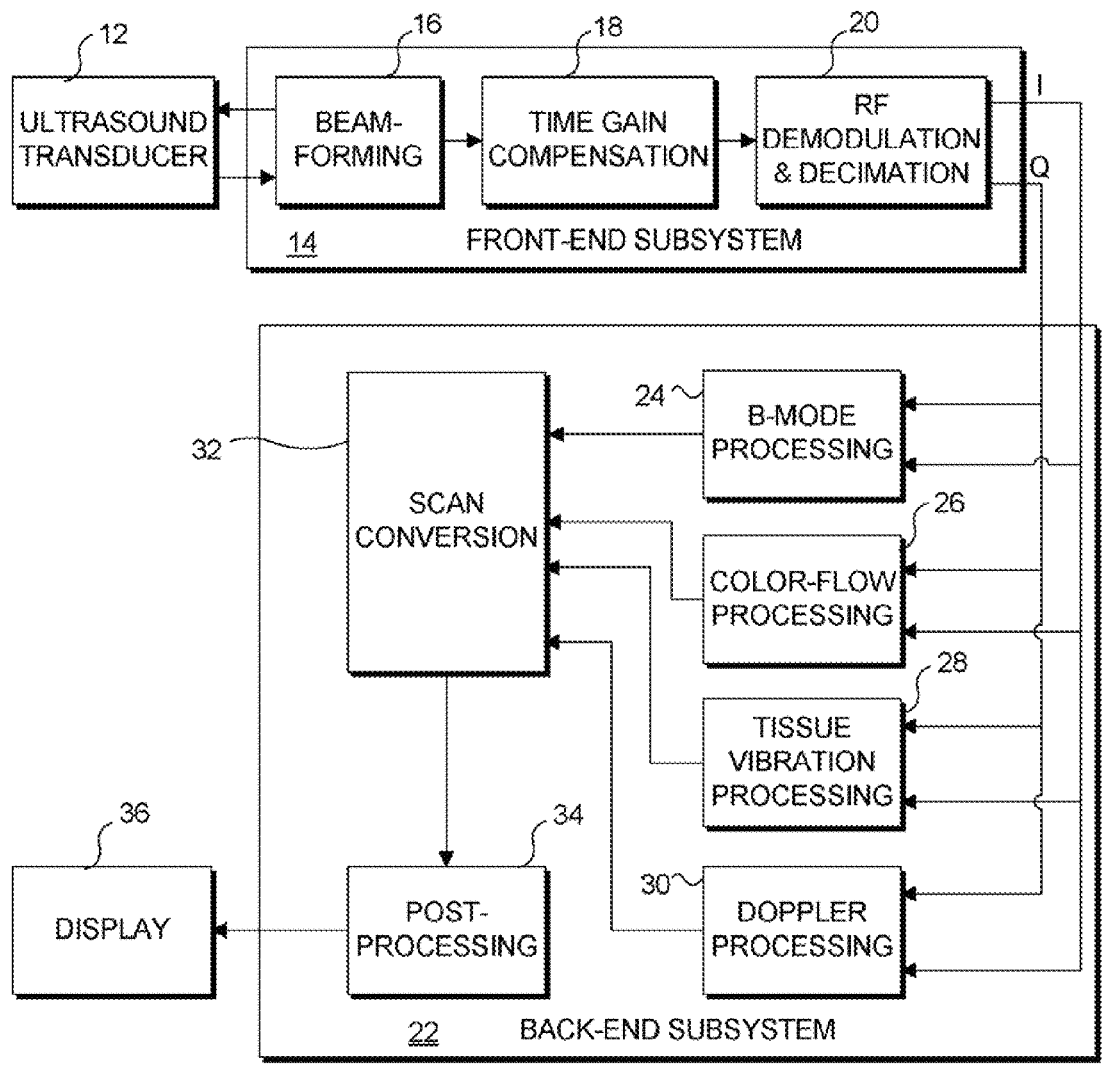
FIG. 1 is a functional block diagram of an exemplary ultrasound system that is suitable for carrying out tissue vibration imaging.

FIG. 1 is a block diagram illustrating an ultrasound system 10, which is generally similar to a conventional ultrasound system, but which has been modified to include tissue vibration imaging and is thus usable in practicing the concepts disclosed herein. Ultrasound system 10 includes an ultrasound transducer 12 that transmits a signal, which is modulated with a carrier frequency, typically 1 MHz-15 MHz, using multiple cycles (i.e., 2-20 cycles). The transmitted signal is reflected by scatterers (not shown) along the beam path and is received after a time delay, the duration of which depends upon the distance of the scatter from the transducer. In an acquisition stage, the acoustic echoes received from the tissue are converted to electrical signals by the transducer, and these signals are digitized by analog-to-digital converters (not separately shown). A front-end subsystem 14 includes a beam former 16 that performs dynamic focusing, apodization, and steering of both transmitted and received ultrasonic waveforms. Also included in front-end system 14 are a time-gain-compensation (TGC) circuit 18 that amplifies signals with a variable gain that is proportional to the depth within tissue, and a radio frequency (RF) demodulator and decimator 20 that digitally removes the high frequency carrier by quadrature demodulation and decimation, providing both in-phase (I) and quadrature (Q) samples, which may be represented as a complex quantity, I(t)+jQ(t). The acquired quadrature ensemble (or color-flow) data are then processed in a back-end subsystem 22, depending on the one (or more) ultrasound mode(s) that is/are selected, e.g., B-mode, color-flow mode, tissue vibration mode, and Doppler mode.

For producing anatomic images of tissue, the signal of interest is the envelope of I(t)+jQ(t). A B-mode processor 24 computes the magnitude of the echo, $B_a(t)=\sqrt{I^2(t)+Q^2(t)}$ and compresses the dynamic range to make it suitable for display as a grayscale image on a monitor. The time delay introduced by the scatterers is reflected in the phase of the complex quantity I(t)+jQ(t). Thus, the phase of the complex received signal provides an estimate of the instantaneous position of the scatterer. By monitoring the change of phase over time, the displacement and velocity of the scatterer can be estimated. In color-flow imaging, multiple pulses (commonly from 6 to 16 pulses) are transmitted and received along each scan line at a rate known as the pulse repetition frequency (PRF). A collection of received temporal samples from each spatial location is thus called an "ensemble." A color-flow processor 26 estimates the blood flow velocity from the ensemble of data by estimating the phase difference between the adjacent temporal samples, typically using an autocorrelation algorithm. A 2D image is created by acquiring multiple samples from different spatial locations. In Doppler mode, which is implemented with a Doppler processor 30, scanning is performed along a single scan line, and a spectrum of the blood velocity from a single spatial location is estimated from a substantially larger ensemble of data (typically, data from 64-512 pulses). Before displaying the processed image frame on a raster monitor or display 36, scan conversion is performed by a scan converter circuit 32, which converts the acquired ultrasound data from polar coordinates to the Cartesian coordinates used by the raster display. Post-processing may optionally be applied by a post-processing circuit 34, to improve the quality of the displayed image, as well as to combine the anatomy and flow images on the display.

A tissue vibration processor 28 that is used to process the ultrasound data in one exemplary embodiment is shown in FIG. 1. The quadrature data ensembles are input to the tissue vibration processor. However, instead of estimating blood flow velocity from these data, the tissue vibration processor estimates the instantaneous displacement of the scattering tissue from the phase of the complex received signal. This tissue motion is referred to as clutter in conventional color-flow imaging and is suppressed using clutter filters. Typically, cardiac pulsation, respiration and transducer motion each can contribute to an observed displacement or motion of tissue. Such motion is at a low frequency of a few Hertz or less. When a stenosis is present, the tissue surrounding the stenosis vibrates locally with a frequency ranging from a few tens of Hertz to more than 1000 Hertz. By analyzing the frequencies of the different components of tissue motion, vibrations caused by stenosed blood vessels may be distinguished from clutter caused by other sources of movement. The tissue vibration processor performs this analysis by decomposing the tissue motion into the dominant motion components and identifying any motion components that appear to be at a frequency higher than that of cardiac pulsation.

It is contemplated that tissue vibration processor 28 can be implemented as an additional fixed-function circuit board or an application specific integrated circuit (ASIC) for use in conventional ultrasound machines. Optionally, the tissue vibration processor can be combined with color-flow processor 26, since both process the same data ensemble. A standalone tissue vibration imaging device can be implemented with front-end subsystem 14, B-mode processor 24, tissue vibration processor 28, and scan converter 32. Those of ordinary skill in the art will appreciate that the tissue vibration processor can be implemented in software/hardware using one or more digital signal processors (DSPs) or alternatively, in an ASIC, or even on a conventional general purpose processor chip that accesses machine language instructions stored in a memory accessed by the processor to carry out the processing steps of the tissue vibration processor.

The computational power of ultrasound machines has increased significantly in recent years, benefiting from advances in processor technology. Thus, the additional computational burden arising from executing the tissue vibration imaging algorithms discussed below can be reasonably supported in modern ultrasound machines. Previously, a programmable ultrasound signal and image processing system suitable for use as the tissue vibration processor were developed that use a new generation of high-performance multimedia processors to support all of the conventional processing modes, such as B, M, color-flow, and Doppler in software (Sikdar S, Shamdasani V, Gong L, Managuli R, Hayashi T, Mitake T, Kim Y. "A single mediaprocessor-based programmable ultrasound system," IEEE Trans Inf. Tech. Biomed 2003; 7:64-70), and subsequently, this system was shown to be useful in implementing tissue vibration processing disclosed herein. The main strength of a programmable system is the ease of developing new modes and applications such as tissue vibration imaging without the need for hardware modifications that might be required of conventional ultrasound machines. Integrated tissue vibration imaging using the software-programmable ultrasound system has thus been effectively and beneficially used for real-time visualization of vibrations in 2D ultrasound scans.

Algorithms for Tissue Vibration Imaging

In conventional color-flow imaging, the velocity of blood flow is estimated by computing the average phase difference between multiple ultrasound echoes (typically 6-16 pulses) that are received from a sample volume. Echoes backscattered from moving tissue tend to have a significantly higher signal strength (typically 40 dB-60 dB higher), compared to the weak scattering from blood, and also have lower velocities. This high amplitude and low frequency tissue signal is commonly referred to as clutter and tends to bias the estimated blood flow velocity. Thus, clutter is suppressed using appropriate filters in conventional color flow imaging. The main components of clutter are cardiac pulsation, respiration, and transducer movement. When blood flow eddies are present, any local tissue vibrations, e.g., those caused by the blood flow eddies in stenosed blood vessels, will also be part of this clutter and would normally be suppressed in conventional ultrasound processing systems.

In accord with the concepts disclosed herein, the tissue vibrations are separated from the remaining clutter and flow signals. In achieving this function, it was recognized that the tissue vibrations and clutter produce statistically independent signals that have different frequency content. While clutter due to cardiac pulsation and breathing typically occurs at 1 Hz or less, tissue vibrations typically occur at 50 Hz or more. Other noise sources are at substantially higher frequencies. Scattering from tissue is typically more coherent compared to the scattering from blood, because the tissue scatterers are more tightly bound together and tend to move as a group. Thus, compared to the clutter from other sources and tissue vibration signals, the blood flow signal typically has a much greater frequency bandwidth. Due to its weak signal strength and greater bandwidth, blood flow signals may be considered as noise compared to the stronger and more coherent tissue vibration signals for purposes of this approach. Therefore, tissue vibrations can be distinguished from clutter and blood flow based on spectral analysis. Spectral analysis of the phase of the received ultrasound echo can be used to separate the components of the scatterer motion, ignoring the scattered signal strength, whereas spectral analysis of the complex ultrasound echo considers both the signal strength and the motion components.

Due to the limited number of temporal ultrasound samples (6-16 pulses) preferably used in implementing the present concepts, conventional clutter filtering and spectral estimation techniques lack sufficient resolution to discriminate between the tissue vibrations and normal clutter from such a short temporal record. Therefore, high-resolution spectral estimation techniques were developed to carry out this function.

With respect to imaging vibrations associated with stenosed blood vessels, two high-resolution spectral estimation techniques were identified as suitable for this purpose, including eigen decomposition-based spectral estimation, which models the signal as an optimum set of orthogonal components, and autoregressive spectral estimation, which models the signal as the output of an autoregressive linear prediction filter driven by white Gaussian noise. Accordingly, three signal processing algorithms were developed for isolating tissue vibrations associated with stenoses (two based on eigen decomposition and one based on autoregression). The first algorithm is based on an eigen decomposition-based spectral analysis of the phase of the received ultrasound echo; the second algorithm is based on an eigen decomposition-based spectral analysis of the complex ultrasound echo; and, the third algorithm is based on an autoregressive spectral analysis of the complex ultrasound echo. Since eigen decomposition is a computationally-intensive operation, an approximate eigen decomposition utilizing iterative QR factorization is used as a computationally-efficient algorithm.

Signal Model Developed to Image Vibrations Associated with Stenosed Blood Vessels To model the received signal from vibrating tissue, the tissue being imaged is approximated with S point scatterers having uniform motion and randomly distributed at locations ($\vec{r}_s = [r_s]\hat{e}_r + [\psi_s]\hat{e}_\psi + [\phi_s]\hat{e}_\phi$), s=1 . . . S, in a sample volume where ($\hat{e}_r, \hat{e}_\psi, \hat{e}_\phi$) denote the unit direction vectors in spherical coordinates. The instantaneous position of the scatterers, $v(\vec{r}, t)$, is given by:

$$v(\vec{r}, t) = \sum_s \delta(\vec{r} - \vec{r}_s(t)) \quad (1)$$

$$\vec{r}_s(t)[r_s - d_r(t)]\hat{e}_r + [\psi_s - d_\psi]\hat{e}_\psi + [\phi_s - d_\phi]\hat{e}_\phi$$

where ($d_r(t), d_\psi(t), d_\phi(t)$) denote the displacement as a function of time. If the scattering from the sample volume is uniform with $\alpha$ as the average scattering coefficient, then the scattering function of the sample volume is $\alpha v(\vec{r}, t)$. The complex received signal from the sample volume, $y(\sigma, t)$, can then be modeled as a convolution of the pulse echo spatial impulse response, $h_{pe}(\vec{r}, \sigma)$, of a single point scatterer, the temporal response of the transducer, $x(\sigma)$, and the scattering function, $\alpha v(\vec{r}, t)$.

$$y(\sigma,t) = h_{pe}(\vec{r},\sigma) * x(\sigma) * \alpha v(\vec{r},t) + n(\sigma,t)$$

$$x(\tau) = x_0(\sigma) e^{j2\pi f_0 \tau} \quad (2)$$

where the time indices $\tau$ and t refer to "fast" time and "slow" time, respectively, $f_0$ is the center frequency of the transducer, and $n(\sigma, t)$ is white thermal noise. Combining Eqs. (1) and (2) results in:

$$y(\tau, t) = \alpha \sum_s h_{pe}\left(\vec{r}_s, (t), \tau - \frac{2(r_s - d_r(t))}{c}\right) \quad (3)$$

$$x_0\left(\tau - \frac{2(r_s - d_r(t))}{c}\right) e^{j2\pi f_0\left(\tau - \frac{2(r_s - d_r(t))}{c}\right)} + n(\tau, t)$$

where c is the speed of sound and $$\frac{2(r_s - d_r(t))}{c}$$

is the two-way pulse propagation time between the transducer and each point scatterer. The scatterer displacement for vibrations is small compared to the spatial size of the pulse echo spatial impulse response and the envelope of the transducer response. Thus, the "slow" time variations in the first two terms may be neglected and Eq. (3) can be simplified to:

$$y(\tau, t) = \left\{\alpha \sum_s h_{pe}\left(\vec{r}_s, \tau - \frac{2r_s}{c}\right) x_0\left(\tau - \frac{2r_s}{c}\right) e^{j2\pi f_0\left(\tau - \frac{2r_s}{c}\right)}\right\} e^{j2\pi f_0 \frac{2d_r(t)}{c}} + n(\tau, t) \quad (4)$$

$$= A(\tau) e^{j2\pi f_0 \frac{2d_r(t)}{c}} + n(\tau, t)$$

where $A(\tau)$ is the complex amplitude of the scattered signal. It is apparent that the complex received signal is phase modulated with the instantaneous radial displacement.

If the scatterers in the sample volume are all vibrating radially in a simple harmonic fashion with peak displacement $a_0$ and at a frequency $f_{vib}$, the tissue displacement due to cardiac pulsation, breathing, and other tissue movement (i.e., clutter or noise) relative to the transducer is $d_{tiss}(t)$. This motion will hereinafter be referred to as the "clutter motion."

Then, the combined displacement can be considered to be a superposition, as follows:

$$d = d_r(t) + d_{tiss}(t) + a_0 \sin(2\pi f_{vib} t) \quad (5)$$

An ensemble of ultrasound pulses is transmitted in the same direction at a rate known as the pulse repetition frequency (PRF). Then, the complex received signal from the $m^{th}$ pulse transmission, $v(\tau,m)$, is:

$$y(\tau, m) = A(\tau) e^{j 2\pi f_0 \left( \frac{2 d_{tiss}(mT_{PRF})}{c} + \frac{2 a_0 \sin(2\pi m T_{PRF} f_{vib})}{c} \right)} + n(\tau, m) \quad (6)$$

where $T_{PRF}$ is the pulse repetition interval. The Fourier transform of the phase-modulated complex received signal is a Bessel series:

$$Y(\tau, f) = A(\tau) \left\{ \mathcal{F}\left(e^{j 2\pi f_0 \frac{2 d_{tiss}(mT_{PRF})}{c}}\right) *_f \mathcal{F}\left(e^{j 2\pi f_0 \frac{2 a_0 \sin(2\pi m T_{PRF} f_{vib})}{c}}\right) \right\} + N(\tau, f)$$

$$= A(\tau) \left\{ c(f) *_f \sum_{n=-\infty}^{n=\infty} j^n J_n(\beta) \delta(f - 2\pi n T_{PRF} f_{vib}) \right\} + N(\tau, f)$$

$$= A(\tau) \sum_{n=-\infty}^{n=\infty} j^n J_n(\beta) c(f - 2\pi n T_{PRF} f_{vib}) + N(\tau, f) \quad (7)$$

where $J_i$ are Bessel functions of the first kind, $$\beta = \frac{4\pi f_0 a_0}{c},$$

$\delta$ is the Dirac delta function, and $c(f)$ is the spectrum of the clutter motion (the clutter spectrum), and $N(\tau,f)$ is the noise spectrum.

Figure 2:
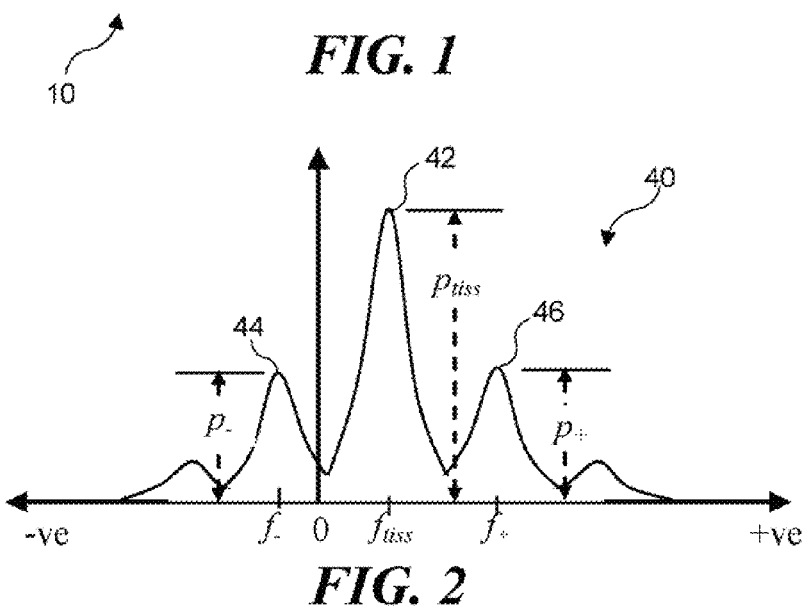
FIG. 2 is a graph of an expected Doppler spectrum (i.e., frequency vs. power) from a vibrating sample volume.

FIG. 2 illustrates a typical power spectrum 40 of the ultrasound signal when a tissue vibration is present. The spectrum includes multiple copies of the clutter spectrum separated by the vibration frequency, as indicated by Eq. (8), which is presented below. A low frequency peak 42 at $f_{tiss}$ corresponds to the clutter spectrum, while symmetric peaks $f_-$ and $f_+$ indicated respectively by reference numbers 44 and 46 correspond to vibration, and $p_{tiss}$, $p_+$, and $p_-$, are the corresponding peak powers. The frequency peaks at $f_+$ and $f_-$ are referred to herein as a "matching pair." For small-amplitude vibrations, higher-order terms can be ignored; thus, most of the spectral energy will be present in the three frequency peaks, $f_-$, $f_{tiss}$, and $f_+$, respectively. Since $$\left| \frac{J_1(\beta)}{J_0(\beta)} \right| \approx \frac{\beta}{2},$$

the ratio of the power in the frequency peaks can provide an estimate of the vibration amplitude. Therefore, the vibration frequency and amplitude may be estimated from the power spectrum as follows:

$$\hat{f}_{vib}^{power} = \left| \frac{f_+ - f_-}{2} \right|; \quad (8)$$

$$\hat{a}_{vib}^{power} = \frac{c}{4\pi f_0} \sqrt{\frac{p_+ + p_-}{2 p_{tiss}}}$$

These estimators are referred to herein as the "spectral frequency estimator" and the "power ratio amplitude estimator," respectively. Alternatively, the vibration frequency and amplitude may be estimated from the residual phase $\{\phi(k)\}_{k=1}^E$ of the ultrasound signal after suppressing the effects of clutter motion. A coarse computationally-efficient estimate of the frequency of the dominant components, $\hat{f}_{vib}$, can be obtained by counting the zero crossings, $N_{zero}$, in the residual phase. This estimate can be further refined by interpolating the residual phase to compute the mean period of oscillation. The vibration amplitude may be estimated by the variance of the residual phase. These estimators are defined as follows:

$$\hat{f}_{vib}^{phase} = \left| \frac{f_+ - f_-}{2} \right|; \quad (9)$$

$$\hat{a}_{vib}^{phase} = \frac{c}{4\pi f_0} \text{var}(\phi(k))$$

and are respectively referred to herein as the "zero-crossing frequency estimator" and the "phase variance amplitude estimator."

For real-time tissue vibration imaging, only a short ensemble of ultrasound data (typically, 6-16 pulses or echoes) from each sample volume in a region of interest may be available for processing. Conventional color-flow imaging systems utilize clutter filtering to suppress the clutter, while retaining the blood flow. However, due to the small number of temporal samples, the conventional clutter filtering-based approach, or a Fourier-based approach lacks sufficient resolution to discriminate between the tissue vibrations, blood flow, and clutter. A parametric approach that utilizes the characteristics of the vibration signal appears better suited to make this distinction. Three parametric approaches may be taken, based on the model of the ultrasound signal in Eqs. (6) and (7), including: (a) estimation of a pair of complex exponentials in noise; (b) autoregressive modeling; and, (c) decomposition of the phase of the ultrasound signal. In the following section, exemplary vibration detection algorithms based on these three parametric approaches are described in greater detail. One method of producing the complex ultrasound signal in Eq. (4) is a quadrature demodulation of the received ultrasound signal. An alternative method is to compute the time delays producing the phase variations in Eq. (4) by processing the received RF ultrasound data using a cross correlation technique.

Vibration Imaging Using Estimation of Complex Exponentials in Noise

Using the inverse Fourier transform of the Bessel expansion in Eq. (7), Eq. (6) is expanded, as follows:

$$y(\tau, m) = A(\tau) \left\{ e^{j 2\pi f_0 \frac{2 d_{tiss}(mT_{PRF})}{c}} \right\} \left\{ \sum_{n=-\infty}^{n=\infty} J_n(\beta) e^{j 2\pi n f_{vib} T_{PRF} + jn\pi} \right\} + n(\tau, m) \quad (10)$$

$$= A(\tau) \left\{ \sum_{n=0}^{n=\infty} J_n(\beta)[e^{j2\pi n f_{vib} T_{PRF}} - e^{-j2\pi n f_{vib} T_{PRF}}] \right\} e^{j2\pi f_0 \frac{2d_{tiss}(mT_{PRF})}{c}} + n(\tau, m)$$

Thus, the ultrasound signal can be modeled as a sum of complex exponentials embedded in noise. As can be seen from the expression enclosed by square brackets in Eq. (10), vibrations correspond to matching pairs of complex exponentials. In contrast, the complex exponentials corresponding to clutter motion will typically not have such matching pairs of frequencies. The frequencies ($f_{tiss}$, $f_+$, $f_-$) may be estimated using the root-MUSIC and ESPRIT algorithms (disclosed by P. Stoica and R. Moses in "*Introduction to Spectral Analysis*," Upper Saddle River, N.J.: Prentice-Hall, 1997). Vibrations may then be detected using a matching peak criterion $|f_+ + f_- - 2f_{tiss}| < F_{threshold}$, and the vibration amplitude and frequency can be estimated using Eq (9), which is set forth above. The steps of the algorithm are described in more detail below, in regard to FIG. 3A. Based on this criterion, vibrations can be detected and distinguished from clutter motion. Any blood flow signals may be considered as part of the noise spectrum.

Figure 3A:
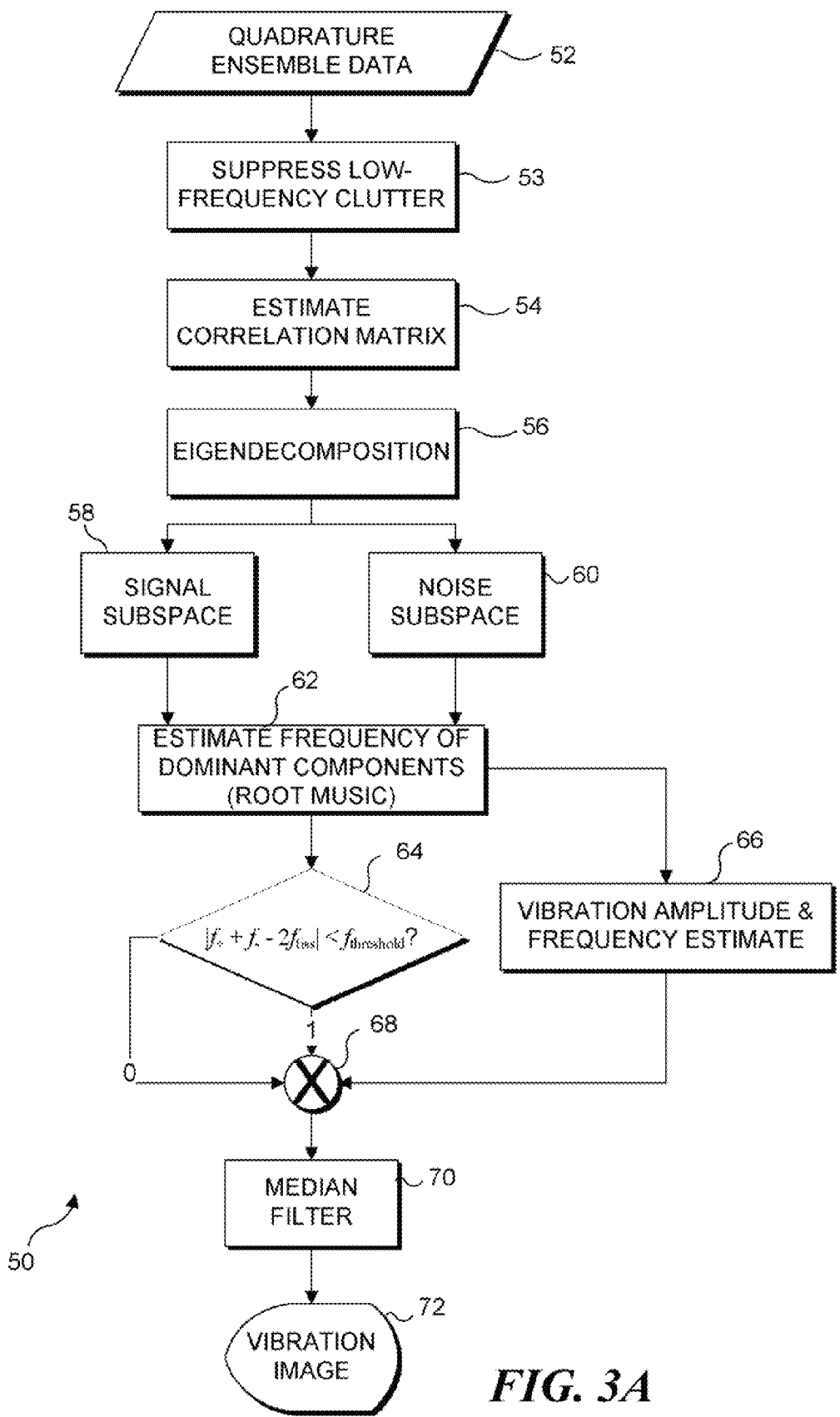
FIG. 3A is a flow chart showing the logical steps of an exemplary subspace-based algorithm for creating a vibrating tissue image in which a stenosis is evident.

FIG. 3A illustrates a flow chart 50 that shows the logical steps involved in a first algorithm for estimating the tissue vibrations based upon a pair of complex exponentials in clutter or noise, which are normally excluded from color-flow processing. The procedure begins with a quadrature-demodulated ensemble of 2D ultrasound data 52.

In a step 53, low frequency clutter due to cardiac pulsation, pulsatile blood vessel wall motion, and respiration is suppressed. In one embodiment, this step may include down mixing with the mean clutter velocity estimated using the autocorrelation method. In another embodiment, the low frequency motion may be suppressed by filtering. In yet another embodiment, the motion of the surrounding tissue may be used to form an estimate of the low frequency tissue motion by analyzing the principal motion components.

In a step 54, a correlation matrix is estimated from the color-flow data. In a step 56, the correlation matrix is employed to carry out an eigen decomposition, producing a signal subspace 58 and a noise subspace 60. Using the signal subspace and the noise subspace, the frequency of the dominant components is estimated in a step 62, by employing the root-MUSIC and ESPRIT algorithms, as noted above. A decision step 64 then determines if each dominant component is double-sided, while a step 66 estimates the vibration amplitude and frequency of each dominant component using Eq. (8). If a dominant component is not double-sided (i.e., is not a potential tissue vibration component), decision step 64 returns a "zero," while if the dominant component is double-sided, the decision step returns a "one." A multiplier 68 then multiplies the output of decision step 64 by the vibration amplitude and frequency estimate for the dominant component, yielding a null if the dominant component is not a tissue vibration component, and otherwise returning the estimate of vibration amplitude and frequency of the dominant component. A median filter 70 then filters isolated falsely-detected vibrations and other undesired noise from the results, so that the remaining vibration image indicating a stenosis site is displayed in a step 72.

Vibration Imaging Using an Autoregressive Signal Model.

The ultrasound signal from vibrations can be modeled as the output of a $p^{th}$-order autoregressive linear prediction filter with white Gaussian noise having a variance $\sigma^2$, as the input, as follows:

$$y(\tau, m) = \sum_{k=1}^{p} a_{m-k}(\tau) y(\tau, m-k) + n(\tau, m) \quad (11)$$

The linear prediction coefficients, $a_k(\tau)$, can be computed using either a least-squares minimization of the prediction errors or using the computationally-efficient Burg algorithm, as explained by Stoica and Moses in the above-referenced paper. A high-resolution spectral estimate can then be obtained from this autoregressive model as follows:

$$\|Y(\tau, f)\| = \frac{\sigma^2}{\left|1 + \sum_{k=1}^{p} a_k(\tau) e^{-j2\pi kf}\right|^2} \quad (12)$$

From Eq. (8), the presence of symmetric matching pairs of frequency peaks in the power spectrum around the clutter motion peak may be detected as a vibration. As before, any flow signals may be regarded as noise. For ultrasound signals from vibrations, the power spectrum in Eq. (13) will have frequency peaks ($f_{tiss}$, $f_+$, and $f_-$) at the local minima of the polynomial $$A(\tau, f) = \left|1 + \sum_{k=1}^{p} a_k(\tau) e^{-j2\pi kf}\right|.$$

Vibrations can be detected using a matching peak criterion $|f_+ + f_- - 2f_{tiss}| < F_{threshold}$ and the vibration amplitude and frequency can be estimated using Eq. (9). The steps of this algorithm are described in more detail below, in connection with FIG. 3B.

Figure 3B:
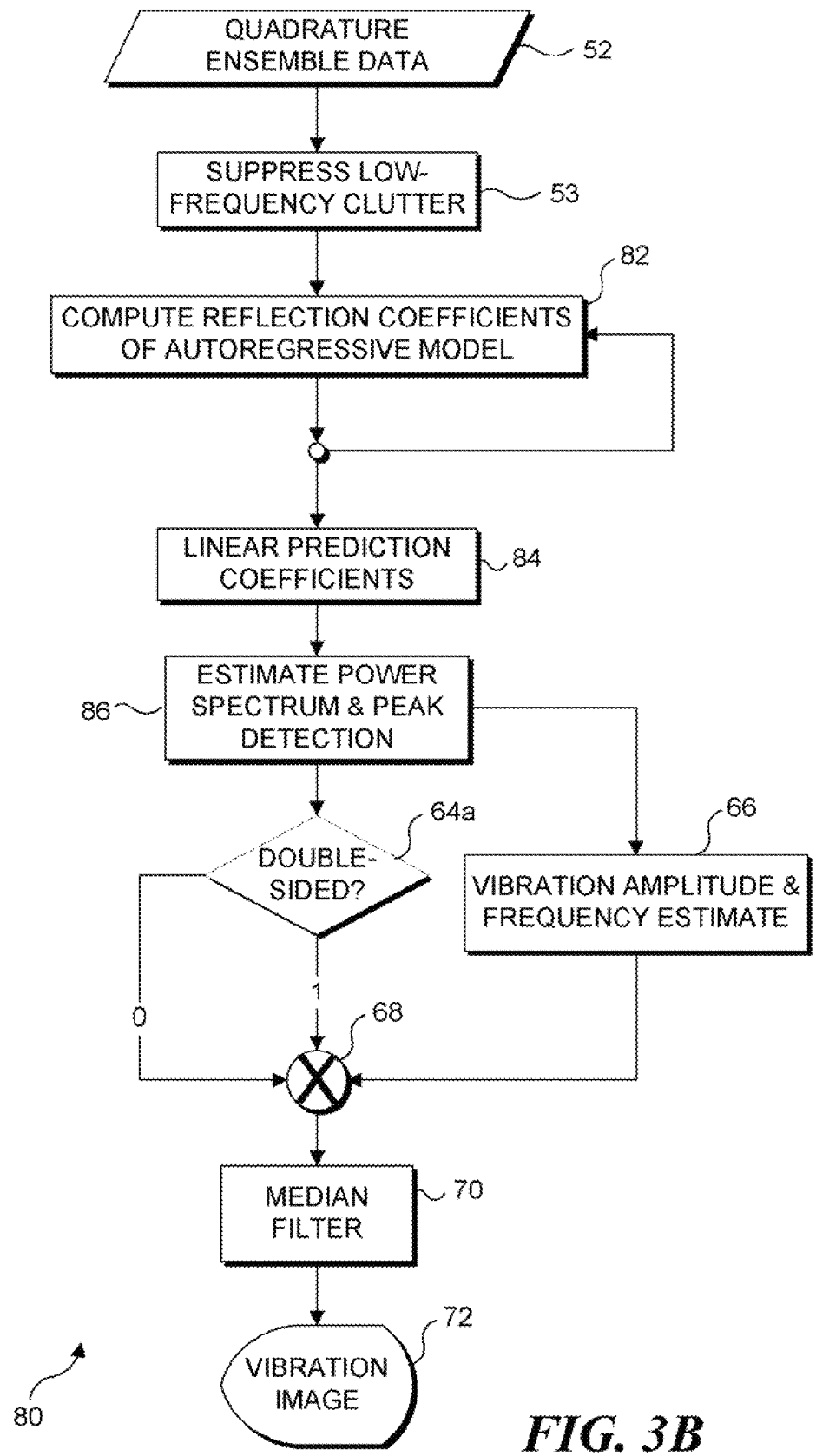
FIG. 3B is a flow chart showing the logical steps of an alternative exemplary algorithm that uses autoregression for creating a vibrating tissue image in which a stenosis is evident.

As shown in a flow chart 80 in FIG. 3B, the second alternative algorithm also begins with quadrature-demodulated ensemble data set 52. Again, in step 53, low frequency clutter due to cardiac pulsation, pulsatile blood vessel wall motion, and respiration is suppressed. In one embodiment, this step may include down mixing with the mean clutter velocity estimated using the autocorrelation method. In another embodiment, the low frequency motion may be suppressed by filtering. In yet another embodiment, the motion of the surrounding tissue may be used to form an estimate of the low frequency tissue motion by analyzing the principal motion components.

In a step 82, reflection coefficients are computed for each ensemble of the quadrature-demodulated data. Using the reflection coefficients, linear prediction coefficients are determined in a step 84. In a step 86, the power spectrum is estimated from the linear prediction coefficients and the peaks in the power spectrum are detected. A decision step 64a determines if the peaks thus identified are for tissue vibration by determining if they are double-sided and returning a zero if not, and a one, if so. Also, step 66 provides for estimating the vibration amplitude and frequency at each of these peaks, and the results from decision step 64a are multiplied by the estimated amplitude and frequency in multiplier 68. Median filter 70 is then applied to the results, and the filtered image data are displayed as a vibration image, in a step 72.

Vibration Imaging Based on Phase Decomposition

A third algorithm for detection and imaging of vibrations can be based on the phase ultrasound signal. As shown in Eq. (7), vibrations will produce an oscillatory signature in the phase, which will typically not be present in the case of clutter motion. Although flow signals may have an oscillatory phase, the echoes from vibrating tissue are expected to be more coherent than those from flow. Thus, their phase may be modeled by a smaller number of dominant components. Accordingly, a vibration detection algorithm can also be based on decomposition of the phase of the ultrasound signal into its dominant components and testing for an oscillatory phase. Alternatively, instead of using quadrature-demodulated ultrasound data, the phase can be estimated from RF ultrasound data by estimating the time delays between a pair of RF ultrasound data.

Any linear time-varying motion is first suppressed by down mixing the ensemble of 2D ultrasound data with the mean clutter velocity, estimated using the conventional autocorrelation method. The phase of the ensemble of 2D ultrasound data is then computed, and the mean phase is subtracted to suppress the effect of the stationary echo. The residual phase is then decomposed into its dominant components using a method similar to principal component analysis. The first step of the decomposition involves the estimation of the correlation matrix of the residual phase using the modified covariance method (Marple, 1987). An approximate eigen decomposition can then be performed using iterative QR factorization of the correlation matrix. The approximate eigen values, 2, may be estimated by the diagonal elements of the upper triangular matrix Rk after the $k^{th}$ iteration. The eigen vectors are arranged in order of decreasing eigen values. The eigen values are a measure of the signal energy contributed by the corresponding eigenvector. Thus, the fraction of the total signal energy contained in the p dominant components can be estimated using:

$$E_p = \frac{\sum_{i=1}^{p} \lambda_i^2}{\sum_{i=1}^{N+1} \lambda_i^2}.$$

Therefore, noise and blood flow can be suppressed by only employing values of $E_p$ that exceed a threshold criterion, $E_p > E_{threshold}$. To further separate tissue vibrations from clutter motion, the fact that tissue vibrations have a higher frequency compared to clutter motion is applied. Vibrations can then be separated from clutter using a frequency threshold criterion $\hat{f}_{vib} > F_{threshold}$ where $F_{threshold}$ is chosen so that at least one half of one period of the vibration is contained in an ensemble. The vibration frequency and amplitude may be estimated using Eq. (10). The steps of this algorithm are described in more detail below, in connection with FIG. 3C. While developed to image vibrations associated with internal bleeding, this exemplary algorithm has also been shown to be effective in imaging vibrations associated with stenosed blood vessels, as is discussed in detail below.

A flow chart 90a illustrates the logical steps of the third algorithm. Again, starting with quadrature ensemble data 52, step 53 suppresses low frequency clutter due to cardiac pulsation, pulsatile blood vessel wall motion, and respiration. In one embodiment, this step may include down mixing with the mean clutter velocity estimated using the autocorrelation method. In another embodiment, the low frequency motion may be suppressed by filtering. In yet another embodiment, the motion of the surrounding tissue may be used to form an estimate of the low frequency tissue motion by analyzing the principal motion components.

A step 94 provides for computing an unwrapped phase of the quadrature ensemble or color flow data, and then subtracting the mean clutter velocity from the unwrapped phase, resulting in a residual phase. As explained above, instead of determining the phase from quadrature-demodulated data, the phase can be determined from RF ultrasound data by estimating time delays between a pair of RF ultrasound data. Using the residual phase, a step 96 estimates a correlation matrix, which is then used to carry out a QR factorization in a step 98a, yielding an eigen value estimate 100a, an eigenvector estimate 102a, and a vibration amplitude and frequency estimate 104a, which are determined using Eq. (10), as noted above. Using the eigen value estimate, a decision step 106a determines if the total energy contained in the p dominant component is greater than a predefined threshold, T. If so, decision step 106 returns a zero, and if not, a one. Similarly, a decision step 108a determines if the estimate eigenvector has a frequency that is greater than a predefined threshold, F. If so, decision step 108a returns a one, and if not, a zero. The results of decision steps 106a and 108a, and the estimated vibration amplitude and frequency of the dominant components are then multiplied together by a multiplier 110, so that if either of the decision blocks has returned a zero, the result is null, but if neither has returned a zero, the estimated vibration amplitude and frequency from step 104a are returned. Again, median filter 70a is applied to the estimated amplitude and frequency, providing filtered results that are displayed as the vibration image, indicating a site of stenosis, in a step 72a.

Using the Algorithms Described Above to Image and Analyze a Stenosis

Figure 4:
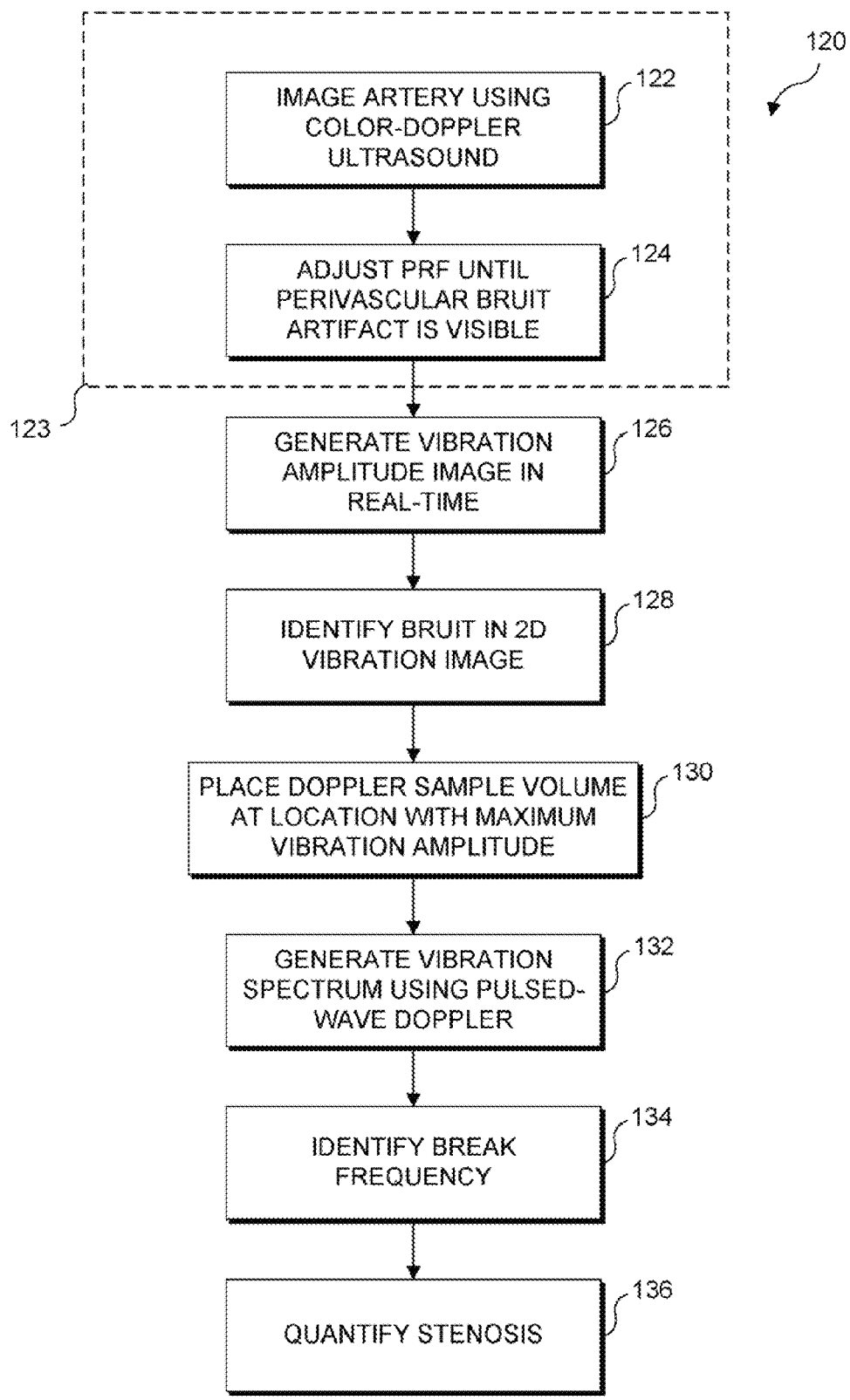
FIG. 4 is a flow chart showing the logical steps of a method for localizing and grading arterial stenoses using a vibrating tissue image generated using ultrasound.

FIG. 4 illustrates a flow chart 120 that shows the logical steps involved in using ultrasound to localize and quantify arterial stenoses. The procedure begins with a step 122, wherein a blood vessel is imaged using color-Doppler ultrasound. In a step 124, the pulse repetition frequency (PRF) is adjusted until a perivascular artifact of a bruit is visible. In a step 126, a vibration amplitude image is generated in real time, generally as described above. In a step 128, the location of the bruit in the 2D vibration image is identified. In a step 130, a Doppler sample volume is placed at the bruit proximate the maximum vibration amplitude. In a step 132, a vibration spectrum is generated from the pulsed-wave Doppler data (again, using the techniques described above). In a step 134 the "break" frequency of the vibration spectrum is noted, while in a step 136 the stenosis is quantified.

A dashed block 123 surrounding steps 122 and 124 indicates that the collection of an echogram (the Doppler image, which is based on reflections of ultrasound energy off of various tissue interfaces) is optional. While collecting a B-mode or Doppler mode ultrasound image can help the operator determine that the ultrasound transducer is positioned properly to collect vibration data from the desired region of tissue, it must be recognized that the vibrometry techniques disclosed herein can be implemented without generating an echogram (i.e., a B-mode or Doppler mode ultrasound image based on reflections from multiple interfaces in the tissue mass). If the operator is sufficiently well versed in anatomy, the operator will be able to place an ultrasound transducer at a location on a patient's skin that will enable the transducer to collect vibration data from the region of tissue including the artery whose condition is to be evaluated. For example, if renal arteries are being evaluated for stenoses, then the transducer will be positioned to direct ultrasound energy into tissue proximate the renal arteries and collect vibrations from a tissue mass surrounding the renal arteries. If cerebral arteries are being evaluated for stenoses, then the transducer will be positioned to direct ultrasound energy into tissue proximate the cerebral arteries and collect vibrations from a tissue mass surrounding the cerebral arteries. Similarly, if cardiac arteries are being evaluated for stenoses, then the transducer will be positioned to direct ultrasound energy into tissue proximate the cardiac/coronary arteries and collect vibrations from a tissue mass surrounding the cardiac arteries. Of course, the positioning of the transducer must take into account anatomical structures (such as bones) that may interfere with the propagation of the vibrations from their source to the transducer. Particularly where the operator is familiar with B-mode or Doppler mode ultrasound imaging, generating such a B-mode or Doppler mode ultrasound image can be used to verify that the transducer is properly positioned, however, the generation of such imagery is not strictly required, and even when implemented, such B-mode or Doppler mode ultrasound imaging is separate and distinct from the step of generating the vibration image.

It should also be recognized that while the concepts herein have been discussed in context of using vibrometry to generate a vibration image, that once the vibration data from the tissue mass has been collected and processed to determine if a stenotic vibration source has been detected in a particular mass of tissue, that an indication of the detection of such a stenotic vibration source can be provided to the operator in a form other than, or in addition to, an image. For example, a flashing light or audible tone can be used to indicate that a stenotic vibration source has been detected in a mass of tissue. Thus, while generating a vibration image (particularly an image that indicates a relative anatomical location of the stenotic vibration source) represents an exemplary embodiment, it should be understood that the vibrometry techniques disclosed herein encompass methods that do not specifically include the step of generating such a vibration image.

One can consider the vibrometry concepts disclosed herein to be similar to a penetrating stethoscope. To use a stethoscope, one places the bell (microphone) at the right location, (head, neck, chest, 3rd right intercostal space, popliteal fossa, etc.) to be near the source of the sound. In the vibrometry concepts disclosed herein, an ultrasound transducer is used as the stethoscope bell, and a processor and algorithm are used to analyze the data (in place of the physician simply listening to the stethoscope).

In the context of using vibrometry to evaluate coronary arteries, an operator who is familiar with the anatomical structure of the heart can ensure that the transducer is properly positioned to detect vibrations from specific coronary arteries. Even if no B-mode image is used to help properly position the transducer, vibrations from the aortic and mitral valve, for instance, can be readily identified (in such an embodiment, those vibrations would not be filtered out initially, to allow the operator to use those vibrations as reference points, recognizing that such vibrations will then be filtered from the signal collected by the transducer, as such vibrations would make detection of a stenosis difficult). From knowledge of anatomy, the operator will recognize that the left main coronary artery is in (or near) the plane of the aortic and mitral valves. Thus, even without being able to visualize the location of the left main coronary artery in a B-mode ultrasound image, an operator sufficiently familiar with anatomy will be able to interrogate the correct mass of tissue proximate the artery, even though the operator cannot see a B-mode image of the artery.

Selecting an appropriate location for the transducer to evaluate stenoses in other arteries can be similarly achieved based on anatomical knowledge. As will be discussed in detail below, at least one embodiment disclosed herein includes a targeting jig that enables operators with only minimal anatomical knowledge to properly position the transducer to detect stenoses in specific arteries.

Detectable Vibration Amplitudes and Frequencies

In experiments using a physical phantom model, tissue vibrations with a peak amplitude of about 1 µm have been accurately detected. The minimum detectable vibration amplitude depends upon the noise level and dynamic range of the phase of the received ultrasound echo. In modern ultrasound machines, the phase can have a dynamic range of 96 dB or more (for 16-bit quadrature-demodulated data) and the signal typically exceeds the electronic and thermal noise level by 80 dB or more. Therefore, from Eq. (4), vibrations as small as 50 nm may theoretically be detected using a 5 MHz ultrasound transducer. Practically, the attenuation of the ultrasound signal will reduce the dynamic range and limit the minimum detectable amplitude in deep tissue to ~0.5 µm.

The detectable vibration frequencies depend upon the choice of PRF, i.e., on $F_{PRF}$. A PRF that is too low compared to the vibration frequency would lead to aliasing, while selecting a PRF that is too high will fail to detect low-frequency vibrations. A vibration can be detected only if at least half of one vibration cycle is captured within the temporal window corresponding to an ensemble. Thus, all vibrations with frequency between $$\frac{F_{PRF}}{2*E} \text{ and } \frac{F_{PRF}}{2}$$

can be detected theoretically without aliasing for an ensemble size E. Since vibrations can be broadband, a high-frequency vibration interrogated at a low PRF value can be mistaken for noise using this algorithm. Thus, for better sensitivity, it is desirable to select a PRF and an ensemble size so that only a few periods of the vibration are included in the ensemble. Accordingly, the maximum detectable frequency is $$\frac{kF_{PRF}}{E}$$

when k periods of the vibration are included in an ensemble. A simulation and phantom experiments that were carried out indicate that reliable detection may be performed using only one half to six vibration periods during the interrogation period. For example, with a PRF of 1 kHz and an ensemble size of 16 periods/pulses, vibrations with frequency between 31.3 Hz and 375 Hz may be reliably detected.

Quantification of Residual Lumen Diameter

Since the tissue vibrations are produced by the blood flow eddies, the frequency of the tissue vibrations is the same as the frequency of the eddies. The frequency spectrum of the vibrations depends upon the effective diameter of the turbulent jet, thus, the bruit spectrum is related to the severity of the stenosis. The bruit spectrum exhibits a peak frequency beyond which the energy falls off rapidly with increasing frequency. The Strouhal number (S) relates the break frequency of turbulent fluctuations ($f_{vib}$) to the length scale of the turbulence (the residual lumen diameter at the stenosis (D) and the mean downstream blood velocity in the unobstructed vessel (U)) according to:

$$S = \frac{f_{vib} \times D}{U} \quad (13a)$$

It has been empirically observed in carotid artery stenoses that at the break frequency, the product of the carotid artery flow velocity and the Strouhal number remains relatively constant at about 500 mm/s in most individuals. Therefore, a simple relationship exists between the break frequency and the residual lumen diameter:

$$d - \frac{500}{f_b} \quad (13b)$$

In arteries other than the carotid artery, the flow velocity can be estimated using pulsed-wave Doppler. The break frequency can be then used to quantify the residual lumen diameter at the stenosis, assuming the Strouhal number remains constant at a value of 1.

Furthermore, the ability to directly measure the amplitude of the vibrations enables a stenosis to be graded. The energy in the eddies (F) and thus, the amplitude of the tissue vibrations ($a_{vib}$), is directly proportional to the flow rate, as follows:

$$E \propto a_{vib}^2 \propto U^2 \quad (14)$$

Heretofore, other techniques of analyzing bruits (such as auscultation, phonoangiography and phonocardiography) have not been able to directly measure the amplitude of wall vibrations associated with stenoses. The ability to directly measure the amplitude of the vibrations enables the quantification of other parameters associated with stenosis and corresponding vibrations, such as acoustic power, pressure drop across the stenosis (e.g., in the coronary arteries), and flow power dissipation. Empirical data collected from stenosed blood vessels using such techniques can be analyzed to identify stenosis profiles indicative of hemodynamically significant stenoses. It should also be recognized that 3D ultrasound imaging would facilitate providing an accurate localization of a stenosis. For example, such imaging will facilitate determining with which of the three major coronary arteries a stenosis is associated.

Sources of Artifacts

In color-flow data acquisition, interrogation along each scan line is performed for only a brief period of time. Vibrations are transient, with typical durations of 10 ms-100 ms. Thus, there is a possibility that some vibrations may not be interrogated. Since the vibrations typically have a relatively large spatial extent and repeat every cardiac cycle, it is unlikely that the vibrations will be missed entirely; however, the spatial extent of the vibrations visible in the image may be only a part of the true spatial extent. By appropriately choosing the PRF and the region of interest, such discrepancies may be minimized.

Other artifacts may be falsely detected as vibrations. Transducer motion may introduce additional frequency peaks in the clutter spectrum and may cause false detections; however, using a trained sonographer to perform the scanning may minimize these false detections. Vibrations in the tensed skeletal muscle of the sonographer, and any ambient vibrations may be detected in the vibration image. In addition, the high-resolution spectral estimation methods may produce spurious peaks that can be falsely detected as vibrations. Such artifacts can be easily distinguished from pathological vibrations, which are expected to be correlated with the anatomy and periodic with every cardiac cycle. These artifacts can be also avoided if additional temporal samples are available. Any vibrations displayed in the vibration image should therefore be confirmed with the vibration spectrum by placing a Doppler sample volume at the location of the peak intensity.

Comparison of the Algorithms Derived from Modeling

The ability of the proposed algorithms to detect vibrations was evaluated using a simulation model. Simulations show that subspace-based algorithms such as MUSIC and ESPRIT have high sensitivity (96%) and specificity (98%) for detecting narrowband vibrations in the presence of clutter as well as blood flow and are robust even when broadband vibrations are present. For narrowband vibrations, an algorithm based on an autoregressive model has a slightly improved specificity (99%), a comparable sensitivity, and is robust to broadband vibrations. The phase decomposition-based algorithm has a slightly lower sensitivity (93%) and specificity (98%), but is more robust to broadband vibrations.

The computational requirements of the proposed algorithms are shown below in Table 2. The subspace-based algorithms (MUSIC/ESPRIT) have a computational requirement that is highly dependent on the choice of model order. In these algorithms, eigen decomposition is the most computationally-intensive task. The autoregression-based algorithm is less computationally intensive, and the computational requirement is less dependent on the model order. In this case, the computation of the FFT for spectral estimation is the most computationally-intensive task. The phase decomposition method is the least computationally intensive, since it involves operations on real signals only. Thus, the phase-decomposition algorithm is most suitable for real-time implementation.

TABLE 1

Field II Simulation Parameters

| | |
|---|---|
| Center frequency | 5 MHz |
| PRF | 500 Horizontal |
| Transducer excitation | 5-period sinusoid |
| Transducer impulse response | Hanning-weighted 2-period sinusoid |
| f number | 2 |
| Number of elements | 192 |
| Transducer height | 15 mm |
| Element pitch | 0.4 mm |
| Element kerf | 0.03 mm |
| Transmit aperture | 25.6 mm |
| Receive aperture | 25.6 mm |
| Transmit focus | 40 mm |
| Receive focus | 30 mm to 100 mm in steps of 10 mm |
| Elevation focus | 20 mm |
| Mathematical element size | 0.37 mm × 1.5 mm |
| Sampling frequency | 105 MHz |
| Sound velocity | 1540 m/s |
| Number of scan lines | 32 |
| Number of ensembles | 10 |

TABLE 2

Computational requirement (million operations/sec) for real-time imaging at 10 frames/s with 32 scan lines, 256 samples/scan line, and ensemble 10

| | Model Order | | |
|---|---|---|---|
| Algorithm | p = 2 | p = 3 | p = 4 |
| MUSIC | — | 3631 | 7653 |
| ESPRIT | — | 2218 | 6455 |
| AR | — | 1606 | 1630 |

TABLE 2-continued

Computational requirement (million operations/sec) for real-time imaging at 10 frames/s with 32 scan lines, 256 samples/scan line, and ensemble 10

| Algorithm | Model Order | | |
|---|---|---|---|
| | p = 2 | p = 3 | p = 4 |
| Phase-decomposition | 181 | 489 | 1107 |
| Color flow | | 89 | |

2D Fourier Transform Processing for Improved Tissue Motion Spectrum

FIG. 5A graphically illustrates both a 2D Fourier (2D FFT) spectrum and a conventional Doppler spectrum of simulated received ultrasound echoes when scatterers responsible for the echoes are moving with constant velocity of 20 mm/s, with the Doppler spectrum being disposed to the left of the vertical axis, and the 2D FFT spectrum being disposed on the right of the vertical axis. The motion of the scatterers represented here is axially along a direction of an ultrasound beam. Note the spectrum of the received pulse lies on a line that passes through the origin with slope:

$$\frac{f_{tiss}}{f_{RF}} = \frac{2v_{tiss}}{c} = 2.59 \times 10^{-5} \quad (15)$$

The peak in the Doppler spectrum (on the left of the vertical axis) corresponds to the Doppler shift of $$\frac{2f_0 v_{tiss}}{c} = 129 \text{ Hz},$$

as indicated by a line 21.

FIG. 5B graphically illustrates both a 2D Fourier (2D FFT) spectrum and a conventional Doppler spectrum of simulated received ultrasound echoes when scatterers responsible for the echoes are moving with constant velocity of 20 mm/s and also vibrating with a frequency of 300 Hz and an amplitude of 5 μm, with the Doppler spectrum being disposed to the left of the vertical axis, and the 2D FFT spectrum being disposed on the right of the vertical axis. From Eq. (8), the presence of a vibration causes a Bessel modulation of the received signal, which generates multiple copies of the spectrum illustrated in FIG. 5A, on lines parallel to a line through the origin, and offset with respect to each other by $f_{vib}$. The conventional Doppler spectrum (i.e., on the left of the vertical axis in FIG. 5B) shows the corresponding peaks that are respectively at frequency of 129+300=429 Hz (as indicated by line 23) and 129−300=171 Hz (as indicated by arrow 25).

Several insights can be obtained from this 2D spectral formulation of the simulated received echoes. A first observation is that the spectral spread of the Doppler spectrum depends upon the Doppler shift. This point can be further appreciated from the 2D FFT in the case of a high scatterer velocity of 200 mm/s, as graphically illustrated in FIG. 6A, which includes both a 2D FFT spectrum and a conventional Doppler spectrum of received ultrasound echoes (where the center frequency of the transmitted ultrasound signal is 5 MHz) when scatterers responsible for the echoes are moving with constant velocity of 200 mm/s and also vibrating with a frequency 300 Hz, at an amplitude of 5 μm. In this case, the Doppler spectrum is disposed to the left of the vertical axis, and the 2D FFT spectrum is disposed on the right of the vertical axis. For this example, although the parallel harmonic bands are visible in the 2D FFT spectrum, the large spread in the Doppler spectrum almost completely obscures the vibration pattern. FIG. 6B depicts the same situation when a lower ultrasound center frequency of 2 MHz is used for interrogation (i.e., for both a 2D FFT spectrum and a conventional Doppler spectrum of received ultrasound echoes) and when scatterers responsible for the echoes are moving with constant velocity of 200 mm/s, and also vibrating with a frequency 300 Hz, at an amplitude of 5 μm. The Doppler spectrum is disposed to the left of the vertical axis, and the 2D FFT spectrum is disposed on the right of the vertical axis. Note that since the Doppler shift of the 2 MHz ultrasound frequency of FIG. 6B is lower, the spread in the Doppler spectrum in FIG. 6B is reduced as compared to the spread in the Doppler spectrum of FIG. 6A, and the symmetric vibration signature is partially visible. Therefore, for analyzing vibrations in rapidly moving tissue, such as the cardiac wall, a lower frequency should be chosen for the transmit pulse of the interrogating ultrasound wave.

Another insight relates to recognizing that tissue acceleration causes a broadening of the 2D FFT spectrum. In cardiac tissue, acceleration can range from 0-10 m/s². FIG. 7A graphically illustrates both a 2D Fourier (2D FFT) spectrum and a conventional Doppler spectrum of simulated received ultrasound echoes from a group of scatterers accelerating from 10 mm/s to 30 mm/s within the interrogation window (i.e., with an acceleration of 5 m/s²), with the Doppler spectrum being disposed to the left of the vertical axis, and the 2D FFT spectrum being disposed on the right of the vertical axis. The conventional Doppler spectrum (i.e., the spectrum to the left of the vertical axis), shows a significant spectral broadening, even with a 2-MHz transmit pulse. Further, FIG. 7B graphically illustrates both a 2D FFT spectrum and a conventional Doppler spectrum of simulated received ultrasound echoes from a group of scatterers accelerating from 10 mm/s to 30 mm/s within the interrogation window (i.e., with an acceleration of 5 m/s²), when the scatterers are also vibrating with a frequency 300 Hz and an amplitude of 5 μm, with the Doppler spectrum being disposed to the left of the vertical axis, and the 2D FFT spectrum being disposed on the right of the vertical axis. FIG. 7B indicates that when a vibration is present in accelerating tissue, the high acceleration can significantly obscure the vibration spectrum. Thus, it is important to preprocess the received ultrasound data to suppress the effect of tissue acceleration.

The phase of the received ultrasound signal as described in Eq. (5) is influenced primarily by the axial component of the displacement. If the tissue were perfectly homogeneous, the phase would remain unchanged for any motion orthogonal to the axial direction. However, due to the non-homogeneous nature of many tissues, there is a change in the phase as well as the amplitude of the received signal, even for the lateral and elevation components of motion. Thus, off-axis motion components do affect the received signal. The presence of transverse velocity components will result in a broadening of the spectrum, which is proportional to the magnitude of the transverse velocity component. Transverse vibration components will cause a similar broadening of the spectrum. In particular, this broadening implies that even if the vibration occurs in a direction perpendicular to the beam axis, the harmonic Bessel bands indicative of vibrations will still be present in the Doppler spectrum. FIG. 8A graphically illustrates both a 2D FFT spectrum and a conventional Doppler spectrum of simulated received ultrasound echoes when scatterers responsible for the echoes are moving with a constant velocity of 20 mm/s, the scatterer motion being perpendicular to the axis of the ultrasound beam, with the Doppler spectrum being disposed to the left of the vertical axis, and the 2D FFT spectrum being disposed on the right of the vertical axis. Note that the Doppler spectrum shows no Doppler shift, but exhibits a broadening that is proportional to the scatterer velocity. FIG. 8B graphically illustrates both a 2D FFT spectrum and a conventional Doppler spectrum of simulated received ultrasound echoes when scatterers responsible for the echoes are moving with a constant velocity of 20 mm/s, the scatterer motion being perpendicular to the axis of the ultrasound beam, where the scatterers are also vibrating with a frequency of 300 Hz, at an amplitude of 5 µm. In this Figure, the Doppler spectrum is disposed to the left of the vertical axis, and the 2D FFT spectrum is disposed on the right of the vertical axis. Note that the harmonic bands characteristic of vibrations can clearly be seen at a frequency of 297 Hz, as indicated by an arrow 27. Therefore, not only is it possible to detect vibrations perpendicular to the beam axis, it is also possible to accurately estimate the vibration frequency. This important characteristic of vibrations offers a significant advantage over conventional duplex ultrasound, where an accurate velocity estimate is highly dependent upon the orientation of the ultrasound beam with respect to the velocity of the moving blood.

As shown in FIGS. 5A-7B, the conventional Doppler spectrum can have a large spectral variance depending upon the Doppler shift and tissue acceleration. Another artifact in conventional Doppler processing is a granular speckle pattern that is produced due to random phase shifts produced by constructive and destructive interference of scattering from multiple scatterers in the sample volume. Speckle artifacts and large variance can mask the underlying harmonic spectral signatures that are associated with vibrations. Such effects are more pronounced when the tissue motion and acceleration are large, such as in the case of cardiac wall motion, which is an important limitation of conventional Doppler processing with respect to analyzing vibrations in the cardiac wall.

Wideband Doppler estimation techniques can reduce the inherent spectral broadening introduced by conventional Doppler spectral processing. As indicated in FIGS. 7A and 7B, the spectral variance is primarily due to the bandwidth of the transmitted signal. Wideband estimation techniques utilize the bandwidth of the transmitted signal to estimate the Doppler shift and thus can reduce the spectral broadening. Such wideband estimates can also reduce the speckle noise, since the contributions from the sample volume are analyzed separately. Several wideband estimation techniques have been proposed, such as Wideband Maximum Likelihood Estimator (WMLE) (Ferrara and Algazi, "*A new wideband spread target maximum likelihood estimator for blood velocity estimation*," IEEE Trans Ultrason Ferroelect Freq Contr. 1991; 38:1-16), the Wideband Cross-correlation Estimator (WCCE) (Bonnefous and Pesque, "*Time domain formulation of pulse-Doppler ultrasound and blood velocity estimation by cross correlation*," Ultrason Imaging, 1986; 8:73-85) and the 2D FFT estimator (Wilson, "*Description of broad-band pulsed Doppler ultrasound processing using the two-dimensional Fourier transform*," Ultrason Imaging, 1991; 13:301-15). The 2D Fourier transform is of particular interest, since vibrations have a unique signature in the 2D spectrum.

For estimating blood velocity, the Radon transform has been proposed to estimate the slope of the line in the 2D Fourier transform domain (Munk and Jensen. "*A new approach for the estimation of axial velocity using ultrasound*," Ultrasonics, 2000; 37:661-5). The velocity spread can be obtained by looking at the ρ=0 axis in the Radon transform (ρ-θ domain). In the current approach, this method is adapted for identifying vibrations in the tissue surrounding stenosed blood vessels. Based on FIGS. 5A-5B, the Radon transform domain can be interpreted as a mapping between the normalized Doppler shift $$\frac{f_{tiss}}{f_{RF}},$$

and the frequency shift $f_{vib}$.

FIG. 9A graphically illustrates a Radon transform of the 2D FFT spectrum of FIG. 5A. A peak is seen at the normalized Doppler shift of $2.59 \times 10^{-5}$, at a zero frequency shift. FIG. 9B graphically illustrates a Radon transform of the 2D FFT spectrum of FIG. 5B. Multiple copies of the peak at $2.59 \times 10^{-5}$ can now be seen at different frequency shifts. The corresponding Doppler spectra can be extracted from the Radon transform by plotting the intensities corresponding to all the frequency shifts at the peak Doppler shift. FIGS. 9C and 9D graphically illustrate the corresponding Doppler spectra computed from the Radon transforms of FIGS. 9A and 9B. Compared to the Doppler spectra in FIGS. 5A and 5B, the spectral spread is significantly reduced. The vibration peaks occur at the frequency of ±278 Hz (a 7.3% error compared to the actual value of 300 Hz), as indicated by arrows 29 in FIG. 9D. The difference between the tissue motion peak (indicated by an arrow 31) and the first vibration peak (arrows 29) is 4.9 dB, which corresponds to an estimated vibration amplitude of 7.9 nm (a 58% error compared to the actual value of 5 nm).

An alternative blood velocity estimator can be derived from the 2D FFT spectrum by combining appropriately scaled Doppler spectra corresponding to the whole range of frequencies in the transmitted bandwidth (Loupas and Gill, "*Multifrequency Doppler: Improving the quality of spectral estimation by making full use of the information present in the backscattered RF echoes*," IEEE Trans Ultrason Ferroelect Freq Contr., 1994; 42:672-88). The estimated velocity spectra from this method is given by $$P_{MF}(f_{DOP}) = \frac{\int_{f_0-BW/2}^{f_0+BW/2} |Y(f_{RF}, f_{DOP})|^2 \, df_{RF}}{\int_{f_0-BW/2}^{f_0+BW/2} |Y_0(f_{RF}, f_0)|^2 \, df_{RF}} \quad (16)$$

where $f_0$ is the center frequency, BW is the bandwidth of the transmitted pulse, $f_{RF}$ and $f_{DOP}$ are the spatial and temporal frequency in the 2D FFT domain, respectively, and $Y(f_{RF}, f_{DOP})$ and $Y_0(f_{RF})$ are the Fourier transforms defined in Eq. (7). This estimate is referred to as the "multifrequency estimate." The multifrequency estimate improves the velocity resolution, since the large statistical fluctuations introduced by the integration over a sample volume are avoided. In the present disclosure, these techniques have been adapted for identifying vibrations in the tissue surrounding a stenosed blood vessel. The multifrequency estimates computed from FIGS. 5A and 5B using 1-MHz bandwidths are respectively illustrated in FIGS. 10A and 10B. The tissue motion peak is at 125 Hz, as indicated by an arrow 33 (in FIGS. 10A and 10B), which corresponds well with the expected Doppler shift of 129 Hz. The first vibration peaks are at -172 Hz and 422 Hz, respectively (as indicated by arrows 35 in FIG. 10B), resulting in an estimated vibration frequency of 297 Hz, according to Eq. (13) (a 1% error compared to the actual value of 300 Hz). The difference between the low-frequency peak and the first vibration peak is 6.5 dB, which corresponds to an estimated vibration amplitude of 5.48 µm (a 9.6% error compared to the actual value of 5 µm).

As shown above, the multifrequency estimate provides a more accurate estimate of the vibration amplitude and frequency as compared to the Radon transform. The Radon transform estimate automatically corrects for the Doppler shift due to mean tissue motion, whereas this Doppler shift is preserved in the multifrequency estimate. The spectral spread of the multifrequency estimate is similar to that of the Radon transform estimate. However, the additional computational burden of computing the Radon transform makes the estimate based on the Radon transform less desirable than the multifrequency estimate.

Validation of Ultrasound Vibration Imaging of Stenoses Using a Simulation Model

To evaluate the proposed stenosis vibration detection algorithms, a simulation model of vibrations in a blood vessel wall was developed. FIG. 11A schematically illustrates the simulation model (i.e., a 3D model of scatterer distributions) used in the validation. The ultrasound simulator Field II (Jensen 1996) was used to compute the pulse echo spatial impulse response, $h_{pe}(·)$, and the transducer temporal response, $x_0(·)$. The scattering amplitudes, $\alpha_s$, and mean positions, $r \rightarrow_s$, were randomly assigned from a Gaussian distribution with the scattering strength from the vessel wall 40 dB higher than that from blood. The instantaneous scatterer positions, $v(r \rightarrow, t)$, were estimated using the phase of the Doppler ultrasound signal from the vessel wall of a normal human femoral artery, as is graphically illustrated in FIG. 11B. The motion was defined as being in a direction perpendicular to the vessel wall with a peak displacement of 0.08 mm. Vibrations were generated in one region of the vessel wall, with motion in a direction perpendicular to the vessel wall, with the peak amplitude of 5 µm and a frequency of 100 Hz. The clutter motion with vibrations is graphically illustrated in a box 180 of FIG. 11B. The vibration, $d_r^{vib}(t)$ was modeled as a Gaussian-weighted sinusoid with additive white Gaussian noise at different signal-to-noise ratios (SNR), as follows:

$$d_r^{vib}(t) = a_0 \sin(2\pi f_{vib} t) e^{A_5} \left( \frac{1 + \beta_{SNR} n(t)}{1 + \beta_{SNR}} \right), \quad (17a)$$

$$A_5 = \frac{(t - t_{position})^2}{2 t_{duration}^2} \quad (17b)$$

where $t_{position}$ and $t_{duration}$ are the position and duration of the vibration in the cardiac cycle $\beta_{SNR}$ is the SNR of the white Gaussian noise $n(t)$. The addition of Gaussian noise simulates broadband vibrations expected to be produced by blood flow eddies and turbulent flow. The vibration frequency was 100 Hz and $\beta_{SNR}$ was varied from 0 to 2.

Signals from blood were considered to be part of the noise spectrum in both the primary algorithms. To further validate that signals from flow would not be falsely detected as vibrations, blood flow was also simulated in the validation model of FIG. 11A. The motion of scatterers corresponding to blood was generated using the model of flow in a human femoral artery proposed by Jensen (1996). The blood flow introduced into the model is parabolic with a peak velocity of 50 cm/s. The time-varying velocity profile of the simulated blood flow is graphically illustrated in FIG. 11C.

The Field II simulation parameters have been noted above in Table 1. The simulated radiofrequency (RF) lines obtained were demodulated to obtain the in-phase (I) and quadrature (Q) data, and these were decimated to obtain the raw color-flow data. The vibration detection performance was evaluated with different threshold values to measure the sensitivity and specificity. For the phase-decomposition algorithm, the threshold value, $E_{thresh}$, indicates the % of energy in the dominant components for a signal to be considered as vibrations. For the root-MUSIC-based algorithm (i.e., the algorithm based on estimating complex exponentials in noise), the threshold value, $F_{thresh}$, indicates the maximum difference in frequency of a matching pair of complex exponentials. Simulations were performed with different threshold values and different model orders, and receiver-operating characteristic (ROC) curves were generated to evaluate the detector performance. The ROC curves can then be used as a guideline for choosing the appropriate threshold setting and model orders. For the phase-decomposition algorithm, the pth order model had a $2(p+1) \times 2(p+1)$ correlation matrix, with $2 \leq p < E/2$ for an ensemble size of E. Two dominant components were considered for vibration detection. For the root-MUSIC algorithm, the model order p was chosen so that $3 \leq p < E/2$ to enable detection of a matching pair of exponentials, and the estimated correlation matrix size was $2p \times 2p$ (Stoica and Moses 1997).

FIG. 12A is a vibration amplitude image overlaid on a B-mode image using a black-green colormap. The colormap is calibrated according to the values of the estimated amplitude. To quantitatively evaluate the proposed algorithms, two masks (graphically illustrated in FIG. 12B) were generated, V corresponding to regions where vibrations were simulated, and NV corresponding to regions where no vibration is present. Because the scatterers have a time-varying motion, the masks are appropriately generated spatially to ensure that no vibrating scatterers are present in region NV. The percentage of pixels correctly detected as vibrations in region V are counted as true-positives, and the percentage of pixels detected as vibrations in region NV are counted as false-positives.

The sensitivity, specificity and ROC curves for the two primary algorithms discussed above (the phase decomposition algorithm and the algorithm based on estimating complex exponentials in noise) using different model orders are graphically illustrated in FIGS. 13A-13F. FIG. 13A indicates that, for the phase-decomposition algorithm shown in FIG. 3A, the sensitivity decreases with the increasing threshold value for all model orders, because more true vibrations are rejected with larger threshold values. Lower model orders have higher sensitivity, because the correlation matrix is smaller; thus, a better estimate can be obtained using the limited number of temporal samples.

FIG. 13B shows that the specificity is quite similar for all the model orders and increases with increasing threshold value, because a larger threshold leads to better noise rejection. Upon closer investigation, it was determined that the majority of false detections occur when the blood flow velocity is low and the clutter-to-blood signal ratio is high. In such cases, the I-Q Doppler signals from blood can be almost indistinguishable from those of a small-amplitude tissue vibration. The ROC curves for different model orders are graphically illustrated in FIG. 13C, which indicates that a sensitivity of 96% and a specificity of 98% can be achieved with a second-order model. To choose an appropriate threshold value, an operating point is selected in the ROC curve. The corresponding threshold value can then be found from FIG. 13A or 13B.

FIG. 13D shows that, for the root-MUSIC-based algorithm shown in FIG. 3A, the sensitivity increases with the increasing frequency threshold value for all model orders, as more true vibrations can be detected if the frequency threshold is increased.

FIG. 13E shows that the specificity decreases with increasing threshold values, because more false detections occur with increased frequency threshold. The fourth-order model has slightly better sensitivity and specificity due to better modeling of the clutter space.

The ROC curves for the root-MUSIC-based algorithm are graphically illustrated in FIG. 13F. For the third-order algorithm, a sensitivity of 97% and a specificity of 98% are achievable, whereas, for the fourth-order algorithm, the sensitivity can be increased to 98%, with a specificity of 99%.

Figure 3C:
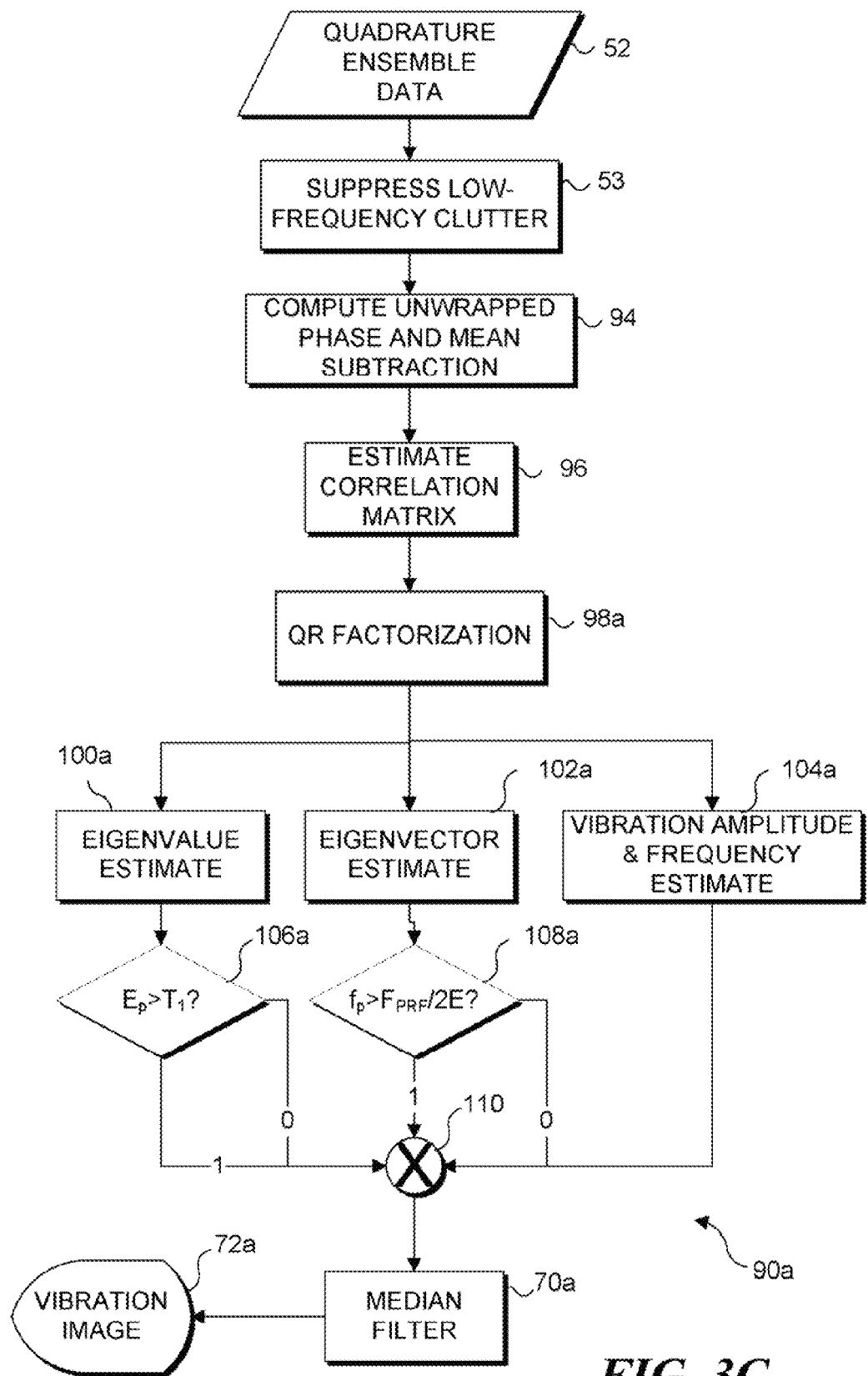
FIG. 3C is a flow chart showing the logical steps of yet another exemplary alternative algorithm that uses phase decomposition for creating a vibrating tissue image in which a stenosis is evident.

The variation in the sensitivity with increasing vibration band width is graphically illustrated in FIG. 14, which indicates that both the phase-decomposition algorithm of FIG. 3C (indicated by a line 200) and the root-MUSIC algorithm of FIG. 3A (indicated by a line 202) can achieve similar sensitivity when the vibration is narrowband ($\beta_{SNR}$=0). As the vibration bandwidth is increased, the sensitivity decreases for the root-MUSIC algorithm (line 202) because it is based on modeling the vibrations as complex exponentials with narrow bandwidth. On the other hand, the phase-decomposition algorithm (line 200) is more robust to the vibration bandwidth because it makes no a priori assumptions about the vibration bandwidth characteristics.

Tissue Vibration Imaging System

For tissue vibration imaging to be clinically useful, real-time visualization of vibrations is quite desirable. Programmable ultrasound signal and image-processing systems using high-performance multimedia processors to support all the conventional processing modes, such as B, M, color flow, and Doppler are available in software. The main strength of a programmable system is the ease of development of new modes and applications without the need for new hardware or making hardware modifications to conventional ultrasound machines. Such programmable ultrasound machines allow access to and processing of internal raw color-flow and pulsed-wave (PW) Doppler quadrature data, and facilitate implementing the phase-decomposition algorithm discussed above for tissue vibration imaging in real time.

The phase-decomposition algorithm has already been empirically tested in a software-programmable ultrasound system for online visualization of vibrations during 2D ultrasound scans. Currently, tissue vibration imaging can be achieved at 9.1 frames/s for 32 scan lines with an ensemble size of 10 and 256 samples per scan line. The computational power of ultrasound machines has increased significantly in recent years, benefiting from advances in processor technology, and this trend is expected to continue in the future. Many modern processors targeted for multimedia applications have specialized instructions that can perform complex multiplications and additions with the same computational overhead as real multiplications and additions. Using such processors, the computational burden to support the algorithms disclosed herein can be reduced by a factor of three or four. Thus, the additional computational burden of the tissue-vibration imaging algorithms disclosed herein can be reasonably supported in modern ultrasound machines.

Experimental Validation

FIG. 15 schematically illustrates a test system including a physical phantom (i.e., a vibrating plate) used for validating the vibration-imaging algorithms discussed above. A piezoelectric plate 182 is incorporated into a test vessel including walls 183 and a plastic base 181. The piezoelectric plate is logically coupled with a function generator 194. The test vessel is filled with water 184. An ultrasound probe 186 (logically coupled to an ultrasound scanner 192), and a fiber optic micrometer 188 (logically coupled to an oscilloscope 190) are disposed in the water bath (i.e., in the test vessel filled with water) proximate the piezoelectric plate, which was vibrated at frequencies between 100 Hz and 800 Hz using a sinusoidal signal from function generator 194. The amplitude of the vibrating plate was calibrated using fiber optic micrometer 188 for different drive voltages corresponding to peak plate displacements of 1 to 7 µm. Piezoelectric plate 182 was then imaged using a programmable ultrasound system with a 5-MHz linear transducer and an ensemble size of 10 at different PRFs. The position of the plate was also measured using the fiber optic micrometer, enabling a comparison to be made with the data obtained using ultrasound.

FIG. 16A is a vibration amplitude image of the plate phantom (i.e., FIG. 18), while FIG. 16B is a vibration frequency image of the plate phantom, indicating that vibrations have been correctly detected at the location of the piezoelectric plate. Because the edges of the plate are attached to the base, the maximum vibration amplitude is expected at the center of the plate, with zero displacement at the edges, which indeed corresponds to what is shown in FIG. 16A. The estimated vibration frequency at the center of the plate is between 450 and 500 Hz. The MUSIC pseudo-spectrum is shown in FIG. 16C, which indicates that the zero-frequency peak corresponds to stationary echo. A prominent double-sided peak is observed at ±500 Hz, corresponding to the vibration frequency of the plate.

FIG. 17A graphically illustrates the ultrasonically estimated vibration amplitude (y-axis) versus the independently measured values using the fiber optic micrometer of FIG. 15 (x-axis) for different drive voltages used to displace the piezoelectric plate. The amplitude and frequency were estimated using the estimators defined in Eqs. (8) and (9). The fiber optic amplitude measurements were made at the center of the plate. FIG. 17B graphically illustrates the ultrasonically estimated frequency (y-axis) versus the function generator frequency (x-axis). A solid line 204 with a slope of unity is shown in both plots. The difference between the estimated and measured values is plotted against the corresponding measured value in FIG. 17C for amplitude and in FIG. 17D for frequency. As can be seen from the Figures, the maximum difference between the detected and measured values is less than 1 µm for amplitude and less than 50 Hz for frequency for both estimators. Some of the differences in amplitude can be attributed to variability in the location on the plate at which the fiber optic measurements were made.

To validate the ability to visualize wall vibrations caused by stenoses and to estimate the vibration spectrum, studies were performed using a pulsatile flow phantom. Experiments were performed on ex vivo lamb arteries. FIG. 18 schematically illustrates the experimental setup, which includes a computer-based controller 140 logically coupled with an oscilloscope 142 and a fiber optic micrometer 148, a Doppler capable ultrasound-imaging machine 144 and an imaging probe 146. Fiber optic micrometer 148 and imaging probe 146 are positioned proximate to an in vivo artery sample 150 disposed in a water bath 152. Pulsatile flow mimicking human arterial flow is created through the artery sample using a pulsatile pump 154. The output of pulsatile pump 154 (a Pulsatron™ pump, available from Pulsafeeder Inc, Punta Gorda, Fla.) is connected to the in vivo artery sample through a damping column 156. Adjusting the height of fluid in the damping column controls the overall flow impedance, such that the Doppler flow profile in the artery can be made to appear visually similar to that of human arterial flow, as shown in FIG. 19.

The time-varying wall displacement is measured using ultrasound as well as the fiber-optic micrometer. The output of the micrometer is digitized using the oscilloscope, and the data are acquired using the computer-based controller. The raw ultrasound data are acquired digitally from inside the ultrasound machine. The power spectra of the wall displacement determined using both methods can then be compared. Stenoses are simulated by partially ligating one part of the artery to reduce the effective lumen diameter. Power spectra measurements are then repeated using both ultrasound and fiber-optic methods.

FIGS. 20A and 20B are vibration amplitude images from two different ex vivo arteries with simulated stenoses. In FIG. 20A, a 30% stenosis is simulated in a 3.4 mm diameter artery. The wall vibrations occur downstream, at a distance of approximately four artery diameters. In FIG. 20B, a 42% stenosis is simulated in a 3.1 mm diameter artery, and the wall vibrations occur closer, approximately three diameters downstream. FIGS. 20A and 20B indicate that using the technique described above, it is possible to distinctly image the location of the artery wall vibrations (and hence, the location of the stenosis). In each image, the stenosis sites are indicated by solid arrows 141, while dash arrows 143 indicate the direction of flow. The region of interest in each image is indicated by a box 145.

FIG. 21 graphically illustrates the mean vibration spectra determined using ultrasound, indicated by an arrow 147, and the fiber-optic micrometer (see FIG. 18, discussed above), indicated by an arrow 149, during peak flow acceleration. The vertical bars indicate the standard deviations. Both spectra have a similar shape, and a break frequency can be observed beyond which the energy drops off rapidly. This result indicates that it is possible to assess the wall vibration spectrum using ultrasound.

In Vivo Vibrations in Human Bypass Vein Grafts

To study the characteristics of pathologic tissue vibrations in vivo, data were collected from a patient with a stenosed bypass vein graft in the femoral artery. A programmable ultrasound machine was used for real-time imaging and data collection, a 5-MHz linear probe was used for imaging and data collection with a PRF of 500 Hz and an ensemble size of 10 pulses in color-flow mode and a PRF of 4-8 kHz in PW Doppler mode.

The vibration-imaging algorithm discussed above in connection with FIG. 3A (preferably employing the ESPRIT method) was implemented on a programmable ultrasound machine, the Hitachi HiVision 5500™, which is manufactured by Hitachi Medical Systems America, Twinsburg, Ohio. All of the signal and image processing on this machine is performed by software, thus providing the flexibility to easily incorporate new algorithms. This system, programmed to use the algorithms disclosed above, enables vibrations to be visualized in real time, facilitating the evaluation of the technique described above during an in vivo procedure.

Data were collected from patients with stenosed bypass vein grafts, who had audible bruits. The vein grafts were first visualized using color-Doppler ultrasound. FIG. 22A is a Color-Doppler image from a stenosed vein graft in a human subject. The PRF was adjusted until the perivascular artifact of the bruit was visible. A vibration amplitude image was then created in real time. FIG. 22B is a vibration amplitude image of the stenosed vein graft of FIG. 9A. Once the bruit was visible in the 2D vibration image, a Doppler sample volume was placed at the location with the maximum vibration amplitude. The vibration spectrum was then generated from the pulsed-wave Doppler data using the technique described above (see FIG. 3A). The "break" frequency in the vibration spectrum was noted.

FIG. 23A is a color power image of a stenosed vein graft, FIG. 23B is a vibration amplitude image of the same stenosed vein graft, and FIG. 23C is a vibration frequency image of the same stenosed vein graft. An arrow 206 indicates the location of the stenosis. A perivascular artifact is visible in the color power image, as indicated by an arrow 208, while the vibration amplitude image clearly shows the origin of the bruit downstream of the stenosis, as indicated by arrows 210. The vibration amplitude is highest close to the vessel wall and decreases farther away from the vessel wall.

To evaluate the vessel wall displacement in more detail, a range gate was placed at the location of the peak vibration amplitude and the displacement was estimated from the phase of the Doppler signal (generally as described above in connection with FIGS. 5A and 5B). The instantaneous position of the vessel wall and the corresponding spectrum are shown as a function of time in FIGS. 24A and 24B. FIG. 24A graphically illustrates instantaneous vessel wall position estimated using the phase of pulsed-wave Doppler data from a stenosed femoral vein graft, with vibrations being indicated in boxes 212. FIG. 24B is a motion periodogram of the signal from FIG. 24A. The displacement spectrum in FIG. 24B shows significant energy up to 200 Hz, and repeats with each cardiac cycle.

A cross section of the spectrum in FIG. 24B at a time of 1.25 seconds is graphically illustrated in FIG. 24C. A peak is observed at the break frequency of about 90 Hz, as indicated by an arrow 214, beyond which the energy decays with increasing frequency. FIG. 24D graphically illustrates the pseudo-spectrum estimated from only 10 ensembles of color-flow data at the same location using the MUSIC algorithm, generally as described in connection with FIG. 3A. A prominent spectral peak is observed at the break frequency, as indicated by an arrow 216. It should be noted that the MUSIC pseudo-spectrum does not reflect the full spectral characteristics, but may be used to estimate the spectral peaks. This case study shows that in vivo tissue vibrations caused by blood flow eddies can be detected using only a short temporal record, demonstrating the feasibility of real-time vibration imaging.

FIG. 25A graphically illustrates the wall displacement spectrum from a normal femoral artery computed using the estimated displacement from pulsed-wave Doppler data. The spectral energy rapidly decays within a few tens of Hz, and the spectral energy beyond 100 Hz is comparable to the noise level. FIG. 25B graphically illustrates the spectrum from a stenosed bypass vein graft. The spectral energy decays more gradually, and a significant energy is present, even at several hundred Hz. An arrow 160 indicates the break frequency, beyond which the energy decays with increasing frequency. FIG. 25C graphically illustrates the spectrum from a second stenosis in the same patient. A peak in the spectrum can be observed at the break frequency, as indicated by an arrow 162. The overall shape of the spectrum is similar to that in FIG. 25B.

FIG. 25D graphically illustrates the spectrum from a vein-graft stenosis in a different patient. Again, a prominent spectral peak can be observed at the break frequency, as indicated by an arrow 164.

For a real-time quantitative assessment of vibration spectra, a scrolling display technique can be implemented, where the horizontal axis represents time, the vertical axis represents frequency on a logarithmic scale, and the pixel intensity represents the vibration intensity. FIGS. 26A-26D graphically illustrate such a time-varying wall vibration spectrum. In a normal femoral artery, represented by FIG. 26A, the spectral energy beyond 45 Hz is comparable to the noise level. In case of stenoses, significant spectral energy is present in the higher frequencies, as graphically illustrated in FIGS. 26B-26D. In all three stenoses (i.e., as shown in FIGS. 26B-26D), the vibration occurs just after the peak systolic wall motion. The break frequency can be determined visually from this time-varying vibration spectral display, as shown by arrows 166, 168, and 170. Automatic detection of these break frequencies can also be performed in real time.

In Vivo Vibrations in Human Coronary Arteries

FIG. 27A is a Doppler spectrum computed using the 2D FFT method described above from a range placed on the myocardial wall of a patient with angiographically confirmed coronary artery disease in the left anterior descending (LAD) artery and the right coronary artery (RCA). The range gate was placed in the vicinity of the RCA. The four phases of myocardial wall motion corresponding to isovolumetric contraction (IVC), ventricular ejection (VE), isovolumetric relaxation (IVR), and ventricular filling (VF) are indicated. A clear harmonic spectrum indicative of high-frequency narrowband vibrations can be observed during the latter part of the ventricular ejection phase. The vibrations have continuously decreasing frequency and appear as oblique bands, and repeat in two consecutive cardiac cycles. The symmetric double-sided peaks are indicative of vibrations observed in the late ventricular ejection phase.

FIG. 27B graphically illustrates a detailed time course of the wall velocity during ventricular ejection, estimated using the autocorrelation method discussed in detail above. The velocity shows oscillatory components indicative of vibrations, as indicated in a boxed enclosed region. The duration of the oscillation is approximately 85 ms, and the oscillation appears to have harmonic components.

FIG. 28A is an angiographic image of a right coronary artery of the patient imaged in FIGS. 27A and 27B, acquired in the left anterior oblique projection with caudal angulation. A diffuse 20% stenosis in the proximal RCA, a tubular 20% stenosis in the mid RCA, and a 40% stenosis in the distal RCA can be identified.

FIG. 28B is a vibration amplitude image overlaid on an apical two-chamber view in diastole from the patient of FIGS. 27A, 27B and 28A. Vibrations in the posterior left-ventricular wall can be seen near the mid and distal portions of the RCA. The vibrations appear to be localized in two regions, which could correspond to the two different lesions in the distal RCA.

FIG. 29A is an angiographic image of the patient imaged in FIGS. 27A, 27B, 28A and 28B, acquired in the right anterior oblique projection with cranial angulation. The proximal LAD is moderately calcified. There is a 50% tubular lesion in the mid-LAD.

FIG. 29B is a vibration amplitude image overlaid on the apical two-chamber view of the patient of FIG. 29A. Myocardial vibrations can be observed in the mid-LAD section.

Differentiating Tissue Vibrations Arising from A Stenosis from Other Sources

Vibrations are produced due to pressure differences across an orifice. Stenoses represent a relatively common physiological features including orifices where such pressure differences exist. However, other physiological features, such as punctured blood vessels, also include orifices with pressure differences which can generate vibrations. The following provides a description of how the vibration imaging techniques disclosed herein can distinguish stenoses from other sources of tissue vibrations.

In a stenosis, the pressure difference is typically more significant during systole, whereas in a bleeding vessel the pressure difference could be significant in diastole as well. Thus, analyzing the vibrations with respect to the time at which they occur in the cardiac cycle will provide data that can be used to distinguish vibrations associated with a stenosis from vibrations associated with bleeding.

Referring to FIG. 1, tissue vibration processor 28 can be configured to determine the timing of the vibrations in the cardiac cycle using electrocardiograph signals. In another embodiment, the tissue vibration processor can be configured to determine the timing of the vibrations during the cardiac cycle using the periodicity of tissue motion due to cardiac pulsation.

Exemplary System for Routine Patient Screening

The vibrometry techniques disclosed herein can be beneficially employed to evaluate renal, cerebral and coronary arteries for stenoses. In an exemplary, but not limiting embodiment, a user friendly, simple to operate, and relatively inexpensive system is implemented, to enable widespread screening of patients. Such widespread screening will be very useful in detecting stenoses in low risk populations, where one might not expect such stenoses to be likely. Furthermore, where such screening is readily available it will become possible to screen specific patients during treatment with statins and/or other drug therapies, to determine whether or not such therapies are effective. The empirical data such screening can provide can thus reduce over treatment (where more drug therapy than needed is provided) and under treatment (where less drug therapy than needed is provided). Such screening can also be used to identify patients for whom drug therapy is ineffective, so that other treatments (such as surgery) can be considered. Such screening could be beneficially employed by primary care providers, as well as emergency care providers.

FIG. 30 schematically illustrates a vibrometry screening system 210, which includes a receiver 212, a processor 214, an output 216, and an optional targeting jig 218. As discussed above, a conventional ultrasound transducer for B-mode ultrasound can be beneficially employed as a receiver. Such transducers are relatively inexpensive and are readily available. In an exemplary but not limiting embodiment, a phased array ultrasound transducer is employed. The processor will be generally similar to processors employed in B-mode or Doppler mode ultrasound imaging systems, although the processor will be configured to manipulate the signal from the transducer differently than when such a signal is used to generate an echogram (i.e., a B-mode or Doppler mode ultrasound image, based on reflections from interfaces in a tissue mass). The processor will generally be implemented using a general purpose computing processor implementing machine instructions to carry out specific functions (where the machine instructions control the functions being implemented). Those of ordinary skill in the art sometimes refer to such processors as software or code based. If desired, the processor can also be implemented as a hardware based processor, where the physical configuration of the circuitry is used to control the functions being implemented, as opposed to the use of machine instructions. Application specific integrated circuits are one such type of hardware processor. The specific functions implemented by the processor include signal processing (such signal processing functions are generally discussed above to manipulate the vibration data collected from the tissue, noting that such processing is distinctly different than the type of signal processing used to generate an echogram; i.e., a B-mode or Doppler mode image) and output processing. The output processing is a function of the type of output desired.

It is possible to provide a stenosis screening system in accord with the concepts disclosed herein that does not rely on displaying an image to the operator. The concepts disclosed herein specifically encompass stenosis screening systems where audible or haptic feedback is used to alert the operator that a stenosis has been detected in the region of tissue from which vibration data has been collected. It should also be noted that as many patients will not exhibit any stenoses, the concepts disclosed herein encompass screening systems that output an indication that no stenosis has been detected (such an output lets the operator know that the system is functioning). In systems that provide both types of outputs (i.e., no stenosis detected as well as stenosis detected) the indications are readily identifiable (for example, a green light indicating no stenosis, with a red light indicating a stenosis; or a first graphical icon (or first audible tone or first recorded statement) indicating no stenosis, with a very different graphical icon (or very different audible tone or recorded statement) indicating a stenosis). The system processor will perform the processing required to implement the selected output.

In an exemplary, but not limiting embodiment, the relative anatomical location of a detected stenosis will be visually presented to the user on a display. In certain implementations, where the system is specifically configured to collect reflected ultrasound waves from the tissue mass and produce an echogram (i.e., a B-mode or Doppler mode ultrasound image) in addition to collecting and processing the vibration data to detect any stenosed vessel in the tissue mass, the location of the stenosis will be identified on the echogram. In other embodiments, no echogram is produced. Rather, a schematic illustration of the tissue mass being screened for stenoses is displayed, and the locations of any detected stenoses will be identified. For example, in the context of coronary arteries, a schematic illustration of the heart can be displayed, and the relative locations of any stenoses will be identified. In some embodiments, the display will be presented after the screening is completed, while in other embodiments the display will be updated in real-time, such that if the operator moves the transducer to a different position, then a different stenosis may be detected. The complexity of the schematic illustration can vary from very simple to very complex, depending on how much information the system designer wishes to convey. The physical location of the transducer relative to the patient during the screening can be used to determine where the stenosis is located, and how the schematic illustration should be rendered for display to the operator. Position tracking and registration of medical devices is well understood in the art.

In some embodiments, a relative magnitude or severity of the stenosis will be indicated. For example, the greater the degree of occlusion caused by the stenosis, the greater the resulting vibration. Thus, the intensity of the vibration can be measured to provide an indication of the severity of the stenosis.

Optional targeting jig 218 can be implemented in screening systems intended for use by operators having relatively little anatomical training. Individuals with specialized anatomical training are likely to be able to properly position a transducer to enable renal, cerebral, or cardiac stenoses to be detected without the assistance of a targeting jig. The use of such a targeting jig, customized for properly positioning the transducer relative to the locations of different types of arteries, will facilitate use of such screening systems by operators with less specialized anatomical training. For example, a first type of targeting jig can be used to help an operator position the transducer in a location enabling cerebral stenoses to be screened, a second type of targeting jig can be used to help an operator position the transducer in a location enabling cardiac stenoses to be screened, and a third type of targeting jig can be used to help an operator position the transducer in a location enabling renal stenoses to be screened.

Specific examples of schematic illustrations used as outputs and targeting jigs are discussed below in the context of the screening of cardiac arteries.

Using Vibrometry to Detect Stenoses in Coronary Arteries

Coronary arteries are present in three rings around the periphery of the heart. Because of their relative depth within body tissue, and their relatively small size, they cannot be visualized using an echogram (i.e., a B-mode or Doppler mode ultrasound image formed using ultrasound energy reflected at interfaces in cardiac tissue). This inability appears to be based on physical limitations, and advances in medical ultrasonography are not likely to eliminate this limitation (as the limitation is inherent in the physical properties of ultrasound waves).

Thus, one significant aspect of the concepts disclosed herein is that vibrations from stenotic coronary arteries can be detected, even when such arteries are too small to be visualized using B-mode or Doppler mode ultrasound imaging. Note that even though coronary arteries cannot be seen using echograms, cardiac specialists are very familiar with B-mode and Doppler mode ultrasound imaging, as such techniques are useful in analyzing relatively larger cardiac structures (such as valves and chambers) and blood flow through such larger structures. Thus, cardiologists will likely find screening systems that include ultrasound imaging capabilities in addition to vibrometry capabilities to be useful. Of course, the concepts disclosed herein also encompass cardiac screening systems that are meant for use by non cardiologists, to enable coronary artery stenosis to be more widely performed.

FIG. 31 schematically illustrates an exemplary targeting jig 220 that can be used to facilitate the proper positioning of a transducer for detecting stenotic cardiac artery vibrations. Targeting jig 220 including a first transducer position 222, a second transducer position 226, and a third transducer position 228, as well as a support structure 224. The support structure is sized and shaped to fit comfortably on the patient's chest. It is expected that most patient body sizes and shapes can be accommodated by one type of cardiac targeting jig, although pediatric applications, as well as applications for body sizes varying widely from the norm may require a different targeting jig. Alternately, the support structure can be adjustable, so the structure can be varied to fit a wider variety of body shapes. Instructions and diagrams can be provided to illustrate how the support structure should be fitted to a patient. The support structure can be fabricated from many different materials. The type of flexible lead aprons used to protect patients from X-rays could be used as one type of support structure, recognizing that such a support structure is exemplary, and not limiting.

With support structure 224 properly positioned on a human patient, first transducer position 222 is disposed proximate the super sternum notch, an anatomical feature present in human anatomy. The sternum, a long flat bone in the center of the human chest, can interfere with the transmission and reflection of ultrasound waves, and the collection of vibrations from stenoses coronary arteries. The transducer must be placed in a position relative to the heart and the sternum such that the sternum does not prevent ultrasound from the transducer from reaching the tissue containing the arteries to be scanned, and that vibrations from stenosed arteries in the heart can reach the transducer. The super sternum notch represents a location at which the transducer can be positioned to collect vibrations from stenosed arteries in the heart without such vibrations being blocked by the sternum.

Second transducer position 226 is disposed proximate the left sternal socket, another anatomical feature present in human anatomy. Again, the left sternal socket represents a location at which the transducer can be positioned to collect vibrations from stenosed arteries in the heart, without such vibrations being blocked by the sternum. Third transducer position 228 is disposed proximate the sub costal socket, yet another anatomical feature present in human anatomy. Similarly, third transducer position 228 represents yet another location at which the transducer can be positioned to collect vibrations from stenosed arteries in the heart, without such vibrations being blocked by the sternum.

It should be recognized that the three identified transducer positions are intended to be exemplary, rather than limiting. Other transducer positions may also be useful, and some embodiments of targeting jigs may include more or fewer than the three transducer positions identified herein.

FIG. 32 is a schematic plan view of targeting jig 220 positioned on a patient, so that transducers placed in transducer positions 222, 226, and 228 will be properly positioned to detect stenotic vibrations from a heart 230. It should be understood that the relative sizes, shapes, and locations of the targeting jig, the patient, and the heart shown in FIG. 32 are intended to be illustrative, rather than limiting. The targeting jig can include one or more straps 225 to provide stability.

FIG. 33 is a schematic side elevation view of targeting jig 220 positioned on a patient, so that transducers placed in transducer positions 222, 226, and 228 will be properly positioned to detect stenotic vibrations from heart 230. Note that care needs to be taken when positioning the transducer at transducer position 222. If the transducer were positioned flat onto the patient's skin, the transducer would be optimally positioned to collect vibrations along an axis 232. However, heart 230 is along an axis 234. The positioning of the transducer must take into account the relative location of heart 230, and the propagation path of the vibrations. Operators who have specialized anatomical training will be able to quite readily achieve the proper positioning. For operators with less specialized anatomical training, proper positioning of the transducer can be accommodated either by prepositioning the transducers at each transducer position (such that the targeting jig includes a plurality of transducers), or by configuring a socket at each transducer position such that a transducer (such as an ultrasound imaging probe) can only be inserted into the socket in an orientation determined to enable ultrasound energy to be directed from the transducer toward the heart, and reflected ultrasound energy modified by stenotic vibrations to be received back at the transducer, when the targeting jig is properly positioned on a patient. It should be understood that the relative sizes, shapes, and locations of the targeting jig, the patient, the heart and the axes shown in FIG. 33 are intended to be illustrative, rather than limiting.

FIG. 34 is an enlarged side elevation view of targeting jig 220 positioned on a patient, showing an ultrasound imaging probe 234 being used as a transducer, with the ultrasound imaging probe positioned in a custom housing 232, to enable the probe to receive vibrations from stenosed arteries in heart 230. Housing 232 is sized and shaped to engage a socket 223 formed into the targeting jig at transducer position 222. Housing 232 includes an acoustic waveguide 239 that changes an effective angular orientation of the ultrasound transducer in ultrasound imaging probe 234 relative to heart 230. A volume 238 in housing filled with an acoustically coupling material, such as coupling gel. The function of acoustic waveguide 236 is to redirect the direction of ultrasound energy from the transducer to the heart, and energy reflected back form the heart to the transducer. Note vibration energy from stenosed arteries in heart 230 traveling along an axis 237 is redirected along an axis 239, so that the vibrations will be collected by the ultrasound transducer in the ultrasound imaging probe. The specific angular dimensions of acoustic waveguide 236 will be determined based on the size and shape of the targeting jig and socket 223, such that the selected dimensions will facilitate collection of stenotic vibrations from coronary arteries. While not specifically shown, it should be understood that positioning sensors can be included on the targeting jig and the ultrasound imaging probe to enable the relative position of any detected stenoses to be determined.

FIG. 35 is similar to FIG. 34, but shows an alternative socket configuration for facilitating the proper orientation of ultrasound imaging probe 234 relative to heart 230. In this embodiment, no supplemental housing is required, the ultrasound imaging probe 234 is simply placed in contact with an acoustic waveguide 236*a*. Again, the specific angular dimensions of acoustic waveguide 236*a* will be determined based on the size and shape of the targeting jig and transducer position 222, such that the selected dimensions will facilitate collection of stenotic vibrations from coronary arteries.

FIG. 36 graphically illustrates an exemplary output for use in a scanning system for coronary stenoses. An arterial map 244 showing major coronary arteries 246 is presented to a user on a display 242. A graphical icon 248 is used to indicate the detection of a stenosis. The arterial map can simply be an animation, it need not be based on a B-mode or Doppler mode ultrasound image. It should be understood that the arterial map of FIG. 36 is exemplary, and not limiting. Other types and styles, including rotatable three dimensional illustrations of a heart, can also be used.

FIG. 37 graphically illustrates an exemplary method for using a stenotic artery scanning system. In a block 250 a targeting jig is positioned on the patient. In a block 252 ultrasound is used to scan for stenotic arteries, generally as discussed above. In a block 254, an indication of the scanning is output to the operator (the indication will inform the operator if any stenoses were detected, and preferably even inform the operator that no stenoses were detected).

One additional aspect of the vibrometry concepts disclosed herein is using the unique shear signal from the pericardium to verify that the ultrasound is being directed toward and collected from the coronary arteries. The pericardium represents an interface layer that can be identified in an ultrasound image, and the coronary arteries are located close to the pericardium. Thus identifying the pericardium in an ultrasound image (where such images are obtained as part of the scanning process) can be used to verify that the ultrasound transducer is properly positioned.

For cardiac applications in particular, the scanning process can use information about the time in the cardiac/pulse cycle to process vibrations and to differentiate mild vs. severe stenoses based on the duration and/or timing of the bruit differential vibration.

SUMMARY

Empirical evidence demonstrates the feasibility of real-time ultrasound imaging of low-intensity local vibrations in the vessel wall and surrounding tissue associated with stenosed blood vessels. Several algorithms based on parametric signal decomposition and spectral estimation have been developed for imaging small-amplitude tissue vibrations using as few as 10 temporal samples. Simulations show that these algorithms have high sensitivity (96 to 98%) and specificity (98 to 99%) for detecting vibrations in the presence of clutter as well as blood flow, and are robust even when broadband vibrations are present. The vibration amplitude and frequency can be estimated accurately, and real-time tissue vibration imaging has been implemented on an ultrasound machine with a software-programmable subsystem. Vibrations were observed in stenosed bypass vein grafts and from coronary arteries in human subjects.

Tissue vibration imaging can provide additional diagnostic information that is currently not available to the clinician using conventional tools. An ultrasound device with tissue vibration imaging capability can become a useful screening and diagnostic tool for the assessment of stenoses and other vascular abnormalities traditionally associated with bruits that are otherwise hard to diagnose using conventional duplex ultrasound. The ultrasonic vibration imaging techniques disclosed herein are attractive because of their potential to visualize small-amplitude vibrations at their origin. The vibration spectra can be used to compute the break frequency, which is directly related to the residual lumen diameter at the stenosis. An important application of tissue vibration imaging will likely be the non-invasive diagnosis of coronary artery stenoses. Conventional duplex ultrasound is limited by the difficulty in visualizing coronary arteries and the poor scattering strength from coronary blood flow. Patients with coronary artery stenosis have diastolic murmurs with frequencies between 300 Hz and 800 Hz. Thus, clinically significant coronary artery stenoses are expected to create vibrations with amplitude and frequency dependent on coronary flow rate and minimum residual lumen diameter. Transthoracic assessement of the heart wall vibrations produced by coronary artery disease can become an inexpensive and effective method for diagnosing clinically significant coronary artery stenoses.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for detecting a stenosis, comprising the steps of:
generating ultrasound data reflected from an internal site using an ultrasound machine including an ultrasound transducer and an ultrasound back-end subsystem;
extracting tissue vibration data from the ultrasound data using a tissue vibration processor, where the tissue vibration processor decreases components of the ultrasound data induced by transducer movement, respiration and cardiac pulsation in the tissue vibration data, such that the tissue vibration data corresponds to vibrations caused by blood flow turbulence, the blood flow turbulence being
indicative of the stenosis; carrying out the following with the ultrasound back-end subsystem programmed with non-transitory computer readable media instructions: from the tissue motion signal, the vibration image indicating a spatial position of the tissue motion relative to the internal site;
generating a B-mode image from the ultrasound data showing underlying anatomy of the internal site;
overlaying the generated vibration image with the generated B-mode image so as to provide stenosis position information with reference to the underlying anatomy of the internal site; and
outputting the overlaid images.

2. The method of claim 1, further comprising the step of quantifying hemodynamic properties of the stenosis based on an amplitude of the tissue vibration data.

3. A method for detecting a stenosis, comprising the steps of:
generating and collecting ultrasound data reflected from an internal site using an ultrasound machine including an ultrasound transducer and an ultrasound back-end subsystem; yielding an ultrasound signal;
processing the ultrasound signal using a tissue vibration processor to obtain a tissue vibration signal corresponding to soft-tissue vibrations at the internal site caused by blood flow turbulence, the blood flow turbulence being indicative of the stenosis, wherein contributions from sources other than soft tissue vibrations caused by the stenosis have been reduced in the
tissue vibration signal; carrying out the following with the ultrasound back-end subsystem programmed with non-transitory computer readable media instructions: from the tissue vibration signal, the vibration image indicating a spatial position of the soft-tissue vibrations caused by blood flow turbulence relative to the internal site;
generating a B-mode image from the ultrasound signal showing underlying anatomy of the internal site;
generating a color-flow image from the ultrasound signal indicative of blood flow at the internal site;
overlaying the generated vibration image with the generated B-mode image and with the generated color-flow image so as to provide stenosis position information with reference to the underlying anatomy and blood flow of the internal site.

4. The method of claim 3, further comprising the step of determining a location of the stenosis using the tissue vibration signal.

5. The method of claim 3, wherein the tissue vibration signal is obtained by processing the ultrasound data from multiple depth locations.

6. The method of claim 3, wherein the step of processing the ultrasound data further comprises the step of filtering out clutter and noise at frequencies that are lower than an expected frequency range of tissue vibrations corresponding to the stenosis.

7. The method of claim 3, wherein the step of processing the ultrasound data further comprises the step of filtering out noise that is at frequencies higher than an expected frequency range of tissue vibrations corresponding to the stenosis.

8. The method of claim 3, wherein the vibration image comprises a vibration amplitude image where the tissue vibrations are color-coded according to the vibration amplitude, and/or a vibration frequency image where the tissue vibrations are color-coded according to the vibration frequency.

9. The method of claim 3, further comprising the step of grading a stenosis using a frequency and an amplitude of the tissue vibrations.

10. A non-transitory computer readable memory medium having machine instructions executable by a computing device for carrying out the steps of claim 3.

11. A method for detecting a stenosis using ultrasound data, comprising the steps of:
- generating ultrasound data reflected from an internal site using an ultrasound machine including an ultrasound transducer;
- processing the ultrasound data using a tissue vibration processor, programmed with non-transitory computer readable media instructions, to identify tissue vibrations at the internal site, producing a tissue vibration signal from which contributions to the tissue vibration from a source other than blood flow turbulence, the blood flow turbulence being indicative of the stenosis at the internal site has been reduced, said tissue vibration signal providing an indication of the stenosis, wherein processing the ultrasound data comprises:
  - (a) estimating a correlation signal from an ensemble of the ultrasound data;
  - (b) carrying out an eigen decomposition of the correlation signal to identify a signal subspace and a noise subspace;
  - (c) estimating a frequency of dominant vibration components in the signal subspace and the noise subspace; and
  - (d) based upon an estimate of the frequency of the dominant vibration components, determining a vibration amplitude and a vibration frequency, at least one of the vibration amplitude and the vibration frequency comprising the tissue vibration signal; and
- outputting an indication of the tissue vibration signal to a user in a format perceptible to the user, to enable the user to detect the stenosis, wherein the indication conveys to the user that a stenosis is present at the internal site.

12. A method for detecting a stenosis using ultrasound data, comprising the steps of:
- generating ultrasound data reflected from an internal site using an ultrasound machine including an ultrasound transducer;
- processing the ultrasound data using a tissue vibration processor, programmed with non-transitory computer readable media instructions, to identify tissue vibrations at the internal site, producing a tissue vibration signal from which contributions to the tissue vibration from a source other than blood flow turbulence, the blood flow turbulence being indicative of the stenosis at the internal site has been reduced, said tissue vibration signal providing an indication of the stenosis, wherein processing the ultrasound data comprises:
  - (a) computing coefficients of an autoregressive process from an ensemble of the ultrasound data;
  - (b) computing linear prediction filter coefficients from the coefficients;
  - (c) estimating a power spectrum from the linear prediction filter coefficients and detecting peaks in the power spectrum; and
  - (d) based upon an estimate of the power spectrum and the peaks, determining a vibration amplitude and a vibration frequency, at least one of the vibration amplitude and the vibration frequency comprising the tissue vibration signal; and
- outputting an indication of the tissue vibration signal to a user in a format perceptible to the user, to enable the user to detect the stenosis, wherein the indication conveys to the user that a stenosis is present at the internal site.

13. Apparatus for detecting a stenosis at an internal site using ultrasound, comprising:
- an ultrasound transducer configured to receive ultrasound data;
- an ultrasound transducer controller coupled to the ultrasound transducer to control operation of the ultrasound transducer; and
- an ultrasound back-end subsystem configured to:
  - process the ultrasound data to identify tissue vibrations caused by the stenosis, thereby producing a tissue vibration signal corresponding to soft-tissue vibrations at the internal site caused by blood flow turbulence, the blood flow turbulence being indicative of the stenosis, wherein contributions from sources other than soft tissue vibrations caused by the stenosis have been reduced in the tissue vibration signal;
  - generate a vibration image from the tissue vibration signal with a tissue vibration processor;
  - generate a B-mode image from the ultrasound signal showing underlying anatomy of the internal site;
  - overlay the generated vibration image with the generated B-mode image; and
  - output the overlaid images so as to provide stenosis position information with reference to the underlying anatomy and blood flow of the internal site.

14. The apparatus of claim 13, wherein the tissue vibration signal produced by the ultrasound back-end subsystem localizes the stenosis by determining a location of the tissue vibrations.

15. The apparatus of claim 13, further comprising a display, and wherein the ultrasound back-end subsystem outputs the overlaid images to the display.

16. The apparatus of claim 15, wherein the ultrasound back-end subsystem further confirms that vibrations displayed in the vibration image correspond to the stenosis at the site by placing a range gate at a location of the tissue vibration, producing a tissue vibration spectrum.

17. The apparatus of claim 15, wherein the vibration image comprises at least one of a vibration amplitude image where the tissue vibrations are color-coded according to the vibration amplitude and a vibration frequency image where the tissue vibrations are color-coded according to the vibration frequency.

18. The apparatus of claim 13, wherein the ultrasound back-end subsystem comprises at least one of an application specific integrated circuit and a general purpose processor that executes software to identify the tissue vibrations and produce the tissue vibration signal.

19. The apparatus of claim 13, wherein the ultrasound back-end subsystem filters the tissue vibration signal by filtering out clutter and noise at frequencies that are substantially lower than an expected frequency range of tissue vibrations corresponding to the stenosis at the site.

20. The apparatus of claim 13, wherein the ultrasound back-end subsystem filters the tissue vibration signal by filtering out clutter and noise at frequencies that are substantially higher than an expected frequency range of tissue vibrations corresponding to the stenosis at the site.

21. The apparatus of claim 13, wherein the ultrasound back-end subsystem determines timing of vibrations in a cardiac cycle using electrocardiograph signals.

22. The apparatus of claim 13, wherein the ultrasound back-end subsystem determines timing of vibrations in cardiac cycle using the periodicity of tissue motion due to cardiac pulsation.

23. The apparatus of claim 13, further comprising a Doppler processor, for producing a Doppler image of the internal site.

24. Apparatus for detecting a stenosis at an internal site using ultrasound, comprising:
- an ultrasound transducer for receiving ultrasound data;
- an ultrasound transducer controller coupled to the ultrasound transducer to control its operation; and
- a tissue vibration processor that processes the ultrasound to identify tissue vibrations caused by the stenosis, producing a tissue vibration signal corresponding to soft-tissue vibrations at the internal site caused by blood flow turbulence, the blood flow turbulence being indicative of the stenosis, wherein contributions from sources other than soft tissue vibrations caused by the stenosis have been reduced in the tissue vibration signal, wherein the tissue vibration processor determines tissue vibrations at the internal site by:
  - (a) estimating a correlation matrix from the color-flow signal;
  - (b) carrying out an eigen decomposition of the correlation matrix to identify a signal subspace and a noise subspace;
  - (c) estimating a frequency of dominant vibration components in the signal subspace and the noise subspace; and
  - (d) based upon an estimate of the frequency of the dominant vibration components, determining a vibration amplitude estimate and a vibration frequency estimate, at least one of the vibration amplitude estimate and the vibration frequency estimate comprising the tissue vibration signal.

25. Apparatus for detecting a stenosis at an internal site using ultrasound, comprising:
- an ultrasound transducer for receiving ultrasound data;
- an ultrasound transducer controller coupled to the ultrasound transducer to control its operation; and
- a tissue vibration processor that processes the ultrasound to identify tissue vibrations caused by the stenosis, producing a tissue vibration signal corresponding to soft-tissue vibrations at the internal site caused by blood flow turbulence, the blood flow turbulence being indicative of the stenosis, wherein contributions from sources other than soft tissue vibrations caused by the stenosis have been reduced in the tissue vibration signal, wherein the tissue vibration processor determines tissue vibrations at the internal site by:
  - (a) estimating a mean clutter velocity from the color-flow signal, using autocorrelation;
  - (b) down mixing the color-flow signal with the mean clutter velocity, producing a down mixed signal;
  - (c) computing a phase of the down mixed signal and a mean phase of the down mixed signal;
  - (d) subtracting the mean phase from the phase of the down mixed signal, producing a residual phase;
  - (e) decomposing the residual phase into its dominant components; and
  - (f) applying energy and frequency thresholds to substantially suppress any contribution to the tissue vibration due to noise and blood flow, yielding an estimate of vibration amplitude and vibration frequency of tissue.

26. The apparatus of claim 25, wherein the tissue vibration processor decomposes the residual phase by:
  - (a) estimating a correlation matrix from the residual phase; and
  - (b) performing an eigen decomposition of the correlation matrix to determine the dominant components.

27. Apparatus for detecting a stenosis at an internal site using ultrasound, comprising:
- an ultrasound transducer configured to receive ultrasound data;
- an ultrasound transducer controller coupled to the ultrasound transducer to control operation of the ultrasound transducer; and
- an ultrasound back-end subsystem configured to:
  - process the ultrasound data to identify tissue vibrations caused by the stenosis, thereby producing a tissue vibration signal corresponding to soft-tissue vibrations at the internal site caused by blood flow turbulence, the blood flow turbulence being indicative of the stenosis, wherein contributions from sources other than soft tissue vibrations caused by the stenosis have been reduced in the tissue vibration signal;
  - generate a vibration image from the tissue vibration signal with a tissue vibration processor;
  - produce a color-flow image indicative of blood flow at the internal site,
  - overlay the color-flow image with the vibration image; and
  - output the overlaid color-flow image with the vibration image to provide stenosis position information with reference to the blood flow at the internal site.

28. A method for detecting a stenosis, comprising the steps of:
- generating ultrasound data reflected from an internal site using an ultrasound machine including an ultrasound transducer and an ultrasound back-end subsystem;
- extracting tissue vibration data from the ultrasound data using a vibration processor, where the vibration processor decreases components of the ultrasound data induced by transducer movement, respiration and cardiac pulsation in the tissue vibration data, such that the tissue vibration data corresponds to vibrations caused by blood flow turbulence, the blood flow turbulence being indicative of the stenosis; carrying out the following with the ultrasound back-end subsystem programmed with non-transitory computer readable media instructions: from the tissue motion signal, the vibration image indicating a spatial position of the tissue motion relative to the internal site;
- generating a color-flow image from the ultrasound data indicative of blood flow at the internal site;
- overlaying the generated vibration image with the generated color-flow image so as to provide stenosis position information with reference to the blood flow at the internal site; and
- outputting the overlaid images.

* * * * *